US006942861B2

(12) United States Patent
McKee et al.

(10) Patent No.: US 6,942,861 B2
(45) Date of Patent: *Sep. 13, 2005

(54) HISTIDINE-TAGGED INTIMIN AND METHODS OF USING INTIMIN TO STIMULATE AN IMMUNE RESPONSE AND AS AN ANTIGEN CARRIER WITH TARGETING CAPABILITY

(75) Inventors: Marian L. McKee, Great Falls, VA (US); Alison D. O'Brien, Bethesda, MD (US); Marian R. Wachtel, Gaithersburg, MD (US)

(73) Assignee: Henry M. Jackson Foundation for the Advancement of Military Medicine, Rockville, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/837,459

(22) Filed: Apr. 18, 1997

(65) Prior Publication Data

US 2002/0006407 A1 Jan. 17, 2002

Related U.S. Application Data

(60) Provisional application No. 60/015,657, filed on Apr. 19, 1996, and provisional application No. 60/015,936, filed on Apr. 22, 1996.

(51) Int. Cl.[7] ............................................. A61K 39/00
(52) U.S. Cl. ............................. 424/169.1; 424/164.1; 424/184.1; 424/185.1; 424/257.1; 424/234.1; 530/350; 530/388.2; 530/387.1; 530/388.4; 435/320.1; 435/69.1; 435/325; 435/252.33; 435/6; 435/410; 435/420
(58) Field of Search ........................ 424/169.1, 185.1, 424/164.1, 257.1, 184.1, 234.1, 200.1, 491, 198.1, 190.1; 435/320.1, 325, 69.1, 252.33, 6, 410, 420, 252.3; 530/388.4, 388.1, 388.2, 387.1, 350, 402; 800/6, 288; 536/23.71

(56) References Cited

U.S. PATENT DOCUMENTS

| | | | | |
|---|---|---|---|---|
| 4,141,970 A | * | 2/1979 | Chidlow et al. | 424/92 |
| 4,736,017 A | | 4/1988 | O'Hanley et al. | 424/190.1 |
| 4,740,585 A | | 4/1988 | Schmidt et al. | 530/300 |
| 5,049,500 A | | 9/1991 | Arnizen et al. | 435/172.3 |
| 5,310,654 A | * | 5/1994 | Isberg et al. | 435/6 |
| 5,378,824 A | | 1/1995 | Bedbrook et al. | 536/23.6 |
| 5,681,736 A | * | 10/1997 | Pace et al. | 424/252.1 |
| 5,702,727 A | * | 12/1997 | Amkraut et al. | 424/491 |
| 5,747,293 A | * | 5/1998 | Dougan et al. | 530/402 |
| 5,759,551 A | * | 6/1998 | Ladd et al. | 424/198.1 |
| 5,798,260 A | * | 8/1998 | Tarr et al. | 435/252.3 |
| 5,800,821 A | * | 9/1998 | Acheson et al. | 424/200.1 |
| 5,858,352 A | * | 1/1999 | Pace et al. | 424/93.4 |
| 5,914,114 A | * | 6/1999 | Cassels | 424/241.1 |
| 6,245,892 B1 | * | 6/2001 | Oaks et al. | 530/350 |
| 6,261,561 B1 | * | 7/2001 | Stewart, Jr. et al. | 424/184.1 |
| 6,277,379 B1 | * | 8/2001 | Oaks et al. | 424/197.11 |
| 6,406,885 B1 | | 6/2002 | Stewart et al. | 435/69.1 |
| 2002/0006407 A1 | * | 1/2002 | McKee et al. | 424/184.1 |

FOREIGN PATENT DOCUMENTS

| | | | |
|---|---|---|---|
| CA | 2078716 | * | 9/1992 |
| CA | 2078716 | * | 3/1994 |
| EP | 0 222 835 B1 | | 5/1987 |
| EP | 0282042 | | 9/1988 |
| WO | 90/02484 | | 3/1990 |
| WO | 92/02820 | | 2/1992 |
| WO | 95/15678 | | 6/1994 |
| WO | 94/20135 | | 9/1994 |
| WO | 96/00233 | | 1/1996 |
| WO | 96/12801 | | 5/1996 |

OTHER PUBLICATIONS

Cravioto, A et al, The Journal of Infectious Diseases, vol. 163, pp. 1247–1255, 1991.*
Dean–Nystrom, E et al, 4th International Shiga toxin producing *E. coli* meeting, Kyoto, Japan, Oct. 2000, abstract.*
Campbell, Ailsa M. Monoclonal Antibody and Immunosensor technology, Chapter 1, pp. 1–49, specifically p. 3, 1991.*
Agin, TS et al, Cytotoxins, Cholera and the gut, pp. 315–320, 1995.*
Cravioto, A et al, The Journal of Infectious Deseases, vol. 163, pp. 1247–1255, 1995.*
Ashkenazi, S et al, J. Pediatrics, Dec. 1988, vol. 113(6), pp. 1008–10014, (abstract), 1988.*

(Continued)

Primary Examiner—L. J. Smith
Assistant Examiner—Ginny Allen Portner
(74) Attorney, Agent, or Firm—Finnegan, Henderson, Farabow, Garrett & Dunner, LLP.

(57) ABSTRACT

The present invention describes the isolation and purification of histidine-tagged functional portions of intimin (his-tagged intimin or his-intimin), a protein associated with the ability of certain strains of pathogenic bacteria to adhere to epithelial cells. The invention further describes the use of intimin as an antigen to promote a protective immune response. In addition, the invention describes the combination of intimin with one or more other antigens and administration of the combination to promote a protective immune response against intimin and the one or more antigens.

One aspect of the invention is the administration of intimin to target specific epithelial cells to promote a protective immune response to intimin proteins. Additional aspects of the invention include the use of intimin or intimin combined with one or more antigens and administration of the combination to target gastrointestinal mucosa and stimulate an immune response. Additionally, the invention describes administration of the combination of intimin combined with drugs, to provide a means for targeted delivery of drugs to specific epithelial cells. Other aspects of the invention include the production of antibodies directed against his-intimin and methods of using such antibodies to provide passive immune protection, and in an assay system.

38 Claims, 18 Drawing Sheets

OTHER PUBLICATIONS

Agin, T.S et al, Cytokines, cholera and the gut, pp. 315–320, Nov., 1995, IOS, Ohmsha.*

Butterton, J et al, Abstracts of the General meeting of the American society for Microbiology, vol. 95(0), May 21–25, p. 294, 1995.*

Cirillo, J.D. et al, Clinical Infectious Diseases, vol. 20, pp. 101–1009, 1995.*

McDonough, Sean P. et al, Am. J. Vet. Res, vol. 55, No. 11, Nov., 1994.*

Cravioto et al, J. Infect. Dis., vol. 163, p 1247–1255, 1991.*

Butterton, J. R. et al, Abstracts of the Gen Meeting of the Am. Soc. Microbiologists, vol. 95(0), p 294, #E77, 1995.*

Lourie, M et al, Oct. 1993, Infect. Immun., vol. 61(10), p 4085–4092.*

McKee et al (May 1995), Am. Soc. of Microbiol, p. 166, Abstract #B–5, Monday Session 18.*

McKee, ML (1995) Dissertation Abstracts Int., vol. 56(78), p. 3583, (abstract).*

Leong, J.H. et al, Jun., 1990, vol. 9(6), EMBO J., pp. 1979–1989.*

Chart, H. et al, J. Clin. Microbiol, 1989, vol. 27(2), p 285–290.*

Toth, I et al, J. Clin. Microbiol, 1991, vol. 29(5), p 1016–1019.*

Rice, E.W. et al, J. Clin. Microbiol, 1992, vol. 30(5), p 1315–1316.*

Isberg, R. B., Science, May 17, 1991, vol. 252(5008), p 934–938.*

G. Frankel et al., "Intimin from Enteropathogenic *Escherichia coli* Restores Murine Virulence to a *Citrobacter rodentium* eaeA Mutant: Induction of an Immunoglobulin A Response to Intimin and EspB," Infection and Immunity, 64(12):5315–5325 Dec. 1996.

S. Barzu et al., "Characterization of B–Cell Epitopes on IpaB, an Invasion–Associated Antigen of *Shigella flexneri*: Identification of an Immunodominant Domain Recognized during Natural Infection," Infection and Immunity, 61(9):3825–3831 (1993).

T.K. McDaniel et al., "A Genetic Locus of Enterocyte Effacement Conserved Among Diverse Enterobacterial Pathogens," Proc. Natl. Acad. Sci. USA, 92:1664–1668 (1995).

M. Simonet et al., "Immunization with Live aroA Recombinant *Salmonella typhimurium* Producing Invasion Inhibits Intestinal Translocation of *Yersinia pseudotuberculosis*," Infection and Immunity, 62(3):863–867 (1994).

Abstract: Evelyn Dean–Nystrom, Lisa Gansheroff, Edda Twiddy, Harley Moon, and Alison O'Brien, "Passive Protection of Suckling Piglets From *Escherichia coli* O157:H7 Infection by Vaccination of Pregnant Sows with intimin$_{O157}$," 4$^{th}$ International Shiga Toxin Producing E. coli Meeting, Kyoto, Japan (Oct. 2000).

Beebakhee et al., "Cloning and Nucleotide Sequence of the eae Gene Homologue from Enterohemorrhagic *Escherichia coli* Serotype 0157:H7", FEMS Microbio. Ltrs, 91:63–68 (1992).

Dalsgaard et al., "Plant–Derived Vaccine Protects Target Animals Against a Viral Disease", Nature Biotechnology, 15:248–252 (1997).

Donnenberg et al., "The Role of the eae Gene of Enterohemorrhagic *Escherichia coli* in Intimate Attachment In Vitro and in a Porcine Model", J. Clin. Invest., 92:1418–1424 (Sep. 1993).

Frankel et al., "Characterization of the C–Terminal Domains of Intimin–Like Proteins of Enteropathogenic and Enterohemorrhagic *Escherichia coli*, *Citrobacter*, and *Hafnia alvei*", Infection and Immunity, 62(5):1835–1842 (May 1994).

Frankel et al., "Molecular Characterization of a Carboxy–Terminal Eukaryotic–Cell–Binding Domain of Intimin from Enteropthogenic *Escherichia coli*", Infection and Immunity, 63(11):4323–4328 (Nov. 1995).

Hochuli, "Purification of Recombinant Proteins with Metal Chelate Adsorbent", Genetic Engineering, Principles & Practice (J. Setlow, ed) Plenum, New York, 12:87–98 (1990).

Jerse and Kaper, "The eae Gene of Enteropathogenic *Escherichia coli* Encodes a 94–Kilodalton Membrane Protein, the Expression of Which is Influenced by the EAF Plasmid", Infection and Immunity, 59(12):4302–4309 (Dec. 1991).

Levine et al., "The Diarrheal Response of Humans to Some Classic Serotypes of Enteropathogenic *Escherichia coli* is Dependent on a Plasmid Encoding an .Enteroadhesiveness Factor", J. Infect. Dis., 152(3):550–559 (Sep. 1985).

Little et al., "Human Antibody Libraries in *Escherichia coli*", J. Biotech, 41:187–195 (1995).

Louie et al., "Expression and Characterization of the eaeA Gene Product of *Escherichia coli* Serotype 0157:H7", Infection and Immunity,61(10):4085–4092 (Oct. 1993).

McKee and O'Brien, "Truncated Enterohemorrhagic *Escherichia coli* (EHEC) 0157:H7 Intimin (EaeA) Fusion Proteins Promote Adherence of EHEC Strains to HEp–2 Cells", Infection and Immunity, 64(6):2225–2233 (Jun. 1996).

McKee et al., "Enterohemorrhagic *Escherichia coli* 0157:H7 Requires Intimin to Colonize the Gnotobiotic Pig Instestine and to Adhere to HEp–2 Cells", Infection and Immunity, 63(9):3739–3744 (Sep. 1995).

McKee and O'Brien, "Investigation of Enterohemorrhagic *Escherichia coli* 0157:H7 Adherence Characteristics and Invasion Potential Reveals a New Attachment Pattern Shared by Intestinal E. coli", Infection and Immunity, 63(5):2070–2074 (May 1995).

Skerra, "Bacterial Expression of Immunoglobulin Fragments," Current Opinion in Immunology, 5:256–262 (1993).

Yu and Kaper, "Cloning and Characterization of the eae Gene of Enterohaemorrhagic *Escherichia coli* 0157:H7", Molecular Biology, 6(3):411–417 (1992).

McKee and O'Brien, Abstract B–5, Abstracts of the 95th General Meeting of the American Society for Microbiology (Abstracts sent out Apr. 21, 1995).

Database DISSABS an 95:64682 (1995) McKee, M.L. "Adherence of Enterohemorrhagic *Escherichia coli* to Human Epithelial Cells: The Role of Intimin (Bloody Diarrhea, Renal Failure, Hemorrhagic Colitis)" XP002040904, Abstract: McKee, M.L., Dissertation 1995, Available Dissertation Abstracts International Order No.: AAI9540040.

International Search Report of International Application No. PCT/US97/05832.

O'Brien et al., "Intimin: Candidate for an *Escherichia coli* 0157:H7 Anti–Transmission Vaccine", Abstracts: Thirty Second Conference on Cholera and Related Diarrheal Diseases, Nagaasaki University Pompe Hall (Nov. 14–16, 1996).

English Abstract of European Patent Application No. 0282042.

* cited by examiner

| | | | | | |
|---|---|---|---|---|---|
| 1 | MITHGCYTRT | RHKHKLKKTL | IMLSAGLGLF | FYVNQNSFAN | GENYFKLGSD |
| 51 | SKLLTHDSYQ | NRLFYTLKTG | ETVADLSKSQ | DINLSTIWSL | NKHLYSSESE |
| 101 | MMKAAPGQQI | ILPLKKLPFE | YSALPLLGSA | PLVAAGGVAG | HTNKLTKMSP |
| 151 | DVTKSNMTDD | KALNYAAQQA | ASLGSQLQSR | SLNGDYAKDT | ALGIAGNQAS |
| 201 | SQLQAWLQHY | GTAEVNLQSG | DNFDGSSLDF | LLPFYDSEKM | LAFGQVGARY |
| 251 | IDSRFTANLG | AGQRFFLPAN | MLGYNVFIDQ | DFSGDNTRLG | IGGEYWRDYF |
| 301 | KSSVNGYFRM | RRWHESYHKK | DYDERPANGF | DIRFNGYLPS | YPALGAKLIY |
| 351 | EQYYGDNVAL | FNSDKLQSNP | GAATVGVNYT | PIPLVTMGID | YRHGTGNEND |
| 401 | LLYSMQFRYQ | FDKSWSQQIE | PQYVNELRTL | SGSRYDLVQR | NNNIILEYKK |
| 451 | QDILSLNIPH | DINGTEHSTQ | KIQLIVKSKY | GLDRIVWDDS | ALRSQGGQIQ |
| 501 | HSGSQSAQDY | QAILPAYVQG | GSNIYKVTAR | AYDRNGNSSN | NVQLTITVLS |
| 551 | NGQVVDQVGV | TDFTADKTSA | KADNADTITY | TATVKKNGVA | QANVPVSFNI |
| 601 | VSGTATLGAN | SAKTDANGKA | TVTLKSSTPG | QVVVSAKTAE | MSSALNASAV |
| 651 | IFFDQTKASI | TEIKADKTTA | VANGKDAIKY | TVKVMKNGQP | VNNQSVTFST |
| 701 | NFGMFNGKSQ | TQATTGNDGR | ATITLTSSSA | GKATVSATVS | DGAEVKATEV |
| 751 | TFFDELKIDN | KVDIIGNNVR | GELPNIWLQY | GQFKLKASGG | DGTYSWYSEN |
| 801 | TSIATVDASG | KVTLNGKGSV | VIKATSGDKQ | TVSYTIKAPS | YMIKVDKQAY |
| 851 | YADAMSICKN | LLPSTQTVLS | DIYDSWGAAN | KYSHYSSMNS | ITAWIKQTSS |
| 901 | EQRSGVSSTY | NLITQNPLPG | VNVNTPNVYA | VCVE (SEQ ID NO:19) | |

FIG. 2

```
1     TCGAGAATGA AATAGAAGTC GTTGTTAAGT CAATGGAAAA CCTGTATTTG GTATTACATA
61    ATCAGGGAAT AACATTAGAA AACGAACATA TGAAAATAGA GGAAATCAGT TCAAGCGACA
121   ATAAACATTA TTACGCCGGA AGATAAAATC CGATCTATTA ATATAATTTA TTTCTCATTC
181   TAACTCATTG TGGTGGAGCC ATAACATGAT TACTCATGGT TGTTATACCC GGACCCGGCA
241   CAAGCATAAG CTAAAAAAAA CATTGATTAT GCTTAGTGCT GGTTTAGGAT TGTTTTTTTA
301   TGTTAATCAG AATTCATTTG CAAATGGTGA AAATTATTTT AAATTGGGTT CGGATTCAAA
361   ACTGTTAACT CATGATAGCT ATCAGAATCG CCTTTTTTAT ACGTTGAAAA CTGGTGAAAC
421   TGTTGCCGAT CTTTCTAAAT CGCAAGATAT TAATTTATCG ACGATTTGGT CGTTGAATAA
481   GCATTTATAC AGTTCTGAAA GCGAAATGAT GAAGGCCGCG CCTGGTCAGC AGATCATTTT
541   GCCACTCAAA AAACTTCCCT TTGAATACAG TGCACTACCA CTTTTAGGTT CGGCACCTCT
601   TGTTGCTGCA GGTGGTGTTG CTGGTCACAC GAATAAACTG ACTAAAATGT CCCCGGACGT
661   GACCAAAAGC AACATGACCG ATGACAAGGC ATTAAATTAT GCGGCACAAC AGGCGGCGAG
721   TCTCGGTAGC CAGCTTCAGT CGCGATCTCT GAACGGCGAT TACGCGAAAG ATACCGCTCT
781   TGGTATCGCT GGTAACCAGG CTTCGTCACA GTTGCAGGCC TGGTTACAAC ATTATGGAAC
841   GGCAGAGGTT AATCTGCAGA GTGGTAATAA CTTTGACGGT AGTTCACTGG ACTTCTTATT
901   ACCGTTCTAT GATTCCGAAA AAATGCTGGC ATTTGGTCAG GTCGGAGCGC GTTACATTGA
961   CTCCCGCTTT ACGGCAAATT TAGGTGCGGG TCAGCGTTTT TTCCTTCCTG CAAACATGTT
1021  GGGCTATAAC GTCTTCATTG ATCAGGATTT TTCTGGTGAT AATACCCGTT TAGGTATTGG
1081  TGGCGAATAC TGGCGAGACT ATTTCAAAAG TAGCGTTAAC GGCTATTTCC GCATGAGCGG
1141  CTGGCATGAG TCATACAATA AGAAAGACTA TGATGAGCGC CAGCAAATG GCTTCGATAT
1201  CCGTTTTAAT GGCTATCTAC CGTCATATCC GGCATTAGGC GCCAAGCTGA TATATGAGCA
1261  GTATTATGGT GATAATGTTG CTTTGTTTAA TTCTGATAAG CTGCAGTCGA ATCCTGGTGC
1321  GGCGACCGTT GGTGTAAACT ATACTCCGAT TCCTCTGGTG ACGATGGGGA TCGATTACCG
1381  TCATGGTACG GGTAATGAAA ATGATCTCCT TTACTCAATG CAGTTCCGTT ATCAGTTTGA
1441  TAAATCGTGG TCTCAGCAAA TTGAACCACA GTATGTTAAC GAGTTAAGAA CATTATCAGG
1501  CAGCCGTTAC GATCTGGTTC AGCGTAATAA CAATATTATT CTGGAGTACA AGAAGCAGGA
1561  TATTCTTTCT CTGAATATTC CGCATGATAT TAATGGTACT GAACACAGTA CGCAGAAGAT
1621  TCAGTTGATC GTTAAGAGCA AATACGGTCT GGATCGTATC GTCTGGGATG ATAGTGCATT
1681  ACGCAGTCAG GGCGGTCAGA TTCAGCATAG CGGAAGCCAA AGCGCACAAG ACTACCAGGC
1741  TATTTTGCCT GCTTATGTGC AAGGTGGCAG CAATATTTAT AAAGTGACGG CTCGCGCCTA
1801  TGACCGTAAT GGCAATAGCT CTAACAATGT ACAGCTTACT ATTACCGTTC TGTCGAATGG
1861  TCAAGTTGTC GACCAGGTTG GGGTAACGGA CTTTACGGCG ATAAGACTT CGGCTAAAGC
1921  GGATAACGCC GATACCATTA CTTATACCGC GACGGTGAAA AAGAATGGGG TAGCTCAGGC
1981  TAATGTCCCT GTTTCATTTA ATATTGTTTC AGGAACTGCA ACTCTTGGGG CAAATAGTGC
2041  CAAAACGGAT GCTAACGGTA AGGCAACCGT AACGTTGAAG TCGAGTACGC AGGACAGGT
2101  CGTCGTGTCT GCTAAAACCG CGGAGATGAC TTCAGCACTT AATGCCAGTG CGGTTATATT
2161  TTTTGATCAA ACCAAGGCCA GCATTACTGA GATTAAGGCT GATAAGACAA CTGCAGTAGC
2221  AAATGGTAAG GATGCTATTA ATATACTGT AAAAGTTATG AAAAACGGTC AGCCAGTTAA
2281  TAATCAATCC GTTACATTCT CAACAAACTT TGGGATGTTC AACGGTAAGT CTCAAACGCA
2341  AGCAACCACG GGAAATGATG GTCGTGCGAC GATAACACTA ACTTCCAGTT CCGCCGGTAA
2401  AGCGACTGTT AGTGCGACAG TCAGTGATGG GGCTGAGGTT AAAGCGACTG AGGTCACTTT
2461  TTTTGATGAA CTGAAAATTG ACAACAAGGT TGATATTATT GGTAACAATG TCAAGAGGTC
2521  GATGTTGCCT AATATTTGGC TGCAATATGG TCAGTTTAAA CTGAAAGCAA GCGGTGGTGA
2581  TGGTACATAT TCATGGTATT CAGAAAATAC CAGTATCGCG ACTGTCGATG CATCAGGGAA
2641  AGTCACTTTG AATGGTAAAG GCAGTGTCGT AATTAAAGCC ACATCTGGTG ATAAGCAAAC
2701  AGTAAGTTAC ACTATAAAAG CACCGTCGTA TATGATAAAA GTGGATAAGC AAGCCTATTA
2761  TGCTGATGCT ATGTCCATTT GCAAAAATTT ATTACCATCC ACACAGACGG TATTGTCAGA
2821  TATTTATGAC TCATGGGGGG CTGCAAATAA ATATAGCCAT TATAGTTCTA TGAACTCAAT
2881  AACTGCTTGG ATTAAACAGA CATCTAGTGA GCAGCGTTCT GGAGTATCAA GCACTTATAA
2941  CCTAATAACA CAAAACCCTC TTCCTGGGGT TAATGTTAAT ACTCCAAATG TCTATGCGGT
3001  TTGTGTAGAA TAATTCCATA ACCACCCCGG CTAAAATATG TATTGTTTTA GTCGGGGCAT
3061  AATTATTTCT TCTTAAGAAA TAACCCTCTT ATAATCAAAT CTACTACTGG TCTTTTTATC
3121  TGCTTAATAG G(SEQ ID NO:20)
```

FIG. 3

```
1     GGAAAGATAA ATCCGATCTA TTAATATAAT TTATTTCTCA TTCTAACTCA TTGTGGTGGA
61    GCCATAACAT GAGTACTCAT GGTTGTTATA CCCGGACCCG GCACAAGCAT AAGCTAAAAA
121   AAACATTGAT TATGCTTAGT GCTGGTTTAG GATTGTTTTT TTATGTTAAT CAGAATTCAT
181   TTGCAAATGG TGAAAATTAT TTTAAATTGG GTTCGGATTC AAAACTGTTA ACTCATGATA
241   GCTATCAGAA TCGCCTTTTT TATACGTTGA AAACTGGTGA AACTGTTGCC GATCTTTCTA
301   AATCGCAAGA TATTAATTTA TCGACGATTT GGTCGTTGAA TAAGCATTTA TACAGTTCTG
361   AAAGCGAAAT GATGAAGGCC GCGCCTGGTC AGCAGATCAT TTTGCCACTC AAAAAACTTC
421   CCTTTGAATA CAGTGCACTA CCACTTTTAG GTTCGGCACC TCTTGTTGCT GCAGGTGGTG
481   TTGCTGGTCA CACGAATAAA CTGACTAAAA TGTCCCCGGA CGTGACCAAA AGCAACATGA
541   CCGATGACAA GGCATTAAAT TATGCGGCAC AACAGGCGGC GAGTCTCGGT AGCCAGCTTC
601   AGTCGCGATC TCTGAACGGC GATTACGCGA AGATACCGC TCTTGGTATC GCTGGTAACC
661   AGGCTTCGTC ACAGTTGCAG GCCTGGTTAC AACATTATGG AACGGCAGAG GTTAATCTGC
721   AGAGTGGTGA TAACTTTGAC GGTAGTTCAC TGGACTTCTT ATTACCGTTC TATGATTCCG
781   AAAAAATGCT GGCATTTGGT CAGGTCGGAG CGCGTTACAT TGACTCCGC TTTACGGCAA
841   ATTTAGGTGC GGGTCAGCGT TTTTTCCTTC CTGCAAACAT GTTGGGCTAT AACGTCTTCA
901   TTGATCAGGA TTTTTCTGGT GATAATACCC GTTTAGGTAT TGGTGGCGAA TACTGGCGAG
961   ACTATTTCAA AAGTAGCGTT AACGGCTATT TCCGCATGAG CGCTGGCAT GAGTCATACC
1021  ATAAGAAAGA CTATGATGAG CGCCCAGCAA ATGGCTTCGA TATCCGTTTT AATGGCTATC
1081  TACCGTCATA TCCGGCATTA GGCGCCAAGC TGATATATGA GCAGTATTAT GGTGATAATG
1141  TTGCTTTGTT TAATTCTGAT AAGCTGCAGT CGAATCCTGG TGCGGCGACC GTTGGTGTAA
1201  ACTATACTCC GATTCCTCTG GTGACGATGG GGATCGATTA CCGTCATGGT ACGGGTAATG
1261  AAAATGATCT CCTTTACTCA ATGCAGTTCC GTTATCAGTT TGATAAATCG TGGTCTCAGC
1321  AAATTGAACC ACAGTATGTT AACGAGTTAA GAACATTATC AGGCAGCCGT TACGATCTGG
1381  TTCAGCGTAA TAACAATATT ATTCTGGAGT ACAAGAAGCA GGATATTCTT TCTCTGAATA
1441  TTCCGCATGA TATTAATGGT ACTGAACACA GTACGCAGAA GATTCAGTTG ATCGTTAAGA
1501  GCAAATACGG TCTGGATCGT ATCGTCTGGG ATGATAGTGC ATTACGCAGT CAGGGCGGTC
1561  AGATTCAGCA TAGCGGAAGC CAAAGCGCAC AAGACTACCA GGCTATTTTG CCTGCTTATG
1621  TGCAAGGTGG CAGCAATATT TATAAAGTGA CGGCTCGCGC CTATGACCGT AATGGCAATA
1681  GCTCTAACAA TGTACAGCTT ACTATTACCG TTCTGTCGAA TGGTCAAGTT GTCGACCAGG
1741  TTGGGGTAAC GGACTTTACG GCGGATAAGA CTTCGGCTAA AGCGGATAAC GCCGATACCA
1801  TTACTTATAC CGCGACGGTG AAAAAGAATG GGGTAGCTCA GGCTAATGTC CCTGTTTCAT
1861  TTAATATTGT TTCAGGAACT GCAACTCTTG GGCAAATAG TGCCAAAACG GATGCTAACG
1921  GTAAGGCAAC CGTAACGTTG AAGTCGAGTA CGCCAGGACA GGTCGTCGTG TCTGCTAAAA
1981  CCGCGGAGAT GAGTTCAGCA CTTAATGCCA GTGCGGTTAT ATTTTTTGAT CAAACCAAGG
2041  CCAGCATTAC TGAGATTAAG GCTGATAAGA CAACTGCAGT AGCAAATGGT AAGGATGCTA
2101  TTAAATATAC TGTAAAAGTT ATGAAAAACG GTCAGCCAGT TAATAATCAA TCCGTTACAT
2161  TCTCAACAAA CTTTGGGATG TTCAACGGTA AGTCTCAAAC GCAAGCAACC ACGGGAAATG
2221  ATGGTCGTGC GACGATAACA CTAACTTCCA GTTCCGCCGG TAAAGCGACT GTTAGTGCGA
2281  CAGTCAGTGA TGGGGCTGAG GTTAAAGCGA CTGAGGTCAC TTTTTTTGAT GAACTGAAAA
2341  TTGACAACAA GGTTGATATT ATTGGTAACA ATGTCAGAGG CGAGTTGCCT AATATTTGGC
2401  TGCAATATGG TCAGTTTAAA CTGAAAGCAA GCGGTGGTGA TGGTACATAT TCATGGTATT
2461  CAGAAAATAC CAGTATCGCG ACTGTCGATG CATCAGGGAA AGTCACTTTG AATGGTAAAG
2521  GCAGTGTCGT AATTAAAGCC ACATCTGGTG ATAAGCAAAC AGTAAGTTAC ACTATAAAAG
2581  CACCGTCGTA TATGATAAAA GTGGATAAGC AAGCCTATTA TGCTGATGCT ATGTCCATTT
2641  GCAAAAATTT ATTACCATCC ACACAGACGG TATTGTCAGA TATTTATGAC TCATGGGGGG
2701  CTGCAAATAA ATATAGCCAT TATAGTTCTA TGAACTCAAT AACTGCTTGG ATTAAACAGA
2761  CATCTAGTGA GCAGCGTTCT GGAGTATCAA GCACTTATAA CCTAATAACA CAAAACCCTC
2821  TTCCTGGGGT TAATGTTAAT ACTCCAAATG TCTATGCGGT TTGTGTAGAA TAATTCCATA
2881  ACCACCCCGG CTAAAATATG TATTGTTTTA GTCGGGGCAT AATTATTTCT TCTTAAGAAA
2941  TAACCTCTTA TAATCAAATC TACTACTGGT CTTTTATCT GCTTAATAGG TCTCTTTCAA
3001  AGAGACACAT TCACGTTTTC TAGAGTAGGT TGATCCAACC ACGCTGTATA CCAAAGCTGA
3061  ATCACATCAA GCAACAACTA TGCTCACAAC ATCCACACAA TAAAAA (SEQ ID NO:21)
```

FIG. 4

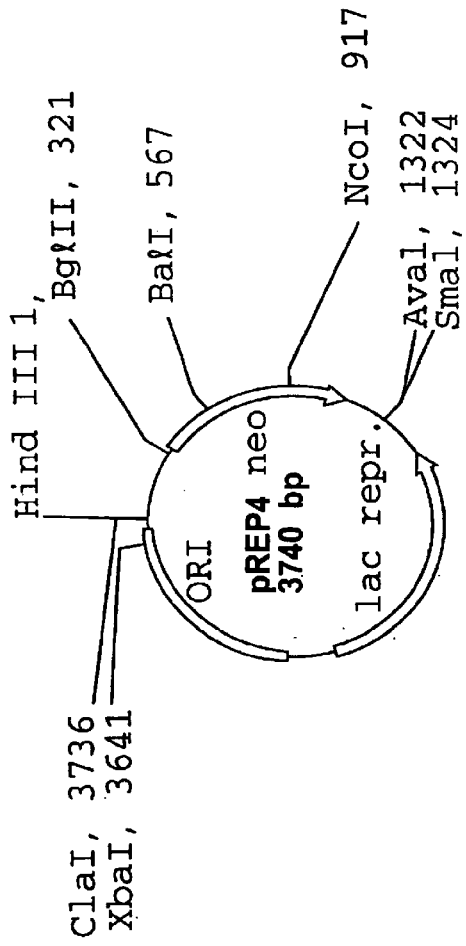

FIG. 9

```
       XhoI                                        operatorI
  1 CTCGAGAAAT CATAAAAAAT TTATTTGCTT TGTGAGCGGA TAACAATTAT
                                                  TATA-Box operator II              EcoRI
 51 AATAGATTCA ATTGTGAGCG GATAACAATT TCACACAGAA TTCATTAAAG
                ↑ +1 start mRNA
                  ATG →

6xHis
101 AGGAGAAATT AACTATGAGA GGATCGCATC ACCATCACCA TCACGGATCC
    RBS/SD                                            BamHI

151 GCATGCGAGC TCGGTACCCC GGGTCGACCT GCAGCCAAGC TTAATTAGCT
    SphI  SacI  KpnI  SmaI  SalI  PstI  HindIII
                                                  Stop 1 2 3

201 GAGCTTGGAC TCCTGTTGAT AGATCCAGTA ATGACCTCAG AACTCCATCT (SEQ ID NO:25)
```

HISTIDINE-TAGGED INTIMIN AND METHODS OF USING INTIMIN TO STIMULATE AN IMMUNE RESPONSE AND AS AN ANTIGEN CARRIER WITH TARGETING CAPABILITY

This application claims priority to Provisional Application Ser. No. 60/015,657, filed Apr. 19, 1996, and Provisional Application Ser. No. 60/015,936, filed Apr. 22, 1996.

GOVERNMENT INTEREST

The invention described herein may be manufactured, licensed and used for governmental purposes without the payment of any royalties to us thereon.

FIELD OF THE INVENTION

This invention relates to an isolated, functional bacterial protein, intimin, and its use as an antigen for protecting against infection by or transmission of bacteria expressing intimin-like proteins, such as certain pathogenic strains of Escherichia coli. The invention also relates to the use of intimin as a means for promoting an immune response to other antigens, and as a means of targeting delivery of antigens or medication to specific cells or locations within the body. The invention also relates to antibodies, both polyclonal and monoclonal, and their use in the treatment, diagnosis and prevention of infections by pathogenic E. coli.

BACKGROUND OF THE INVENTION

A virulent form of bloody diarrhea is caused by the Enterohemorrhagic Escherichia coil (EHEC). This pathogen is the most common infectious cause of bloody diarrhea (also called hemorrhagic colitis [HC]) in the United States (Centers for Disease Control and Prevention (executive summary). MMWR. 43(No.RR-5):1–18 (1994; Griffin, P. M. et al. Annals of Internal Med. 109:705 (1988). One serotype in particular, 0157:H7, is the most commonly isolated serotype of EHEC in the United States, and has been linked to a significant number of outbreaks of HC beginning in 1982 (Riley, L. W. et al. N.Eng.J. Med. 308:681 (1983)).

The primary mode of transmission of EHEC occurs through ingestion of contaminated food, particularly undercooked hamburger (Doyle, M. P. and Schoeni, J. L. Appl. Environ. Microbiol. 53:2394 (1987); Samadpour, M. et al. Appl. Environ. Microbiol. 60:1038 (1994)). Among people infected by EHEC, as many as 5–10% suffer a serious complication called Hemolytic Uremic Syndrome (HUS), a condition caused by the action of Shiga-like toxins that target and destroy cells lining blood vessels (endothelial cells), such as those present in the glomeruli of the kidney. (Johnson, W. M. et al. Lancet. i:76 (1983); O'Brien, A. D. et al. Lancet. i:702 (1983)). HUS can result in permanent kidney damage or even complete kidney failure.

Although EHEC can cause very serious illness even in healthy adults, young children in particular are at greater risk of dying or suffering permanent damage from the infection. Others for whom the infection can be particularly dangerous include the elderly and immuno-compromised. With the prevalence of EHEC in cattle and the subjective nature of differentiating between cooked and undercooked hamburger, a convenient stop at a fast food restaurant, or even a family barbecue, can result in family tragedy.

One key to the deadly nature of EHEC is the bacteria's ability to produce attaching/effacing (A/E) intestinal lesions in the colon, such as those demonstrated in gnotobiotic pigs (Tzipori, S. et al. Infect. Immun. 57:1142 (1989)). The A/E lesions demonstrated in pigs are characterized by intimate bacterial adherence to the mucosal cells of the intestinal lining and dissolution of microvilli (McKee, M. L. et al. Infect. Immun. 63:3739 (1995); Tzipori, S. et al. Infect. Immun. 57:1142 (1989)). Similar lesions have been seen in human laryngeal epithelial (HEp-2)(ATCC # CCL23) cells in tissue culture (McKee, M. L. et al. Infect. Immun. 63:3739 (1995); Tzipori, S. et al. Infect. Immun. 57:1142 (1989).

In 1990, Jerse et al. identified a chromosomal gene in a related diarrheagenic E. coli strain, Enteropathogenic E. coli (EPEC). That gene, designated eae (formerly known as eaeA), was found to be required for the bacterium to produce A/E lesions in tissue culture (Jerse, A. E. et al. Proc. Natl. Acad. Sci. USA. 87:7839 (1990)). The eae gene encoded a 94 kDa outer membrane protein (intimin), called eae, which is the intimin of EPEC. A similar protein was demonstrated to be present in an EHEC 0157:H7 strain (Jerse, A. E. and Kaper, J. B. Infect. Immun. 59:4302 (1991)).

Recently, investigators demonstrated that intimin is necessary for adherence of EHEC to human epithelial laryngeal (HEp-2) cells and human ileocecal epithelial (HCT-8) cells (ATCC # CCL244) (McKee, M. L. et al. Infect. Immun. 63:3739 (1995)) and for formation of A/E lesions in the piglet intestine (Donnenberg, M. S. et al. J. Clin. Invest. 92:1418 (1993); McKee, M. L. et al. Infect. Immun. 63:3739 (1995)). Although human studies with EHEC have not been conducted, as they are unethical and forbidden, the intimin protein found in EPEC is strongly associated with the production of diarrhea and fever in human volunteers (Donnenberg, M. S. et al. J. Clin. Invest. 92:1412 (1993); Levine, M. M. et al. J. Infect. Dis. 152:550 (1985)).

Human volunteers (10 out of 10) challenged with EPEC strain E2348/69 mounted a notable immune response to the 94 kDa protein after 28 days (Levine et al. J Infect. Dis. 152:550 (1985)). In these human trials the only volunteer (1 out of 10) who failed to develop diarrhea after ingestion of E2348/69 was the individual in this group who had detectable antibody to the 94 kDa protein intimin before challenge.

Two other bacterial species capable of inducing A/E lesions have been shown to contain the eae locus: Hafnia alvei (Albert, M. J. et al. J. Med. Microbiol. 37:310 (1992)) and Citrobacter rodentium (formerly known as Citrobacter freundii biotype 4280) (Schauer, D. B., and Falkow, S. Infect. Immun. 61:2486 (1993)). Although these bacteria are not generally associated with pathology in humans, they can cause significant disease in the animal species with which they are normally associated. For instance, Citrobacter rodentium is associated with gastrointestinal illness in mice. Mice often serve as control and test subjects in experiments. Costly and carefully controlled experiments can be jeopardized by an outbreak of this disease in an animal care facility. In addition, such bacterial species may become pathogenic to immuno-compromised patients, the young and the elderly.

The pathogens Yersina enterocolitic and Yersina pseudotuberculosis express a 103 kDa outer membrane protein (invasin) that allows bacterial penetration of cultured epithelial cells (Isberg, R. R. et al., Cell 60: 769 et seq. (9187)) and efficient penetration of the intestinal epithelium in vivo (Pepe, J. C. and Miller, V. L., Proc. Natl. Acad. Sci. USA 90:6473 et seq. (1993)). Invasin is also a member of the intimin protein family.

Animals, such as cows, infected with bacterial strains expressing intimin may become ill themselves, in addition to serving as a source of such infections to others. Eradicating or even limiting these animal reservoirs of intimin-expressing bacteria in animals with antibiotic therapy would be prohibitively expensive. In addition, not only is antibiotic treatment of the infections in humans or animals costly, but the antibiotics themselves are associated with side effects that can be dangerous. As with EHEC, those side effects can be especially dangerous to young children and the elderly. Consequently, the need exists for another means of reducing the seriousness of the infections or preventing them altogether through promotion of protective immune responses against bacteria expressing intimin.

A further need is for forms of immunization that are less time consuming, expensive and painful than immunization through injection of antigens. Yet another need is for the generation of protective immune responses in the specific tissues involved at the point of infection, most often the gastrointestinal mucosa.

Other organisms infecting gastrointestinal tissue, including, but not limited to *Salmonella sp.* and *Shigella sp.*, possess antigens against which an immune response could be generated. A need exists, however, for a means of targeting those antigens to gastrointestinal mucosa, in order to stimulate a mucosal immune response, as well as stimulating circulating antibodies.

Immuno-compromised individuals are less able to mount a protective immune response against pathogens, even with prior exposure to antigens associated with the pathogens. Thus a need exists to provide passive immune protection to immunocompromised individuals exposed to the pathogens. A related need is the ability to identify whether an infection may be protected against by the presence of antibodies to intimin.

SUMMARY OF THE INVENTION

The present invention relates to an enriched protein comprising intimin or a portion of intimin that retains wild-type binding activity or that induces antibodies that block wild-type binding activity, as well as to a purified protein comprising intimin or a portion of intimin that retains wild-type binding activity or that induces antibodies that block wild-type binding activity. The invention also relates to a protein, comprising intimin, an intimin-like protein, or portion thereof, having a histidine tag. The invention further relates to the above-described proteins where the intimin, intimin-like protein, or portion thereof further comprises at least one antigen, at least one drug or a combination thereof chemically, physically or recombinantly conjugated with the intimin, intimin-like protein, or portion thereof.

Additionally, the present invention relates to a method for making purified intimin or a purified portion of intimin retaining binding activity, comprising expressing a protein comprising intimin having a histidine tag or a portion of intimin having a histidine tag, and removing the histidine tag from the intimin or portion of intimin. The invention further relates to a method for making a purified intimin-like protein or a portion thereof, comprising expressing a protein comprising an intimin-like protein, or a portion thereof, having a histidine tag, and removing the histidine tag from the intimin-like protein, or portion thereof, before or after the purification.

The invention still further relates to a method for making enriched intimin or an enriched portion of intimin, comprising expressing a protein comprising intimin having a histidine tag or a portion of intimin having a histidine tag, enriching the intimin or portion of intimin, and optionally removing the histidine tag from the enriched intimin or enriched portion of intimin. The invention similarly relates to a method for making an enriched intimin-like protein or portion thereof, comprising expressing a protein comprising an intimin-like protein, or portion thereof, having a histidine tag, enriching the intimin-like protein or portion thereof, and optionally removing the histidine tag from the enriched intimin-like protein or portion thereof.

The invention also relates to a method of promoting a protective immune response against bacteria expressing intimin or intimin-like proteins, comprising administering to a patient intimin, an intimin-like protein, or portion thereof, wherein said portion retains wild-type binding activity or induces antibodies that block wild-type binding activity.

The invention additionally relates to a method of promoting a protective immune response against at least one antigen comprising administering to a patient a composition comprising at least one antigen chemically, physically or recombinantly conjugated to intimin, to an intimin-like protein, or to a portion thereof.

The invention further relates to a method of targeting the delivery of at least one antigen, at least one drug, or a combination thereof to epithelial cells, comprising administering to a patient a composition comprising at least one antigen, at least one drug or a combination thereof, conjugated to intimin, to an intimin-like protein, or to a portion thereof having the ability to retain binding activity.

The invention still further relates to a method of providing passive immune protection comprising administering anti-intimin antibodies to a patient in need thereof.

The invention even further relates to a composition comprising anti-intimin antibodies, wherein the composition is free of other antibodies specific for an intimin-expressing host bacteria.

The invention even further yet relates to a method of preparing anti-intimin antibodies comprising expressing intimin having a histidine tag or a portion of intimin having a histidine tag, administering the intimin or portion of intimin to a patient, and recovering anti-intimin antibodies. The invention similarly relates to a method of preparing anti-intimin antibodies comprising expressing an intimin-like protein or portion thereof having a histidine tag, administering the intimin-like protein, or portion thereof, to a patient, and recovering anti-intimin antibodies.

BRIEF DESCRIPTION OF THE DRAWINGS

FIG. 2 depicts the predicted protein sequence of the complete EHEC 933 eae gene.

FIG. 3 depicts the DNA sequence from EHEC strain CL8, sequenced by Beebakhee, G. et al.

FIG. 4 depicts the DNA sequence from EHEC strain 933, sequenced by Yu and Kaper.

FIG. 9 depicts the repressor plasmid (Qiagen Inc.) (multicopy).

DETAILED DESCRIPTION OF THE INVENTION

Figure 1:
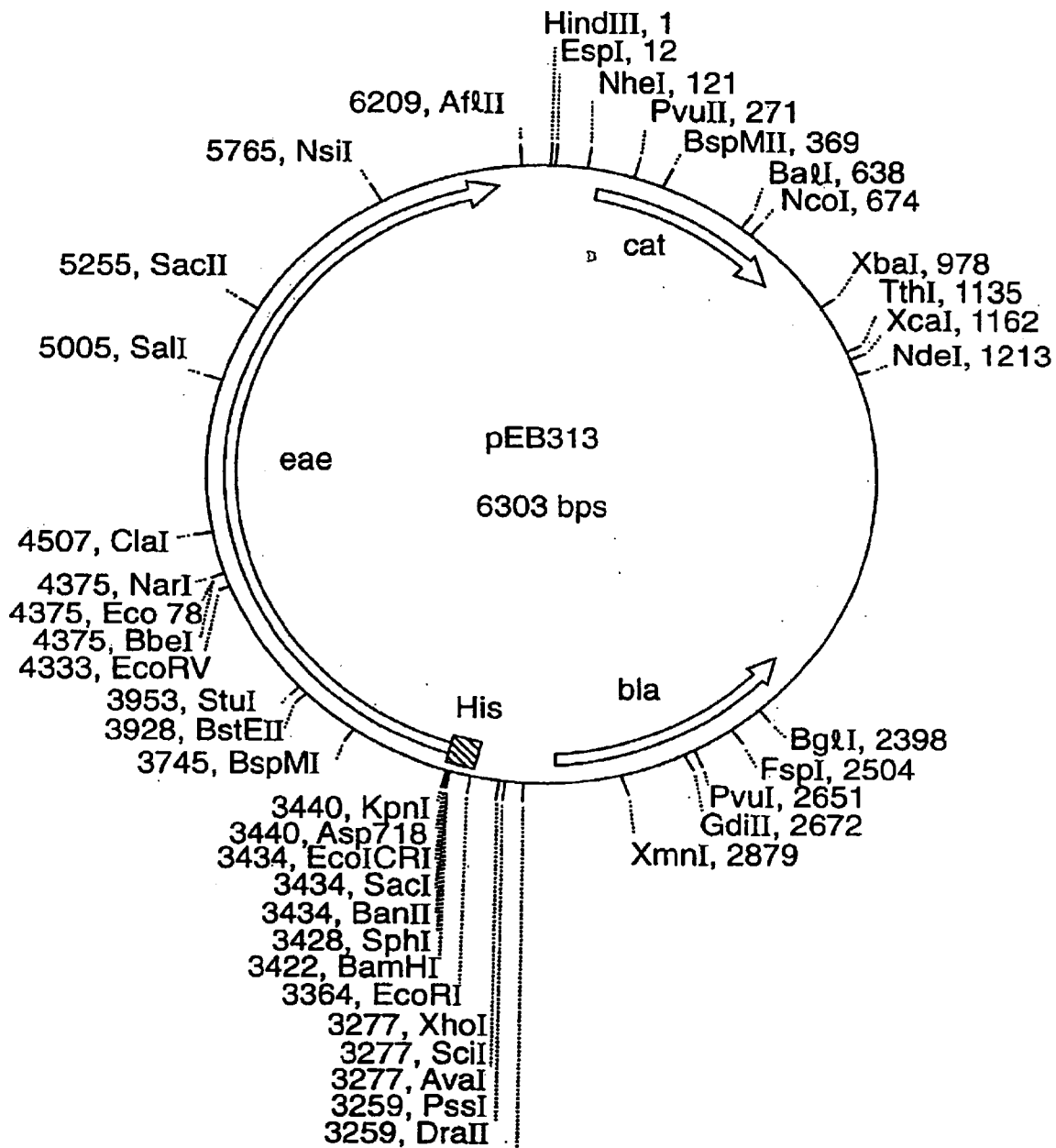
FIG. 1 depicts pEB313, a plasmid encoding RlHisEae. This plasmid encodes a histidine-tagged intimin that spans 900 out of 935 predicted C-terminal amino acids.

The invention is directed to an enriched protein comprising intimin or a portion of intimin retaining wild-type binding activity or inducing antibodies that block wild-type binding activity, as well as to a purified protein comprising intimin or a portion of intimin retaining wild-type binding activity or inducing antibodies that block wild-type binding activity. The invention is also directed to a protein, comprising intimin, a portion of intimin, or an intimin-like protein, wherein the intimin, the portion of intimin, or intimin-like protein has a histidine tag. Preferably the histidine-tagged intimin, histidine-tagged portion of intimin, or histidine-tagged intimin-like protein is enriched or purified. It is also preferred that the proteins described above further comprise at least one antigen, at least one drug or a combination thereof chemically, physically or recombinantly conjugated with the intimin, the portion of intimin, or the intimin-like protein.

The invention additionally relates to a method for making purified intimin or a purified portion of intimin, comprising:

expressing a protein comprising intimin or a portion of intimin, wherein the intimin or portion of intimin has a histidine tag, purifying the intimin or the portion of intimin, and removing the histidine tag from the intimin or portion of intimin before or after the purification.

The invention similarly relates to a method for making a purified intimin-like protein, comprising expressing a protein comprising an intimin-like protein having a histidine tag, purifying the intimin-like protein, and removing the histidine tag from the intimin-like protein before or after the purification.

The invention further relates to a method for making purified intimin or an enriched portion of intimin, comprising:

expressing a protein comprising intimin having a histidine tag or a portion of intimin having a histidine tag, purifying the intimin or the portion of intimin, and removing the histidine tag from the purified intimin or enriched portion of intimin.

The invention similarly relates to a method for making an enriched intimin-like protein, comprising expressing a protein comprising an intimin-like protein having a histidine tag, enriching the intimin-like protein, and removing the histidine tag from the enriched intimin-like protein.

The invention even further relates to a method of promoting a protective immune response against bacteria expressing intimin or intimin-like proteins, comprising administering to a patient intimin, a portion of intimin retaining binding activity, or an intimin-like protein. Preferably the intimin, portion of intimin or intimin-like protein is purified or enriched. It is also preferred that the intimin, portion of intimin, or intimin-like protein has a histidine tag.

The invention still further relates to a method of promoting a protective immune response against at least one antigen comprising administering to a patient a composition comprising at least one antigen chemically, physically or recombinantly conjugated to intimin, to a portion of intimin, or to an intimin-like protein or portion thereof. Preferably the intimin, portion of intimin or intimin-like protein or portion thereof is purified or enriched. It is also preferred that the intimin, portion of intimin, or intimin-like protein or portion thereof has a histidine tag.

The invention even still further relates to a method of targeting the delivery of at least one antigen, at least one drug, or a combination thereof to epithelial cells, comprising administering to a patient a composition comprising at least one antigen, at least one drug or a combination thereof, conjugated to intimin, to a portion of intimin , or to an intimin-like protein or portion thereof. Preferably the intimin, portion of intimin or intimin-like protein or portion thereof is purified or enriched. It is also preferred that the intimin, portion of intimin, or intimin-like protein or portion thereof has a histidine tag.

The invention even further yet relates to a method of providing passive immune protection comprising administering anti-intimin antibodies to a patient in need thereof.

The invention additionally relates to a composition comprising anti-intimin antibodies, wherein the composition is free of other antibodies specific for an intimin-expressing host bacteria, which, as used herein, refers to any pathogenic or non-pathogenic bacteria expressing intimin, a portion of intimin, or an intimin-like protein or portion thereof encoded in the bacterial genome or in a plasmid. Preferably this host bacteria is EHEC. The antibodies produced by this method can be monoclonal antibodies or polyclonal antibodies. Preferably the antibodies produced by this method are affinity-purified.

The invention also relates to a method of preparing anti-intimin antibodies comprising expressing intimin having a histidine tag or a portion of intimin having a histidine tag, administering the intimin or portion of intimin to a patient, and recovering anti-intimin antibodies. This method can also include removing the histidine tag. Additionally, this method preferably comprises enriching intimin or said portion of intimin and more preferably comprises purifying the intimin or the portion of intimin.

The invention similarly relates to a method of preparing anti-intimin antibodies comprising expressing an intimin-like protein or portion thereof having a histidine tag, administering the intimin-like protein or portion thereof to a patient, and recovering anti-intimin antibodies. This method can also include removing the histidine tag. Additionally, this method preferably comprises enriching the intimin-like protein or portion thereof, and more preferably comprises purifying the intimin-like protein or portion thereof.

An object of the invention is to purify large quantities of intimin, preferably EHEC intimin, that retain the ability to bind epithelial cells. To achieve this object, a portion of eae was cloned into a Histidine-tag expression vector, expressed and purified. An additional object of this invention is to administer his-intimin as an antigen to elicit an immune response. The specific his-tagged intimin protein described above and those set forth in the examples below can be used for that purpose; however, those skilled in the art will recognize that a smaller fragment that retains binding function may also be desirable.

Those skilled in the art will also recognize that the size of the his-tagged intimin to be used may be varied according to the specific purpose for administering the intimin. For example, if the his-tagged intimin is to be conjugated with one or more antigens, a smaller fragment may be selected to enhance stability of the combined fusion product, although the use of a larger fragment is by no means precluded. The size or conformation of the other antigen and the location of its significant epitopes may indicate that a particular length of his-tagged intimin will bring the epitopes into close proximity to the mucosa. The desired size will also vary with the convenience of available restriction sites, in light of the materials and methods known to those of ordinary skill in the art. Consequently, the terms his-intimin and his-tagged intimin, as used herein, mean polypeptides containing at least 900 out of the 935 predicted C-terminal amino acids of intimin with a histidine tag (full-length intimin). The invention also includes smaller portions of the his-tagged protein that retain binding function.

Conjugates between his-tagged intimin and one or more antigens may be generated through recombinant technology to generate a fusion protein comprising intimin in a portion of intimin and an additional protein antigen. In addition, intimin may be chemically or physically conjugated to proteins, peptides, carbohydrates and other antigens by methods known to those skilled in the art. Methods of chemical conjugation are well known to those skilled in the art, and include, in part, coupling through available functional groups (such as amino, carboxyl, thio and aldehyde groups). See S. S. Wong, Chemistry of Protein Conjugate and Crosslinking CRC Press (1991); and Brenkeley et al. Brief Survey of Methods for Preparing Protein Conjugates With Dyes, Haptens and Cross-linking Agents, Bioconjugate Chemistry 3 #1 (January 1992).

The retention of binding function means that the intimin, intimin-like proteins, and/or portions thereof retain the capacity to bind to epithelial cells or cell lines, such as HEp-2 and HCT-8. Such binding may be measured using any standard technique in the art. For example, the binding may be visualized as bacterial microcolony formation by the microcolony assay (Frankel et al., Infect. Immun. 62(5):1835–1842 (1994)), by FAS, (florescence actin staining), or both (McKee and O'Brien, Infect. Immun. 63(5):2070–2074 (1995), the disclosures of which is incorporated by reference herein). Additionally, binding may be measured in vivo as a function of bacterial virulence or pathogenicity, or by post-mortem histological examination. Examples of each of the above methods for determining binding function are detailed in Examples below, including the adherence assay described in Example IV.

One of the objects of the invention is to administer intimin or portions thereof, or intimin-like proteins, or portions thereof, to protect against illness or disease caused by EHEC or other pathogens having the capacity to bind epithelial cells through proteins having some degree of homology with the specific intimin expressed by EHEC. The object is achieved through stimulation of immune response directed against intimin, thereby blocking the capability of EHEC and related pathogens to adhere to epithelial cells. Consequently, the term immunization is used in the application.

The intimin, or portions of intimin, intimin-like proteins or portions thereof, are preferably capable of eliciting antibodies that block the binding of the corresponding wild-type protein. These antibodies may be directed against the binding site itself, or may be directed against any other portion of the linear polypeptide such that the antibodies block binding through steric hinderence or conformational changes. Such interference may be visualized, for example, by the loss of the wild-type binding pattern in the in vitro bacterial adherence assay of Example IV.

The degree of protection will vary with the degree of homology with intimin as well as the unique attributes of the patient, particularly as different species will be treated. The precise degree of protection is unimportant to quantitate in practicing the invention for any particular pathogen.

In addition to stimulating an immune response that permits a patient to avoid infection altogether, immunization as used herein also means decreasing the ability of the pathogens to colonize the gastrointestinal tract and decreasing the severity of an infection, as measured by any of the following indicators: reduced incidences of death, HUS, or permanent kidney damage; decreased levels of toxins; reduced fluid loss; or other indicators of illness regularly used by those ordinarily skilled in the relevant art.

Unless specified otherwise, the uses and methods set forth herein are generally applicable to humans and animals. The term patient is used herein to mean both humans and animals, and animals are not limited to domesticated animals but also may include wildlife and laboratory animals as well.

Isolating and Purifying His-tagged Intimin

It has been shown that a His-intimin fusion, in which the N-terminal third of the molecule is deleted (RVHindHis), was capable of complementing adherence of a non-adherent EHEC eae mutant; i.e., restored binding capability to a strain of EHEC that lost its binding capability following genetic alterations that prevented expression of intimin. The pattern of adherence demonstrated in the restored binding was indistinguishable from that observed in wild-type strain 86-24 (McKee, M. L. and O'Brien, A. D. Infect. Immun. In press (1996)). Where measured by the microcolony assay, noted above, wild-type activity is identified as a punctate pattern with localized areas of intense staining.

Purification of the intimin protein, however, was difficult, in part because intimin is always associated with the outer membrane of EHEC. The majority of the overexpressed recombinant intimin remained associated with the bacterial membrane fraction, even after sonic disruption of the host bacterium and addition of mild detergent to the extraction buffer. The insolubility of the intimin protein, combined with the abundance of other native *E. coli* proteins in the 97 kDa range, made purification of the native protein difficult.

Attempts to make an intimin-maltose binding protein fusion (MBP) also were unsuccessful because the predicted protein product had deletions and rearrangements. An attempt by other investigators had shown a construct of MBP fusions to the C-terminal 280 amino acids of intimin, but the fusion did not confer EHEC-like binding function. The diffuse pattern of adherence conferred by the MBP-intimin fusion protein was clearly different from the pattern of EHEC binding to HEp-2 cells (Frankel, G. et al. Infect. Immun. 62:1835 (1994)).

One possible explanation for the failure to obtain a functional MBP-intimin fusion larger than 280 amino acids is that overexpression of a piece of eae greater than the last 280 amino acids is unstable, and thus prone to rearrangements, i.e. it may be impossible to isolate that clone because it is lethal or deleterious to the cell when expressed. Alternatively, overexpression of a piece of MBP-intimin fusion larger than 280 amino acids could plug up the bacterial membrane, which would be lethal to the cells.

After trying unsuccessfully to purify intimin using MBP, a fusion was created using the QIAexpressionist Kit of QIAGEN, Inc., which involves attaching a histidine tag to the protein. The histidine tag is small, non-immunogenic, and binds tightly to a nickel affinity matrix, which facilitates purification of large quantities of material for further studies. In addition, the expression system permits one to maintain tight control of expression of the His fusion proteins to prevent any possible lethal effects of the recombinant protein on the $E.$ $coli$ host strain as a result of overexpression of the protein. Example I describes the creation of such a fusion protein.

EXAMPLE I

A. Construction of a Plasmid, pEB313 (FIG. 1), Encoding His-tagged Intimin Encompassing 900 out of 935 Predicted Amino Acids (FIG. 2).

The eae gene is cloned from EHEC strain 86-24 (serotype 0157:H7), readily obtainable from Griffin, P. M. et al., Ann. Intern. Med. 109:705–712 (1988), or Phil Tarr (Children's Hospital and Medical Center, 4800 Sand Point Way NE, Seattle, Wash. 98105, 206-526-2521.) The DNA is extracted according to standard chromosomal prep techniques (Wilson, K. in Current Protocols in Molecular Biology, Ausubel, F. M. et al. (eds.) vol 1:2.4.1—"Preparation of Genomic DNA from Bacteria").

The gene is cloned using the polymerase chain reaction (PCR), a standard technique in the art, using primers designed from a composite of the 2 known EHEC eae sequences. Two primers are constructed: Sn20-CGTTGTTAAGTCAATGGAAAC (SEQ ID NO:1), a 5' primer, spanning bases 20–41 of the sequence from the strain CL8, which was sequenced by Beebakhee,G. et al. FEMS Microbiology. 91:63 (1992) (FIG. 3); and MM2-TCTAGAGAGAAAACGTGAATGTTGTCTCT (SEQ ID NO:2), a 3' primer, spanning bases 3061–3082 of the sequence from strain 933, sequenced by Yu, J. and Kaper, J. B. Mol. Microbiol. 6:411 (1992) (FIG. 4). MM2 was further designed to include an XbaI site at the 3' end.

The PCR reactions are performed using the AmpliTaq Kit, according to the instructions of the manufacturer, Perkin Elmer. The PCR amplification produces a 3144 bp fragment encoding the entire eae open reading frame (ORF) (FIG. 5, region designated eae) and includes 186 bp upstream. The PCR product is processed to create blunt ends and ligated into the EcoRV site of the vector PBRKS$^-$ (Schmitt et al., J. Bacteriol. 176:368–377 (1994)).

The gene is cloned in both directions to allow transcription from either $P_{lac}$ pEB311 (FIG. 6) and from $P_{T7}$ pEB310 (FIG. 7) under the appropriate conditions. The plasmids are transformed into host strain XL1BlueF'Tn5 $lacI_Q$, (available from QIAGEN, Inc., 9600 DeSoto Ave., Chatsworth, Calif. 91311, 1-800-362-7737). The recombinants are maintained under the constitutive control of the lac repressor, because the previous failed attempts to clone eae suggested that overexpression of eae might be lethal to the host *E. coli* strain. The lower copy number of pBRKS$^-$ vector, along with the control conferred by the lac repressor obviates these problems.

A his-tagged intimin plasmid is constructed by digesting pEB310 with EcoRI, filling in with Klenow fragment, digesting with HindIII, and isolating the resulting 2895 bp fragment. The DNA fragments are isolated using the Geneclean kit, Biol01 (1070 Joshua Way, Vista, Calif. 92083, 1-800-424-61010). The his-tag expression plasmid pQE32 (FIG. 8) (available from QIAGEN, Inc.) is digested with SmaI and HindIII. The 2895 bp fragment is then ligated to pQE32, creating pEB313 (FIG. 1).

This plasmid, pEB313, encodes a his-tagged eae fragment of 101 kDa, called RIHisEae, which encodes 900 out of 935 predicted amino acids. This his-intimin fusion is constructed so that the N terminal 35 amino acids are deleted, to remove any potential signal sequence. A signal sequence could target the fusion protein to the membrane or lead to cleavage of the His tag from the encoded intimin.

After the pEB313 construct is made, it is transformed into a lab strain of *E. coli* containing the lac repressor ($lacI_Q$), such as M15 pREP4 (repressor contained on the multicopy plasmid pREP4, supplied by QIAGEN, Inc.) (FIG. 9) or XL1BlueF' Tn5$lacI_Q$ (repressor contained on the single copy F' plasmid, also available from QIAGEN, Inc.). The transformed *E. coli* express the his-intimin fusion protein encoded by pEB313. Purification of the protein is accomplished as set forth in Example III.

B. Construction of a Plasmid, pHis-Inv1, Encoding His-tagged *Yersinia pseudotuberculosis* Invasin, and Construction of a Plasmid, pHis-Inv2, Encoding His-tagged *Yersinia pseudotuberculosis* Invasin with a Deletion of the N-terminal 40 Amino Acids.

The plasmid pRI203 contains a 4.6 kb fragment of *Yersinia pseudotuberculosis* chromosomal DNA, including the inv gene and surrounding nucleotide sequences, and is readily obtainable from Dr. Ralph Isberg (Dept. Of Molecular Biology and Microbiology, Tufts University School of Medicine, Boston, Mass. 02111; ref. R. R. Isberg, D. L. Voorhis, and S. Falkow. Cell. 50:769 (1987)). The pRI203 DNA is extracted from the supplied bacterial strain with the use of a QIAGEN DNA extraction kit (QIAGEN, Chatsworth, Calif.) according to the instructions of the manufacturer.

To construct pHis-Inv1, two primers, Inv1 (=5' GTACGGATCCATGATGGTTTTCCAGCCAATCAGTGAG 3' (SEQ ID NO:3)and Inv3 (=5' GTACGGTACCTTATATTGACAGCGCACAGAGCGGG 3' (SEQ ID NO:4)) are used in a PCR reaction (as described above in part A) to amplify the desired inv sequences from pRI203. The resulting 2960 bp inv fragment is digested with BamHI and KpnI, run on an agarose gel, excised with a razor, and purified using GeneClean (Bio101, LaJolla, Calif.). The purified inv fragment is ligated into the His-tag QIAGEN vector containing the appropriate reading frame corresponding to the amplified inv sequence (pQE30, 31 or 32, QIAGEN, Chatsworth, Calif.), digested with BamHI and KpnI. The ligated plasmids are then transformed into DH5αF'Tn5$lacI_Q$, and transformants checked for the presence of the appropriate size insert.

The plasmid pHis-Inv2 is constructed in the event that a signal sequence (and therefore the adjoining His tag) is cleaved from the protein expressed from pHis-Inv1. To construct pHis-Inv2, two primers, Inv2 (=5' GTACGGATC-CATATGTGGAATGTTCATGGCTGGGG 3' (SEQ ID NO:5)) and Inv3 (=5' GTACGGTACCTTATATTGA-CAGCGCACAGAGCGGG 3' (SEQ ID NO:4)) are used in a PCR reaction (as described in part A above) to amplify the desired inv sequences from pRI203. The resulting 2840 bp inv fragment is purified as above, and ligated into the His-tag QIAGEN vector as above, and transformed into a similar bacterial host strain.

Alternatively, similar plasmids are constructed by restriction enzyme digestion of pRI203, followed by ligation into the QIAGEN His-tag vector (pQE30, 31 or 32) containing the appropriate reading frame relative to the 5' end of the invasin fragment. The preceeding examples are meant to illustrate the construction of plasmids encoding histidine-tagged invasin from *Yersinia pseudotuberculosis*. One of ordinary skill in the art recognizes that analogous constructs, designed using alternative vectors and/or other intimin-like proteins can be constructed according to standard methods in the art. One of ordinary skill in the art also recognizes that the above his-tagged invasins and other his-tagged intimin-like proteins may be applied to the methods disclosed elsewhere herein.

C. Construction of a Plasmid (pEB312) (FIG. 10) Encoding His-tagged Intimin Encompassing 604 out of 935 Predicted Amino Acids.

Digested plasmid pEB310 (obtained as described in part A) with EcoRV and HindIII, isolating the 1971 bp fragment, and ligating the fragment into pQE32 digested with SmaI and HindIII. Restriction enzymes, ligases, Klenow fragment used in protocols are from New England BioLabs (32 Tozer Rd., Beverly, Mass. 01915-55991, 1-800-NEB-LABS) or Gibco BRL (P.O. Box 681 Grand Island, N.Y. 14072-0068, 1-800-828-8686). The resulting plasmid is designated pEB312.

The plasmid pEB312 encodes a his-tagged eae fragment called RVHindHis, which is about 65 kDa and encodes 604 out of 935 predicted amino acids. This construct contains the C-terminal two-thirds of the wild-type intimin protein.

As with the pEB310-expressed intimin, the fusion proteins remain primarily in the insoluble pellet after sonic disruption of the host *E. col*. Therefore, urea and guanidine HCl are included in the purification protocol, which allows extraction of the fusion proteins from the insoluble pellet.

D. Construction of Additional Plasmids Expressing Different Fragments of eae.

Each of these plasmids is tested to ensure that the protein fragment is capable of adhering to cultured cell lines using an adherence assay. (See example IV, below). In addition, the selection of the size of the intimin varies with whether the protein is expressed alone and whether cross-immunity is desired with an intimin-like protein of known amino acid sequence. In addition to intimin expressed from EHEC and EPEC, examples of intimin-like proteins include, but are not limited to, intimin-like proteins of *Citrobacter rodentium, Hafina alveii*, and the invasins of *Yersinia enterocolitica* and *Yersinia pseudotuberculosis.*

For instance, the larger 900 aa intimin is selected if there is heightened desire for cross-immunity with *Yersinia pseudotuberculosis*, because EHEC intimin shares 31% identical and 51% similar amino acids with the protein of *Yersinia pseudotuberculosis*, known as invasin (Yu, J. and Kaper, J. B. Mol. Microbiol. 6:411 (1992)). A greater degree of homology exists within the amino terminal two-thirds of the respective proteins.

Invasin is a 103 kDa outer membrane protein that allows bacterial penetration of cultured epithelial cells (Isberg, R. R. et al. Cell. 60:769 (1987)) and efficient penetration of the intestinal epithelium in vivo (Pepe. J. C. and V. L. Miller. Proc. Natl Acad. Sci. USA. 90:6473 (1993)). Cell adhesion receptors on the intestinal epithelium, which have been identified as integrins, bind invasin prior to bacterial internalization (Isberg, R. R. and J. M. Leong. Cell. 50:861 (1990)). The central portion of invasin is responsible for protein localization to the outer membrane, while the C-terminus is required for receptor binding (Isberg, R. R. Mol. Microbiol. 3:1449 (1989)).

Similarly, a larger 900 aa intimin is selected if there is heightened desire for cross-immunity with Enteropathogenic *Escherichia coil* (EPEC), *Citobacter rodentium*, or *Hafnia alvei*. EPEC intimin shares 83% identity with EHEC intimin over the entire length of the protein; the N-terminal 75% of the proteins share 94% identity, while the C-terminal 25% of the proteins share 49% identity (Yu, J. and Kaper, J. B. Mol. Microbiol. 6:411 (1992)). *Citrobacter rodentium* intimin shares 84% nucleotide identity to EHEC eae within the first 2106 bp, and 57% identity to the 3' 702 bp (Schauer, D. B. and Falkow, S. Infect. Immun. 61:2486 (1993)).

The plasmids that express different fragments of eae can be constructed using one of the following techniques: (1) use of a convenient restriction site within eae, for example, pEB313 digested with Sa/l and HindIII, isolation of the 1298 bp fragment, and ligation to pQE30 (QIAGEN, Inc.) digested with SmaI and HindIII. The resulting plasmid expresses the last 432 amino acids at the C terminus of eae; (2) deletion of the 5' or the 3' region of any desired fragment using nuclease BAL-31, Exonuclease III, or Mung bean nuclease (all available from New England BioLabs, 32 Tozer Rd., Beverly, Mass. 01915); (3) construction of plasmids with noncontiguous eae fragments, also using the above techniques; and (4) construction of plasmids encoding desired specific sequences with the use of PCR primers specifying the 5' and 3' ends of such sequences, as described in greater detail below.

With respect to the third technique, a His-tagged middle third intimin deletion mutant plasmid is constructed (pMW114). The plasmid pMW106 (described below) is transformed into the dam strain DM1F'Tn5/ac/$_Q$. DNA is made using the QIAGEN kit (QIAGEN, Inc.), and is digested with Bcl/I. The DNA is run out on an agarose gel. The 5178 bp band is cut out, is purified using GeneClean (Bio 101), is ligated, and then transformed into DH5αF'Tn5/ac/$_Q$ (or other appropriate strain such as XL1Blue or M15pREP4). Transformants are checked by restriction digestion of DNA. This description does not preclude the construction of other plasmids encoding non-contiguous eae sequences.

With respect to the fourth technique, PCR can be used to amplify specific fragments of eae; the fragments are isolated by restriction enzyme digestion and agarose gel electrophoresis, and ligated into the appropriate His-tag expression vector (i.e. p.QE30, 31 or 32; QIAGEN, Inc.).

For example, clones are constructed encoding various regions of eae (see FIGS. 11 and 12). The capacity of these clones to retain adherence function is assessed by either (1) transformation into the eae mutant, followed by adherence assays with HEp-2 cells (see Ex III, section C), or (2) addition of exogenous protein to bacteria (see Ex III, section D). It is important that the fragment selected retains full or close to full wild type binding activity. Alternatively, an acceptable clone from potentially any portion of the molecule is one which, encodes a polypeptide which can elicit antibodies which block the binding activity of wild-type intimin.

It is hypothesized that clones containing the highest binding activity will include the C-terminal third (the third third) of the protein, perhaps as little as 150 C-terminal amino acids. This hypothesis is supported, for example, by the findings disclosed by Frankel et al., Infection & Immunity, 62:1835 (1994), Frankel et al., Infection & Immunity, 63:4323 (1995), and Frankel et al., J. Biol. Chem., 271:20359 (1996). Proteins cannot be thought of as linear arrays of amino acids; rather they exist in a 3-dimensional structure. It is important to keep in mind that a single amino acid change or a deletion of a portion of the protein can perturb this structure. Therefore, full cell binding activity may require the presence of additional non-contiguous sequences along with the third third putative binding domain.

It is further hypothesized that clones containing high binding activity will include the two C-terminal Cys (encoded at bp 2780 and bp 3002, numbering ref; Beebakhee, G., J. DeAzavedo, and J. Brunton, FEMS Microbiology Letters 91:63 (1992)) for hypothesized disulfide bond formation and resulting loop formation. Additionally, it is hypothesized that clones containing high binding activity may require one or both aspartate(s) (encoded at bp 2819 and 2828, numbering ref. Beebakhee). This hypothesis is supported, for example, by analogy to invasin, as described in Leong, J. M. , Embo. J. 14:422 (1995).

All clones are constructed in a similar manner. PCR primers are designed which specify the 5' and 3' region of the desired eae fragment. To facilitate cloning into pQE31, each 5' primer (MW1, MW3, MW5, MW7, MW8, MW9, MW10) contains a 5' BamHI site, and each 3' primer (MW2, MW4, MW6, MW11, MW12) contains a 5' KpnI site. Each PCR primer is designed so that the reading frame of the specified eae sequence is appropriate for insertion into pQE31. The following His-tagged constructs are cloned using the indicated PCR primers:

(1) pMW101—encodes the N-terminal third of eae; 27 kDa protein (PCR primers: MW1 (5' PCR primer)=5' GTACG-GATCCGAATTCATTTGCAAATGGTG 3' (SEQ ID NO:6); MW2 (3' PCR primer)=5' GTACGGTACCTGAT-CAATGAAGACGTTATAG 3' (SEQ ID NO:7));

(2) pMW102—encodes the middle third of eae; 42 kDa protein (PCR primers MW3 (5' PCR primer)=5' GTACG-GATCCTGATCAGGATTTTTCTGGTG 3' (SEQ ID NO:8);

MW4 (3' PCR primer)=5' GTACGGTACCTGAT-CAAAAAATATAACCGC 3' (SEQ ID NO:9));

(3) pMW103—encodes the C-terminal third (282 amino acids) of eae; 32 kDa protein (PCR primers: MW5 (5' PCR primer)=5' GTACGGATCCTGATCAAACCAAG-GCCAGCATTAC 3' (SEQ ID NO:10); MW6 (3' PCR primer)=5' GTACGGTACCTTATTCTACACAAACCG-CATAG 3' (SEQ ID NO:11));

(4) pMW104—encodes the N-terminal two thirds of eae; 69 kDa protein (PCR primers: MW1 and MW4);

(5) pMW105—encodes the C-terminal two thirds of eae; 73 kDa protein (PCR primers: MW3 and MW6);

(6) pMW106—encodes eae with a small N-terminal 35 amino acid deletion; 100 kDa protein (PCR primers: MW1 and MW6);

(7) pMW108—encodes the C-terminal 150 amino acids of eae (PCR primers: MW7 (5' PCR primer)=5' GTACG-GATCCACTGAAAAGCAAGCGGTGGTGATG 3' (SEQ ID NO:12); MW6);

(8) pMW109—encodes the C-terminal 140 amino acids of eae (PCR primers: MW8 (5' PCR primer)=5' GTACG-GATCCTTCATGGTATTCAGAAAATAC 3' (SEQ ID NO:13); MW6);

(9) pMW110—encodes the C-terminal 130 amino acids of eae (PCR primers: MW9 (5' PCR primer)=5' GTACG-GATCCGACTGTCGATGCATCAGGGAAAG 3' (SEQ ID NO:14); MW6);

(10) pMW111—encodes the C-terminal 120 amino acids of eae (PCR primers: MW10 (5' PCR primer)=5' GTACG-GATCCGAATGGTAAAGGCAGTGTCG 3' (SEQ ID NO:15); MW6);

(11) pMW112—encodes 120 amino acids of eae with the C-terminus, spanning bp #2560–2923, (numbering refers to eae sequence of strain CL8 ref. Beebakhee, G., J. DeAzavedo, and J. Brunton. FEMS Microbiology Letters 91:63)). (PCR primers: MW7; MW11 (3' PCR primer)=5' GTACGGTACCTCCAGAACGCTGCTCACTAG 3' (SEQ ID NO:16));

(12) pMW113—encodes the C-terminal 282 amino acids of eae, Cys at bp 3002 changed to Ser with the use of the PCR primer MW12 (numbering refers to eae sequence of strain CL8 ref. Beebakhee, G., J. DeAzavedo, and J. Brunton. FEMS Microbiology Letters 91:63 (1992)) (PCR primers: MW5; MW12 (3' PCR primer)=5' GTACGGTACCTTATTCTACAGAAACCGCATAG 3' (SEQ ID NO:17)).

All clones are constructed by first diluting lyophilized primers to 10 μM with dH$_2$O. Template DNA from strain XL1blue pEB310 (encoding the entire eae gene) is made using a QIAGEN prep (QIAGEN, Inc.), is linearized by digestion with a restriction enzyme that does not cut within or near the coding region, for example HindIII, and is quantitated using a spectrophotometer. PCR reactions are conducted by combining 10 μl 10×Taq buffer (Perkin Elmer/Roche Branchburg, N.J.), 10 μl 2 mM dNTP mix (Boehringer Mannheim, Indianapolis, Ind.), 10 μl 10 μM 5' PCR primer, 10 μl 10 μM 3' PCR primer, 6μl 25 mM MgCl$_2$ (Perkin Elmer/Roche), 52 μl dH$_2$O, and 1 μl (1–10 ng) linear template DNA. Two drops of mineral oil are applied to the mixture, which is heated to 100° C. for 5 minutes to denature the template. One μl (5 U) of AmpliTaq polymerase (Perkin Elmer/Roche) is added, and the PCR reactions are begun: 95° C./1 min, 50° C./1 min, 72° C./3 min for 30 cycles, followed by 72° C./10 min, and holding at 4° C. After the PCR reactions are completed, the DNA is applied to a Wizard PCR clean-up kit (Promega, Madison, Wis.), and resuspended in 50 μl TE buffer. PCR amplified DNA is digested with BamHI and KpnI, electrophoresed on an agarose gel, the appropriate size band cut out, and purified by Gene Clean (Bio101, LaJolla, Calif.). Digested PCR fragments are then ligated into pQE31 digested with BamHI and KpnI, transformed into DH5αF'Tn5/ac/$_Q$ (or other appropriate strain, such as M15pREP4 or XL1Blue), and transformants checked for the presence of the appropriate size insert.

With respect to any of the disclosed protein extraction, enrichment, and purification techniques, if it is necessary to later remove the Histidine tag from the purified protein, a protease cleavage site can be inserted between the 6×His sequence and the N-(N-terminal tag) or C-terminus (C-terminal tag) of the protein. For example, Enterokinase recognizes the sequence "DDDK" (Asp$_4$-Lys), and cleaves after the lysine. A PCR primer encoding this sequence is designed and used to perform site-directed mutagenesis of the desired gene fragment. Alternatively, Carboxypeptidase A can be used for the removal of C-terminal His tags. This enzyme efficiently removes aromatic C-terminal residues (Hoculi, E. Chemische Industrie. 12:69 (1989)) until it encounters a basic residue, at which point removal is terminated. Additionally, PCR can be used to design a primer so that the protease site is encoded at the N- or C-terminus of the protein encoded; or PCR can be used to design the vector including those sites, and the above-techniques can be used to clone into the aforementioned vector.

All fragments of intimin expressed from pEB312 or other constructs are purified using a protocol similar to the protocol detailed in Example II, for large scale purification of intimin. It is apparent that those of ordinary skill in the art may select additional restriction sites or modify the protocol while remaining within the scope and spirit of the invention.

EXAMPLE II
Large Scale Enrichment of Histidine-tagged Intimin
Growing Large-Scale Expression Cultures Inoculate 20 ml LB (Luria-Bertaini) broth containing 100 μg/ml ampicillin and 40 μg/ml kanamycin with a loopful of M15 pREP4 pEB313 (prepared as described in Example I, above). Grow overnight (15–18 h) at 37° C., shaking vigorously. Inoculate 1L of LB broth containing 100 μg/ml ampicillin and 40 μg/ml kanamycin with 20 ml of the overnight culture. Grow culture at 37° C. with vigorous shaking until the $OD_{600}$=0.7–0.9 (~3 h). Add IPTG (isopropyl β-D-thiogalactopyranoside, Sigma Chemical Co., P.O. Box 14508, St. Louis, Mo. 63178, 1-800-325-3010) to a final concentration of 1 mM (0.476 g) and continue to grow culture for another 3 h. Divide supernatant into 500 ml bottles (previously weighed) and centrifuge at 4000×g for 10 minutes. Discard the supernatant, weigh cell pellet, and store at −70° C., or process immediately.

Thaw cells for 15 minutes, vortex and resusupend in Buffer A [6 M GuHCl, 0.1 M $NaH_2PO_4$, 0.01 M Tris-HCl, pH 8.0] at 5 ml/g wet weight. Stir cells for 1 hour at room temperature. Centrifuge lysate at 10,000×g for 15 min, collect supernatant. Add 5 ml of a 50% slurry of Ni-NTA resin (Ni-NTA slurry from QIAGEN, Inc), previously equilibrated with Buffer A. Stir at room temperature for 45 minutes, let the slurry settle, remove the supernatant, add 5 ml Buffer A, let the slurry settle, remove the supernatant, add 5 ml Buffer A, and load the resin into a column. The column is washed with 10 column volumes of Buffer A, followed by washes with Buffer B [8 M urea, 0.1 M $NaH_2PO_4$, 0.01 M Tris-HCl, pH 8.0] until the $OD_{280} \leq 0.01$ (at least 5 column volumes). Wash the column with Buffer C [6M urea, 0.1M $NaH_2PO_4$, 0.01 M Tris-HCl, pH 6.3] until the $OD_{280} \leq 0.01$. The protein is eluted with Buffer C plus 250 mM imidazole, collecting thirty 1 ml fractions.

Record the $OD_{280}$ of each fraction. Pool aliquots of the purified protein containing similarly high $OD_{280}$ readings into dialysis tubing (eg. Spectra/Por Cellulose Ester Membrane MW cut off=8000; Spectrum Medical Industries, 1100 Rankin Rd. Houston, Tex. 77073-4716), and equilibrate in cold (4° C.) Buffer C containing 6M urea (not 8M urea). Adjust the concentration of the aliquots to $\leq 1$ mg/ml using a standard commercial protein quantitation kit (Bio-Rad Microassay, Bio-Rad Labs, 2000 Alfred Noble Dr., Hercules, Calif. 94547, 1-800-4-BIORAD), with BSA diluted in Buffer C (containing 6M urea) as the standard. Perform step dialysis of the protein in the cold (4° C.) beginning with Buffer C (containing 6M urea) and reducing the molarity of the urea by whole number increments. Dialyze for one hour in each solution, ending in 1×PBS. Analyze the protein by (10%) SDS-PAGE running ~2 μl protein per well to verify protein size and quantity. The molecular weight of RlHisEae is 101 kDa.

Alternatively, add protein to dialysis tubing, dialyze straight into 1×PBS. Quantitate the protein using a standard commercial protein quantitation kit (Pierce BCA Protein Assay Kit, Pierce, P.O. Box 117, Rockford, Ill. 61105), aliquot, and store at −20° C. As with the first alternative, analyze the protein by (10%) SDS-PAGE running ~2 μl protein per well to verify protein size and quantity.

Upon enrichment of his-tagged intimin, the material derived is analyzed for level of purity by SDS-PAGE. A 10% SDS-PAGE gel is loaded with a 2 μsample of enriched his-tagged intimin and electrophoresed at 200 V for one hour. Molecular weight markers are included on the gel for size comparison. When the gel is stained with Colloidal Coomasie stain (Sigma, St. Louis, Mo.), the most prominent band appears at ~101 kDa. Several other less prominent high molecularweights bands also appear. When the gel is stained with silver stain (BioRad, Richmond, Calif.) according to the instructions of the manufacturer, very slight high molecular weight bands appear, as well as several more prominent bands at low molecular weights, the most prominent band appearing around 29 kDa. The enriched product preferably contains approximately 70–80% of the full-length (i.e., 900 out of 935 predicted amino acids) intimin. Preferably the enriched product contains no more than 25% contaminants (i.e., non-intimin related molecules), more preferably no more than 20% contaminants, still more preferably no more than 10% contaminants.

EXAMPLE III
Purification of Enriched Histidine-Tagged Intimin

An enriched preparation of his-tagged intimin, generated as described in Example II above, is purified by techniques known to those skilled in the art, including, but not limited to, high performance liquid chromatography (HPLC), gel column chromatography, and SDS-PAGE.

With the SDS-PAGE method, an enriched preparation of his-tagged intimin is separated on a 10% polyacrylamide gel and visualized, for example, by staining an analytical lane with Colloidal Coomasie strain (Sigma, St. Louis, Mo.). The high molecular weight full-length intimin band can be excised from the preparative gel with a razor, and stored at 4° C. prior to immunization. Less than full-length fragments of intimin, i.e. portions of intimin, and/or intimin conjugated to one or more antigens can similarly be excised from the gel.

Regardless of the method used to purify intimin, or portion thereof, the purified protein as used herein refers to a population of polypeptides consisting solely of intimin or portions or intimin, optionally tagged with histidine. It has been recognized in the art that the population of polypeptides expressed from a fragment of DNA containing only one open reading frame encoding intimin (or intimin-like proteins) can separate into multiple bands on an SDS-PAGE gel. McKee et al., Infection & Immunity, 64(6):2225–2233 (1996), Jerse et al., Proc. Natl. Acad. Sci. USA 87:7839–7843 (1990), and Isberg, Cell 50:769–778 (1987). Thus, purified intimin, or portions of intimin or intimin-like proteins and intimin or intimin-like proteins conjugated with one or more antigens, may be visualized as multiple bands on an SDS-PAGE gel.

EXAMPLE IV
A. Adherence Assay

Adherence of *E. coli* to either HEp-2 or HCT-8 cells is assessed by a modification of the method of Carvioto et al. Curr. Microbiol. 3: 95–99 (1979). Specifically, overlay semi-confluent monolayers of HEp-2 cells on glass coverslips in 24 well tissue culture dishes or in 8 well Permanox Chamber Slides (Nunc, Naperville, Ill.) with adherence assay medium (EMEM, or Eagle's Minimum Essential Medium supplemented with 0.4% sodium bicarbonate and 1% mannose) which contain 20 µl/ml (v/v) of an overnight culture of the bacteria to be tested in LB broth.

Each inoculum contains ≧$10^7$ bacteria (described below) which results in an approximate multiplicity of infection (MOI) of 100:1. The infected monolayers are incubated at 37° C. in a 5% $CO_2$ atmosphere. After three hours, the medium, which contains the nonadherent bacteria, is aspirated and the monolayers washed once with sterile 10 mM phosphate buffered saline, pH 7.4 (PBS: sodium chloride, sodium phosphate dibasic, and potassium phosphate monobasic).

Fresh adherence assay medium is added to the cells with adherent bacteria, and the infected cells are then incubated for an additional 3 hours. The monolayers are then washed six times with PBS to remove nonadherent bacteria. Each wash is gently removed by aspiration in an attempt to avoid disturbing the monolayers. Each assay is done ≧2 times and duplicate slides are prepared to permit both Giemsa and FITC-phalloidin (FAS) staining to visualize binding and associated sequelae.

For Giemsa staining, the HEp-2 cells and adherent bacteria are fixed with 70% (v/v) methanol (glass coverslips) or graded acetone washes (chamber slides) and stained with 1:10 Giemsa (Sigma) for 20 minutes. To assess the FAS phenotype, the FITC-Phalloidin (Sigma) staining procedure of Knufton et al. Infect. Immun. 57: 1290–1298 (1989) is used. Phalloidin is a mushroom phallotoxin that specifically binds filamentous, not globular, actin. FITC-phalloidin-stained preparations are examined by both phase contrast and fluorescent microscopy using an Olympus model GHS microscope with a model BH2-RFL reflected light fluorescence attachment (Olympus Optical Co., Ltd., Tokyo, Japan).

Adherence assays with HCT-8 cells are done by the procedure described above for HEp-2 cells, but the bacteria are allowed to interact with the HCT-8 cells for 2.5 hours before the first wash and an additional 2.5 hours before terminating the assay. All assays with HCT-8 cells are carried out in 8 well permanox Chamber Slides.

B. Construction of a Bacteria for Use in the Assay: An EHEC eae mutant

Figure 13:
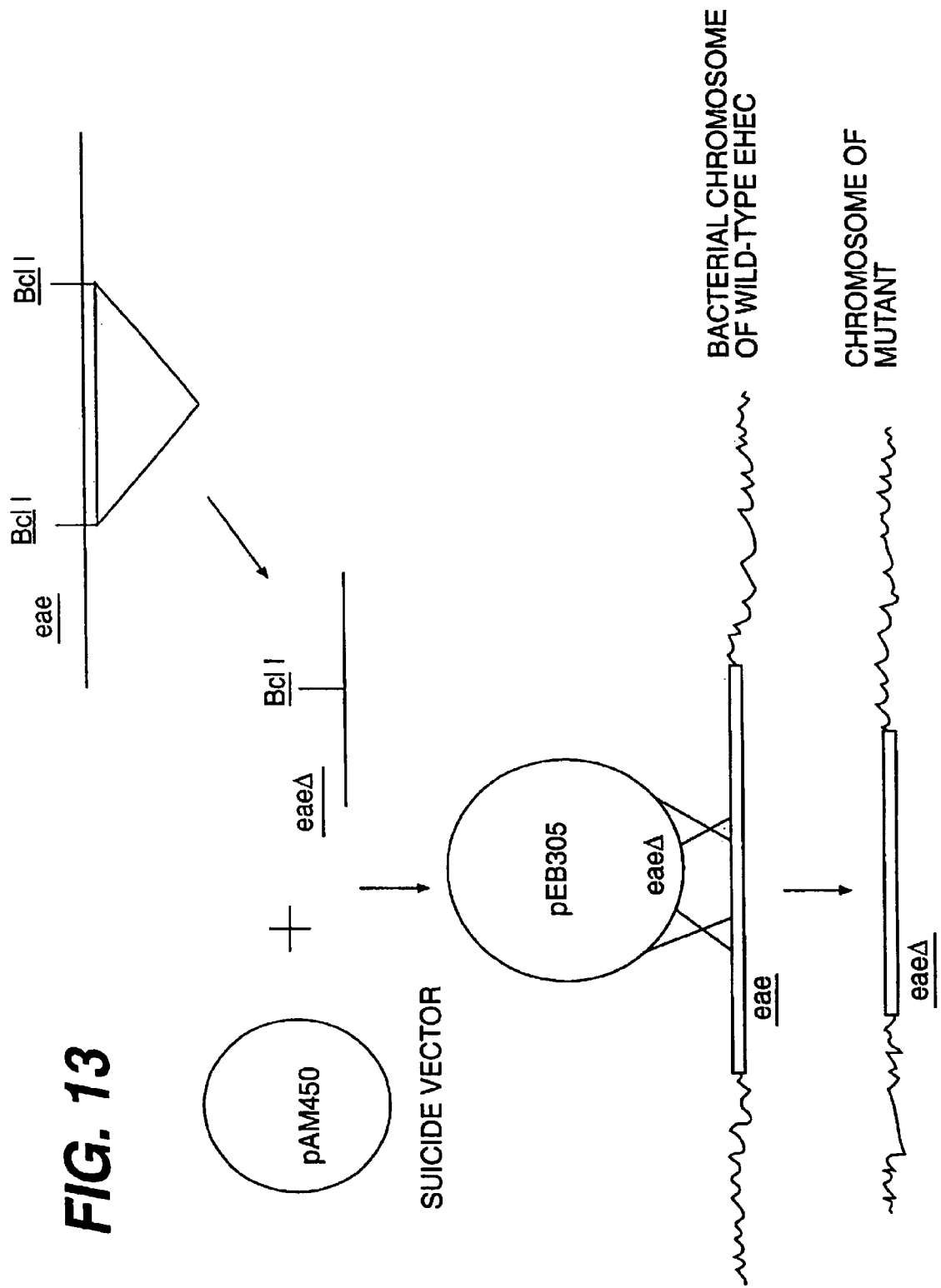
FIG. 13 depicts the construction of an eae mutant, 86-24 eaeΔ10, by allelic exchange.
Figure 14:
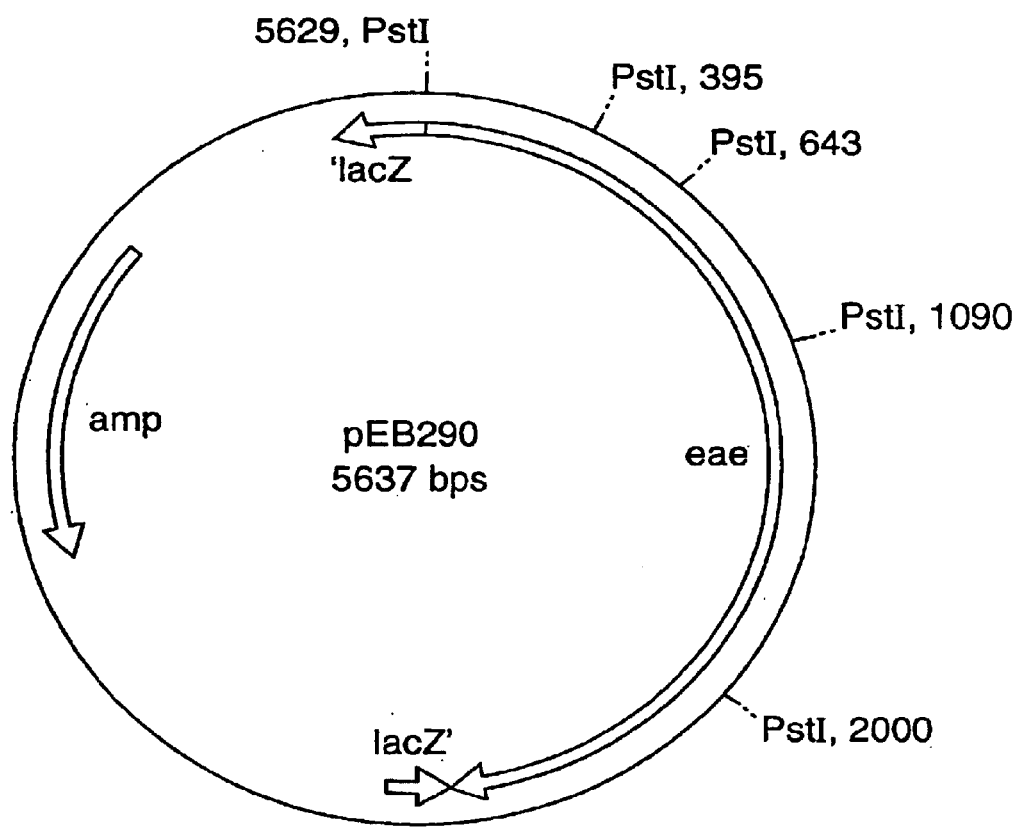
FIG. 14 depicts pEB290, a plasmid encoding most of the eae structural gene. The 3' 250 bp of eae are not encoded by pEB290.

To create an in-frame deletion in the chromosomal copy of the eae gene in a particular strain of EHEC, strain 86-24, the wild-type copy of the gene is replaced by double homologous recombination with an internally-deleted copy of eae (FIG. 13). Plasmid pEB290 (FIG. 14) encloses most of the eae structural gene and is constructed from a PCR product amplified from the 86-24 chromosome with primer MM1 (MM1=ATAACATGAGTACTCATGGTTG (SEQ ID NO:18); starts at the second codon of the eae structural gene and includes a ScaI restriction site), in combination with primer MM2 (MM2=TCTAGAGAGAAAACGTGAATGTTGTCTCT (SEQ ID NO:2)). The resultant 2,953 base pair fragment derived by PCR is digested with the ScaI and XbaI and ligated into pBluescript SK+(Stratagene) that is restricted with SmaI and XbaI. DNA sequencing of the ends of the pEB 290 insert reveals that the 3' 250 base pairs are lost.

Figure 15:
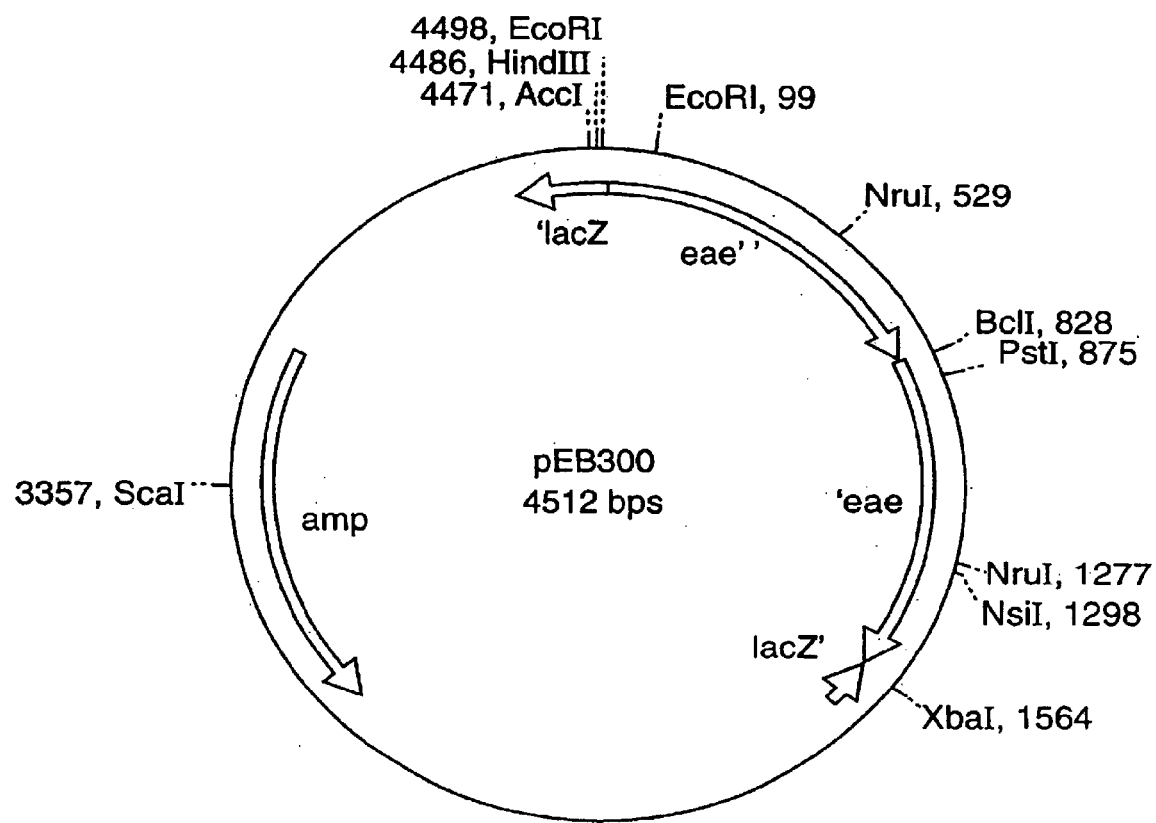
FIG. 15 depicts pEB300, used to construct the deletion mutant; deleted for the 1275 bp internal Bcl 1 fragment of eae.

Plasmid pEB290 is transformed into *E. coli* strain GM119 [dam-6, dcm-3, [Arraj, J. A. and Marinus, M. G. J. Bacteriol. 153:562–565 (1983)] to obtain unmethylated DNA which is sensitive to the restriction endonuclease Bc/l. Plasmid DNA is isolated (Maniatis, et al., Molecular cloning: a laboratory manual. Cold Spring Harbor (1982)) and restricted with Bc/l to remove an internal 1125 bp fragment from the gene. The resulting sticky ends are ligated to each other to create pEB300 (FIG. 15).

Figure 16:
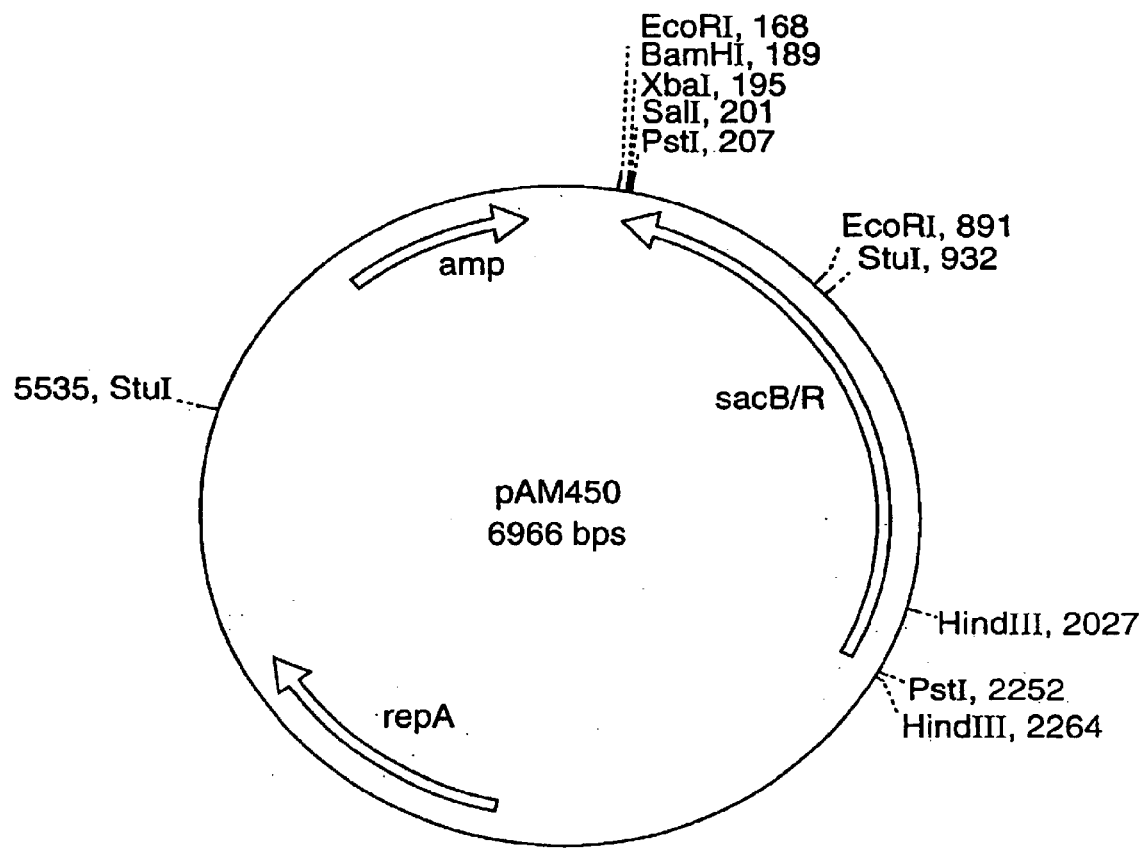
FIG. 16 depicts pAM450, a suicide vector for introduction of cloned genes into the bacterial chromosome.
Figure 17:
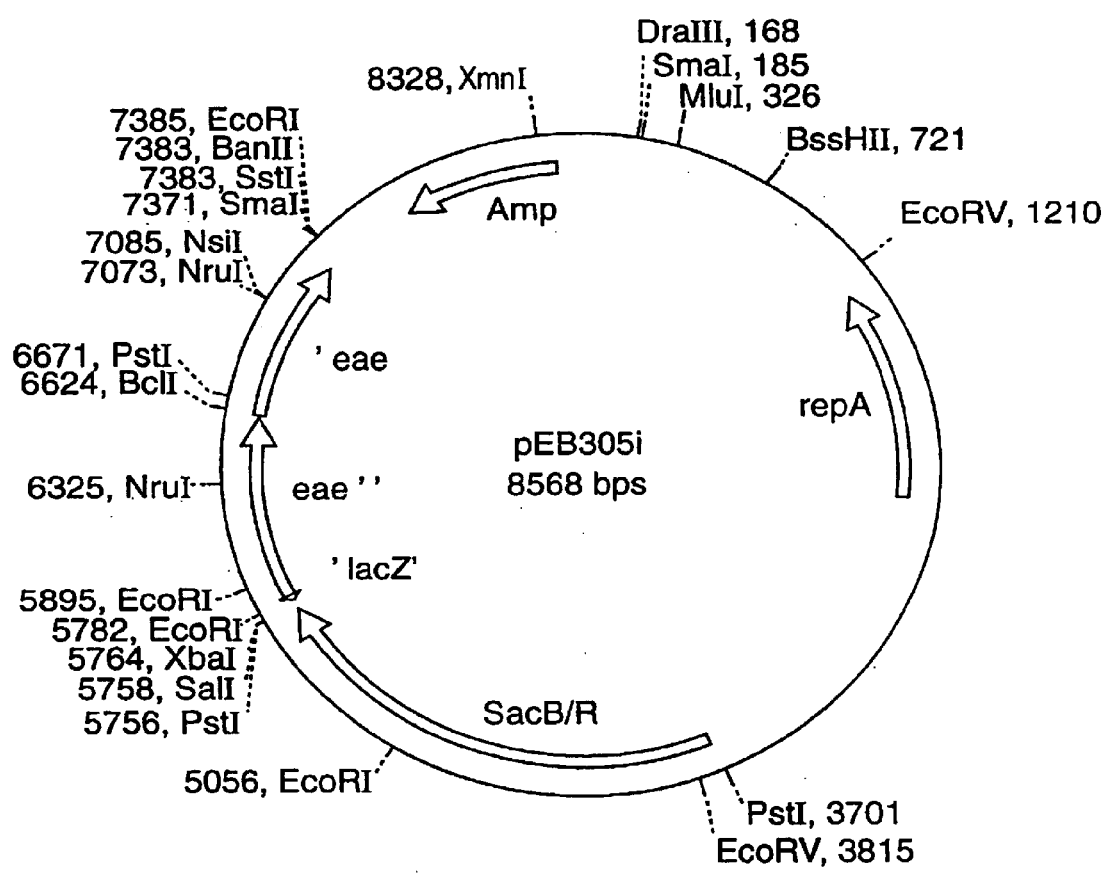
FIG. 17 depicts pEB305i, a plasmid encoding the deleted eae gene in pAM450 vector for homologous recombination.
Figure 18:
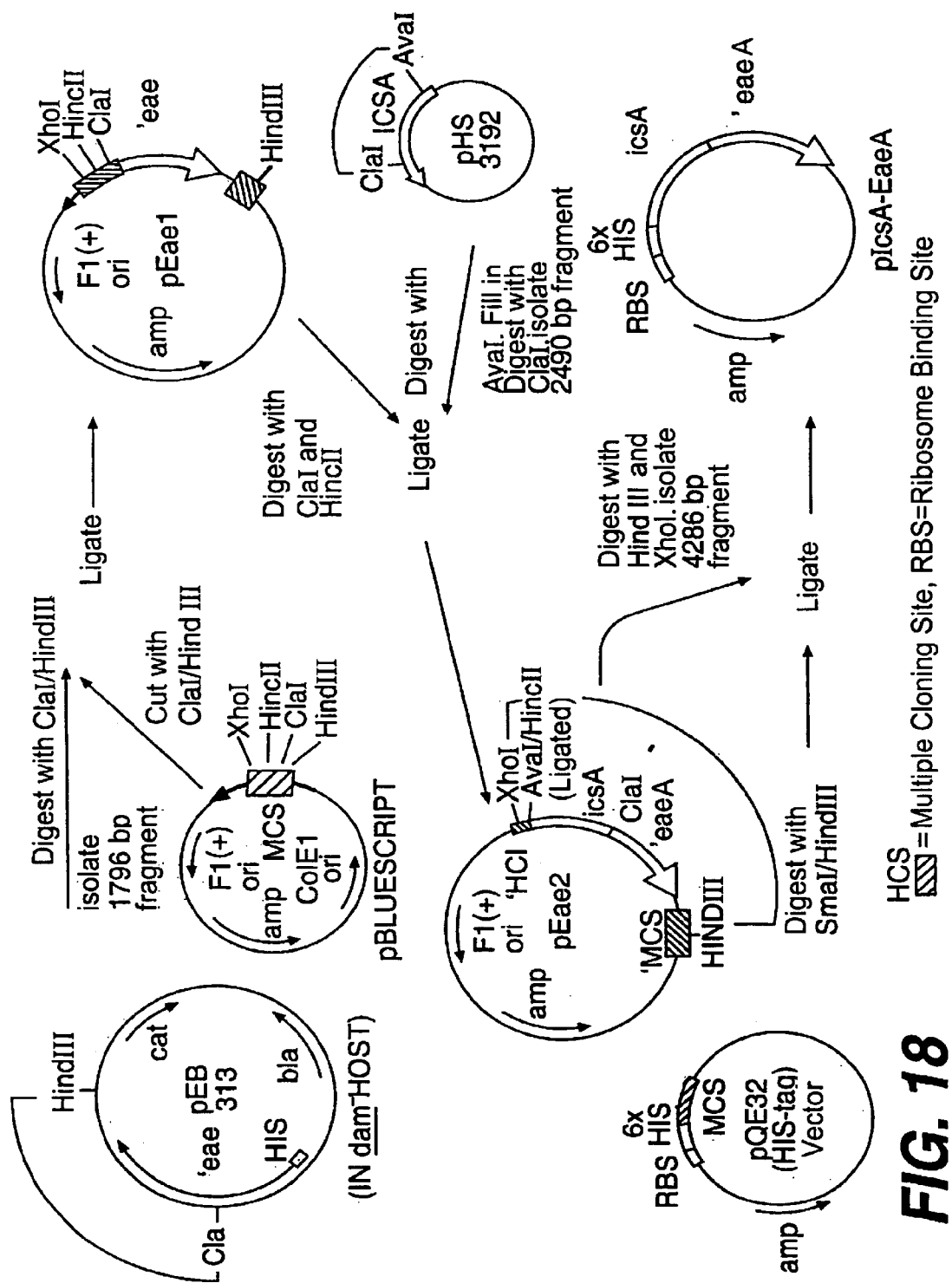
FIG. 18 depicts the cloning scheme for construction of a plasmid expressing N-His-IcsA-intimin-C.

The deleted eae gene is excised by digesting pEB300 with XbaI and HindIII, and the fragment containing the eae sequence is ligated into the BamHI site of the suicide vector, pAM450 (FIG. 16) to form pEB305. Plasmid pAM450 is a derivative of pMAK705 (Hamilton et al., J. Bacteriol., 171:4617–4622 (1989)) with three features. First, it has a temperature sensitive (ts) origin of replication. Second, the plasmid carries the sacB/R locus from *Bacillus subtilis*, rendering the host strain sensitive to sucrose (Gay et al., J. Bacteriol 164:918–921 (1985)); Lepesant et al., Marburg. Mol. Gen. Genet. 118:135–160 (1972)). Third, the plasmid encodes ampicillin resistance. These features allow homologous recombination and positive selection for a second recombination event resulting in resolution and loss of vector sequences. The insertion of the deleted eae gene (from pEB300) into the suicide vector (pAM450) results in the plasmid called pEB305 (FIG. 17).

The suicide:eae construct, pEB305i, is transformed into wild type EHEC strain 86-24 by electroporation (Sizemore, et al., Microb. Pathog. 10:493–499 (1991)). Double recombinants that have been cured of the vector sequences are selected by growth on medium containing sucrose and then screened for ampicillin sensitivity (Blomfield et al., Mol. Microbiol., 5:1447–1457 (1991)). Transformants that have been cured of the suicide vector sequences are sucrose resistant, ampicillin sensitive, and able to grow equally well at 30° and 42° C. Deletion of the chromosomal eae sequences is confirmed by: (i) the reduced size of the eae fragment after PCR amplification with primers MM1 and MM2; (ii) Southern blot analysis of the mutated chromosomal DNA; (iii) loss of restriction sites within the deleted region of the eae gene; and (iv) the inability of an internal probe to recognize the mutated chromosome.

The resulting in-frame deletion mutant of EHEC strain 86-24 strain is designated 86-24eaeΔ10. The mutation is confirmed to be in frame by in vitro transcription and translation analysis of the PCR-derived product from 86-24eaeΔ10. A truncated protein product of the predicted size, about 68,000 Da, is identified by [$^{35}$S] methionine labeling of the translation product. The eae mutant strain is identical to wild type 86-24 in all characteristics, including: growth in LB broth, agglutination with O157 and H7 antisera, inability to ferment sorbitol, and growth on MacConkey agar at 37° C.

Those of ordinary skill in the art will recognize that other methods of creating strains of EHEC that are mutated in eae and do not retain binding ability are possible and may be substituted.

C. The Role of eae in EHEC Adherence in vitro

The isogenic strains, 86-24, 86-24eaeΔ10 and 86-24eaeΔ10 carrying pEB310 are tested for adherence to HEp-2 and HCT-8 cells. Wild type 86-24 forms microcolonies when the bacteria interact with HEp-2 or HCT-8 cells. M. L. McKee & A. D. O'Brien, Infection & Immunity 63:2070 (1995). This localized adherence is FAS (fluorescence actin staining) positive which indicates the polymerization of F-actin at the site of bacterial attachment (i.e., the expected result). The mutant 86-24eaeΔ10 is unable to adhere to HEp-2 cells. When eae is introduced into 86-24eaeΔ10 on either pEB310 or pEB311, the LA/FAS (LA=localized adherence or microcolony formation) phenotype is fully restored, an observation which demonstrates that intimin alone complements the eae mutation. Since both of the clones complement the eae mutant, the native promoter for eae is present in the PCR amplified sequences.

D. Effect of Adding Exogenous His-intimin Fusion Proteins

The adherence assay also may be used to evaluate the effect of exogenously added His-intimin fusion proteins on the binding capability of 86-24eaeΔ10 and the binding capability of wild-type strain 86-24. In this case, the purified His-intimin fusion proteins are added to the epithelial cell monolayers before addition of bacteria as indicated in each experiment.

HEp-2 cells are incubated with 20 ng–20 μg of RIHisEae for 30 minutes prior to the addition of 86-24 to the monolayer. The infected monolayers are then washed extensively, stained with FITC-phalloidin, and observed microscopically. The fusions enhance binding wild type strain of 86-24 to HEp-2 cells. The size of the 86-24 microcolony as well as the total number of HEp-2 cells with adherent microcolonies increases as the concentration of RlHisEae increases. At high doses (20 μg), the fusion protein causes the HEp-2 cells to show aberrant appendages and processes. For this reason, 1–2 μg is the most preferred dose for further studies.

When added exogenously to HEp-2 cells, RlHisEae complements the HEp-2-cell binding defect (or restores binding capability) of 86-24eaeΔ10. The shorter fusion protein, RVHdHisEae, also complements for adherence. A similar amino terminal fusion of histidine residues to mouse dihydrofolate reductase (His-DHFR) does not enhance the adherence of 86-24. Moreover, the plasmids that encode the intimin fusion proteins, pEB312 and pEB313, are able to complement 86-24eaeΔ10 for attachment in vitro. Thus, such studies indicate that the proteins encoded by pEB312 and pEB313 are sufficient to confer adherence.

As noted above in Example I, the fusion proteins localize to the insoluble pellet fraction after sonic disruption of the host strains, indicating that these proteins are localized to the membrane. Plasmid pQE16, which encodes the His-DHFR fusion, does not complement 86-24eaeΔ10 (data not shown). That the irrelevant protein fusion with the histidine residues does not confer HEp-2 cell adherence on the eae mutant indicates that the histidine residues added to intimin are not responsible for the activity observed for the exogenously added His-intimin fusions. The enhancement or complementation of EHEC binding to HEp-2 cells observable with exogenous RlHisEae and RVHdHisEae indicates that intimin interacts with both the bacteria and the epithelial cell.

EXAMPLE V
The Role of eae in vivo—Gnotobiotic Piglet Infection Model

The role of intimin in intestinal colonization, A/E lesion formation, and EHEC-mediated colitis and diarrhea in the gnotobiotic piglet is evaluated by the method of Francis, et al. (Francis et al., Infect. Immun., 51:953–956 (1986)). Both pairs of piglets inoculated with the wild-type parent strain, 86-24 develop diarrhea and have edema in the mesentery of the spiral colon at necropsy.

Histologically, strain 86-24 primarily colonizes the cecum and spiral colon. Histologically and by culture, no evidence of bacterial dissemination to the liver, kidney, lung, or brain is detected. Intimate bacterial adherence and A/E lesions, as described by Staley (Staley et al., Vet. Pathol. 56:371–392 (1969)) and Moon (Moon et al., Infect. Immun., 41:1340–1351 (1983)) for EPEC, are evident by both light and EM examination of cecum and colon of piglets infected with 86-24. A/E lesions include the accumulation of electron-dense material at the site of attachment. In some areas, sloughed enterocyte fragments and microvilli with attached bacteria are noted in the gut lumen. In histologic sections of the cecum and spiral colon of piglets infected with 86-24, an inflammatory infiltrate is seen. Inflammation is characterized by scattered neutrophils in the lamina propria and mild diffuse accumulation of serous fluid and perivascular lymphocytes and macrophages in the submucosa.

Both piglets inoculated with the mutant strain, 86-24eaeΔ10 have formed feces at necropsy. Histologically and by EM examination, there is no evidence that strain 86-24eaeΔ10 is able to colonize piglet intestine and cause the A/E lesion. The few bacteria seen by light and EM examination are in the mucus overlaying the mucosal epithelium of the cecum and spiral colon. One of two piglets inoculated with 86-24eaeΔ0 has slight mesocolonic edema, but no other gross or microscopic lesions are seen in either piglet. See McKee et al., Infection and Immunity 63: 3739 et seq. (1995) (incorporated herein by reference).

Piglets inoculated with 86-24eaeΔ10(pEB310) have pasty feces and mesocolonic edema at necropsy. Strain 86-24eaeΔ10 (pEB310) intimately adheres to mucosal enterocytes and causes A/E lesions in the cecum and spiral colon. Histologically, perivascular lymphohistiocytic typhlocolitis, similar to that caused by wild type 86-24 is also seen.

Similar experiments are conducted in a colostrum-deprived newborn calf model, showing that intimin is necessary to provoke A/E lesions in the gut as well as to evoke *E. coil* O157:H7 strain 86-24-mediated diarrhea. (A. D. O'Brien, M. R. Wachtel, M. L. McKee, H. W. Moon, B. T. Bosworth, C. Neal Stewart, Jr., and E. A. Dean-Nystrom. "Intimin: Candidate for an *Escherichia coli* O157:H7 Anti-Transmission Vaccine". Abstract of the 32nd Joint Conference on Cholera and Related Diarrheal Diseases, Nagasaki, Japan, Nov 14–16, 1996, the disclosure of which is incorporated herein by reference.) These experiments also demonstrate that by 2 days post-infection the numbers of infecting organisms in the lower bowel are significantly less in the animals fed the eae mutant or a non-pathogenic *E. coli* strain than in the calves fed the wild type or the eae mutant with the complementing clone.

EXAMPLE VI
Recognition of EHEC Proteins by HC Patient Sera

Convalescent immune sera tested from hemorrhagic colitis patients (kindly provided by T. Barrett at the Centers for Disease Control and Prevention, Atlanta, Ga.) react with $P_{T7}$-expressed intimin preparations (i.e., his-intimin expressed by pEB310 and pEB311) in a Western immunoblot. To decrease reactivity of the hemorrhagic colitis patients' sera with *E coil* proteins in the expression system, sera samples are adsorbed with whole cell extracts of DH5α transformed with pGP1-2 and pBRKS⁻(the expression vector). After adsorption, the normal sera controls recognize only proteins in the ammonium sulfate concentrated fraction of the intimin preparations but no longer react with proteins expressed from pEB310 or the vector control. After adsorption, the HC patient sera still recognize many *E. coli* proteins, but the reaction with intimin remains strong.

EXAMPLE VII
Administration of His-intimin to Patients

The following example provides the administration of his-intimin to patients in order to stimulate a protective immune response. A protective immune response is one that elicits sufficient antibody to permit a patient to avoid infection, decrease the significance or severity of an infection, or decrease the ability of bacteria to colonize the gastrointestinal tract.

Methods of administration of his-intimin include, but are not limited to, injection (including, but not limited to, intraperitoneal, intravenous, subcutaneous, and intramuscular) of his-intimin directly into the patient to elicit an immune response, ingestion or by gavage of his-intimin alone or with food, and intra-nasal inoculation with his-intimin, which promotes binding of intimin to receptors of epithelial cells in the naso-pharynx.

When the his-intimin is ingested, the protein is contained within a gel capsule, liposome, or attached to an inert substance to aid in passage of the inoculum through the stomach. As the fusion protein is acid stable, it also is ingested by itself or may be mixed into a food product. A preferred method of administration is in a fusion protein of his-intimin and SLT (Shiga-like toxin). A his-intimin-SLT fusion protein is bound to SYNSORB (SynSorb Biotech, Inc., 1204 Kensington Rd, N.W., Calgary, Alberta, Canada, T2N3P5), which has a receptor for SLT, via the SLT-receptor interaction. The SYNSORB construct is mixed with chocolate pudding and fed to children.

Purified RiHisEae (His-tagged Eae, 900/935 amino acids), as well as the third third portion of intimin (encoded by pMW103), are stable after incubation at pH 2.0 at 37° C. for 24 hr. This indicates that a His-Eae fusion can pass through the stomach unharmed or undegraded. Moreover, in nature eae is expressed on the outer membrane of the bacterium and it still promotes intimate adherence after passing through the stomach, indicating its resistance to acidic environments.

Ingestion or intra-nasal inoculation stimulates local immunity, which thwarts future colonization by EHEC and EPEC. Cross-immunity through homology is stimulated to *Hafnia alvei* and *Citrobacter rodentium, Yersinia sp.* and other bacterial species having intimin-like proteins. Although it is not necessary to quantitate the degree of cross-immunity conferred by administration of intimin in order to benefit from a protective immune response to infection by bacteria other than EHEC that express intimin-related proteins, an assay for such protection is described in Example IX. The assay permits assessment of the efficacy of intimin antibodies on blocking interaction with epithelial cells by pathogens known to have intimin-like binding proteins.

In another embodiment, injection of his-intimin into cow udders leads to an immune response in the cow. Antibodies against the protein are present in the cow's milk. Calves that drink the milk are passively immunized until they can be actively immunized by the method of choice. Alternatively, his-intimin may be fed to cows or introduced into the cow's feed. The presence of his-intimin introduced in this way also stimulates an antibody response in the cows so that antibodies are produced and appear in the cows' milk.

Another embodiment involves the administration of nucleic acid vaccines. His-intimin is injected into a patient as naked eae DNA, or the DNA is delivered to the body by a carrier system such as retroviruses, adenoviruses, or other carriers known in the art. Following administration, the patient mounts an immune response against transiently expressed foreign antigens.

Currently nucleic acid vaccines, in general, are nearing clinical trials. This approach to vaccines involves delivering the DNA encoding the desired antigen into the host by inserting the gene into a nonreplicating plasmid vector (Marwick, C. JAMA 273:1403 (1995); reviewed in Vogel, F. R. and N. Sarver. Clin. Microbiol. Rev. 8:406 (1995)).

The first published demonstration of the protective efficacy of such a vaccine has shown that intramuscular injection of plasmid DNA encoding influenza A virus (A/PR/8/34) nucleoprotein (NP) elicited protective immune responses in BALB/c mice against a heterologous strain of influenza virus (A/HK/68) (Ulmer, J. B. et al. Science 259:1745 (1993)). Immunized animals had reduced virus titers in their lungs, decreased weight loss, and increased survival compared with challenged control mice. Both NP-specific cytotoxic T lymphocytes (CTL's) and NP antibodies were generated. The NP antibodies were ineffective at conferring protection, but the CTL's killed virus-infected cells and cells pulsed with the appropriated major histocompatibility complex class I-restricted peptide epitope.

Another study has shown that intramuscular injection of plasmid DNA encoding influenza virus A/PR/8/34 hemagglutinin resulted in the generation of neutralizing antibodies that protected mice against a heterologous lethal influenza virus challenge (Montgomery, D. L. et al. DNA Cell Biol. 12:777 (1993)).

Figure 5:
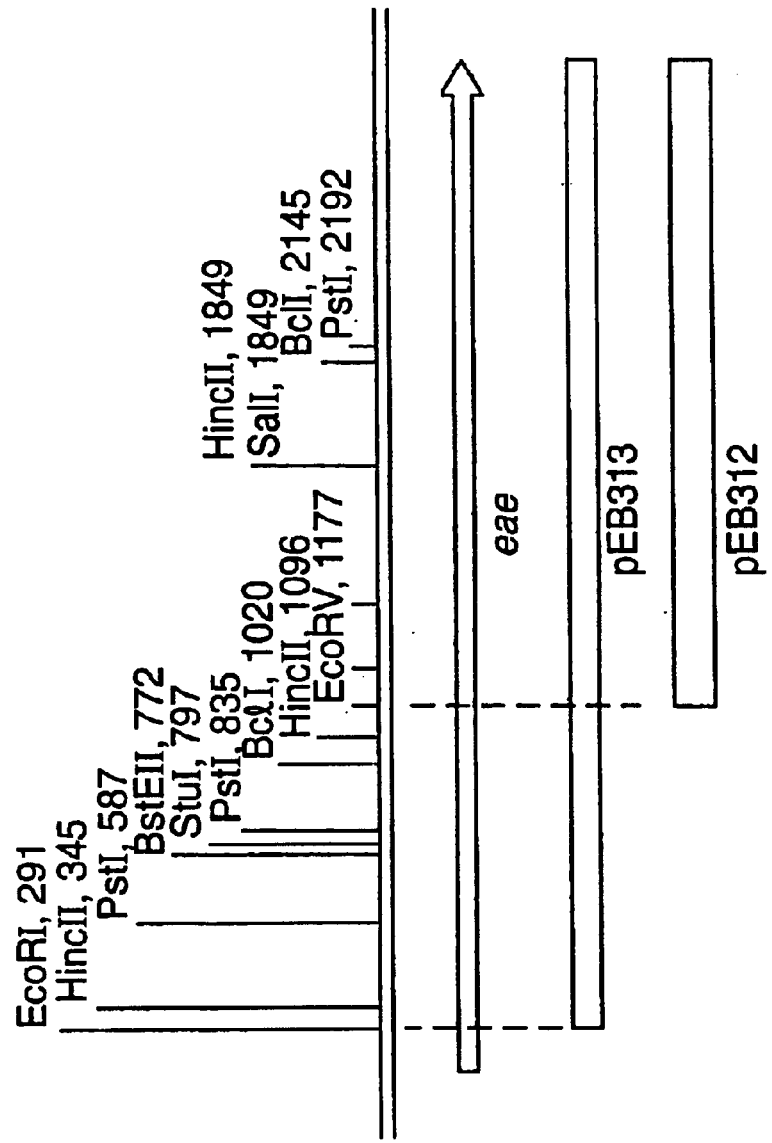
FIG. 5 depicts the 3144 bp fragment of eae produced by polymerase chain reaction amplification, in the region labeled eae.
Figure 6:
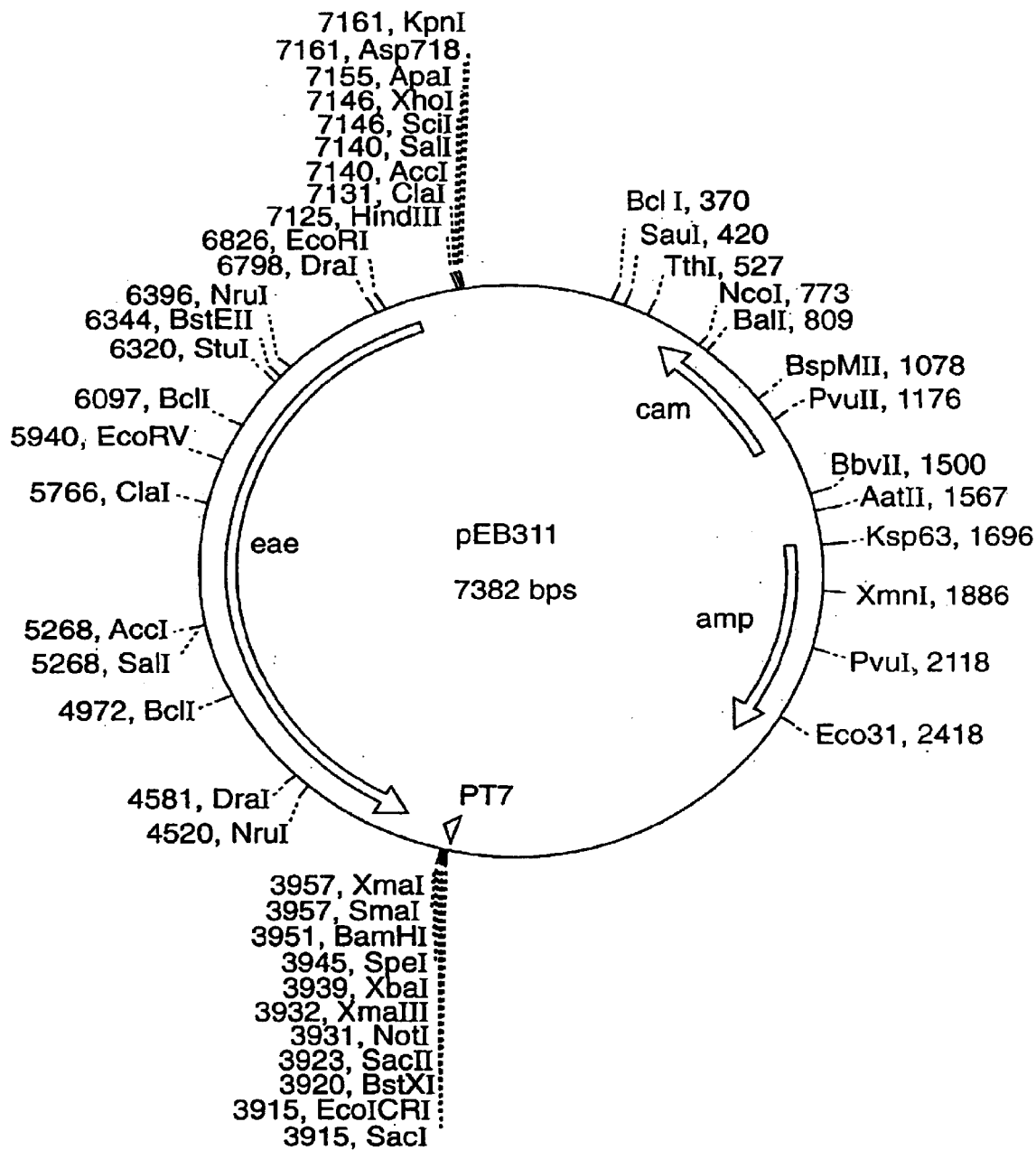
FIG. 6 depicts pEB311, a plasmid encoding EHEC strain 86-24 eae (entire coding sequence) driven by the lac promoter.
Figure 7:
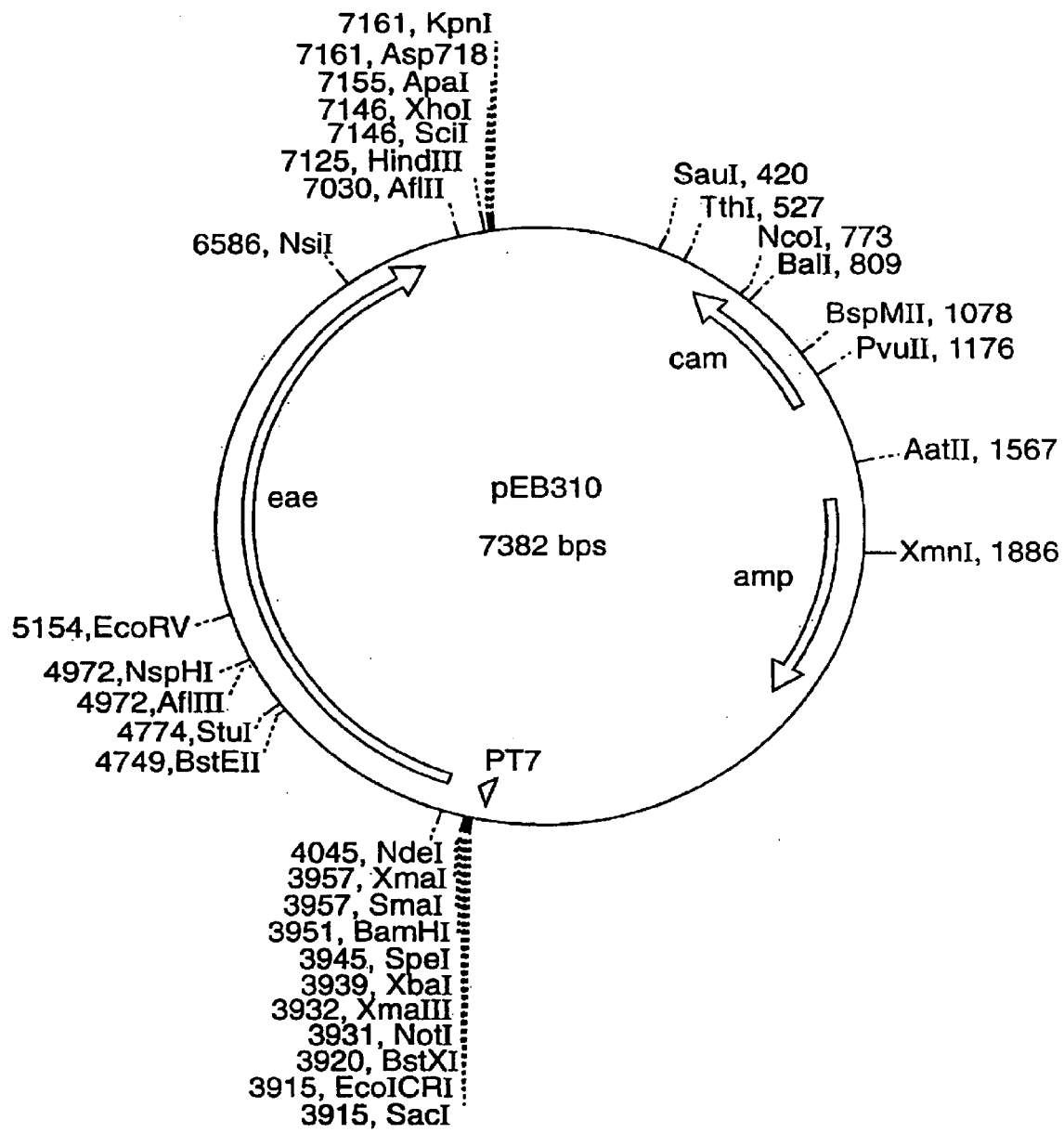
FIG. 7 depicts pEB310, a plasmid encoding EHEC strain 86-24 eae (entire coding sequence) driven by the PT7 promoter.
Figure 8:
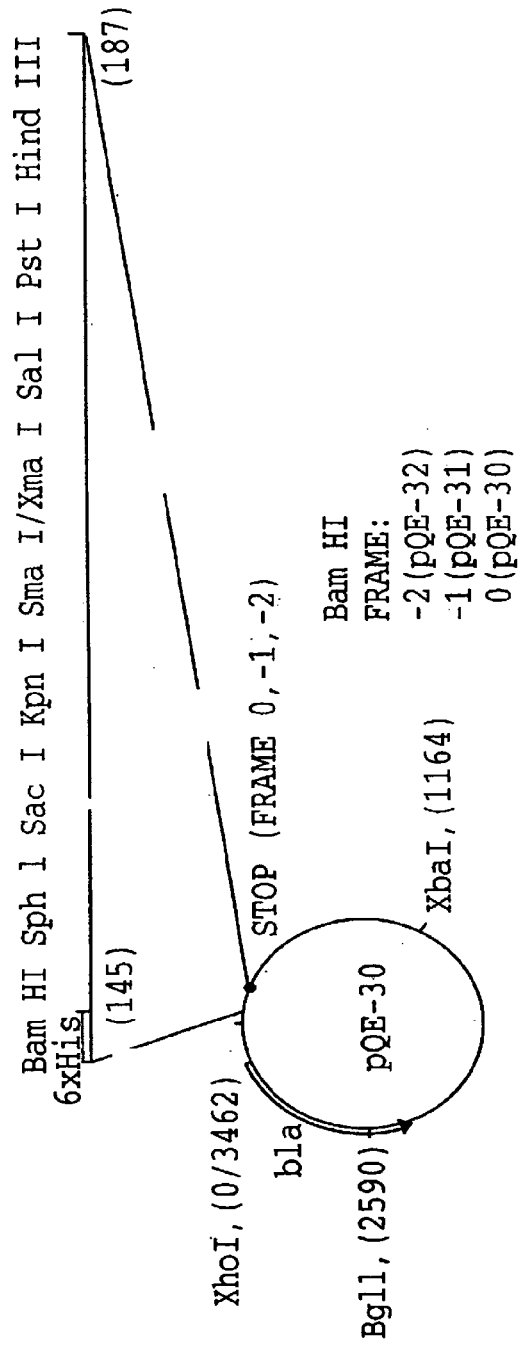
FIG. 8 depicts histidine-tag expression plasmids (Qiagen Inc.). The black box marked "6×His" corresponds to the sequence CAY CAY CAY CAY CAY CAY which encodes 6 histidine residues.
Figure 10:
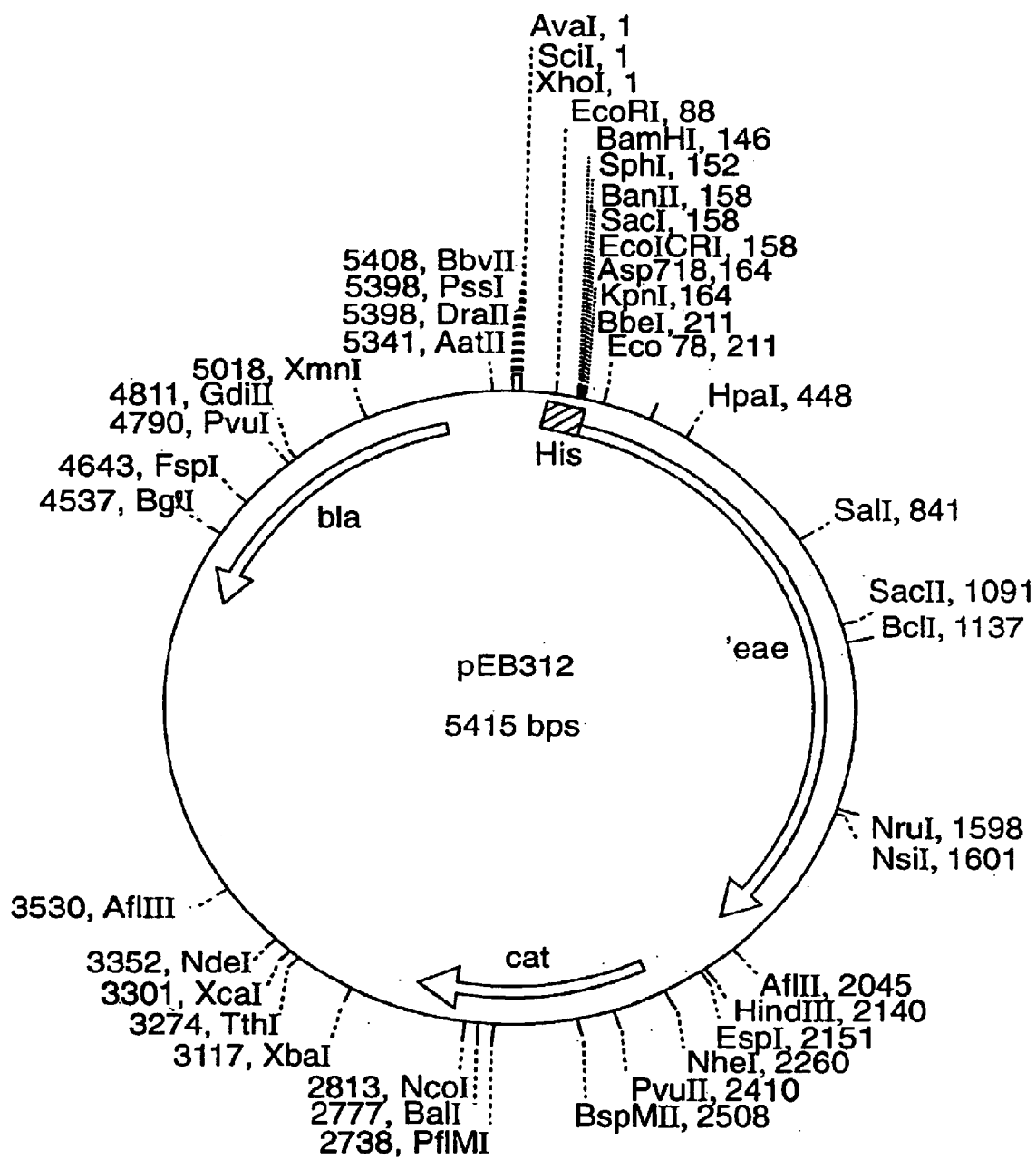
FIG. 10 depicts pEB312, a plasmid encoding RVHindHis. This plasmid encodes a histidine-tagged intimin that spans 604 of 935 predicted amino acids.
Figure 11:
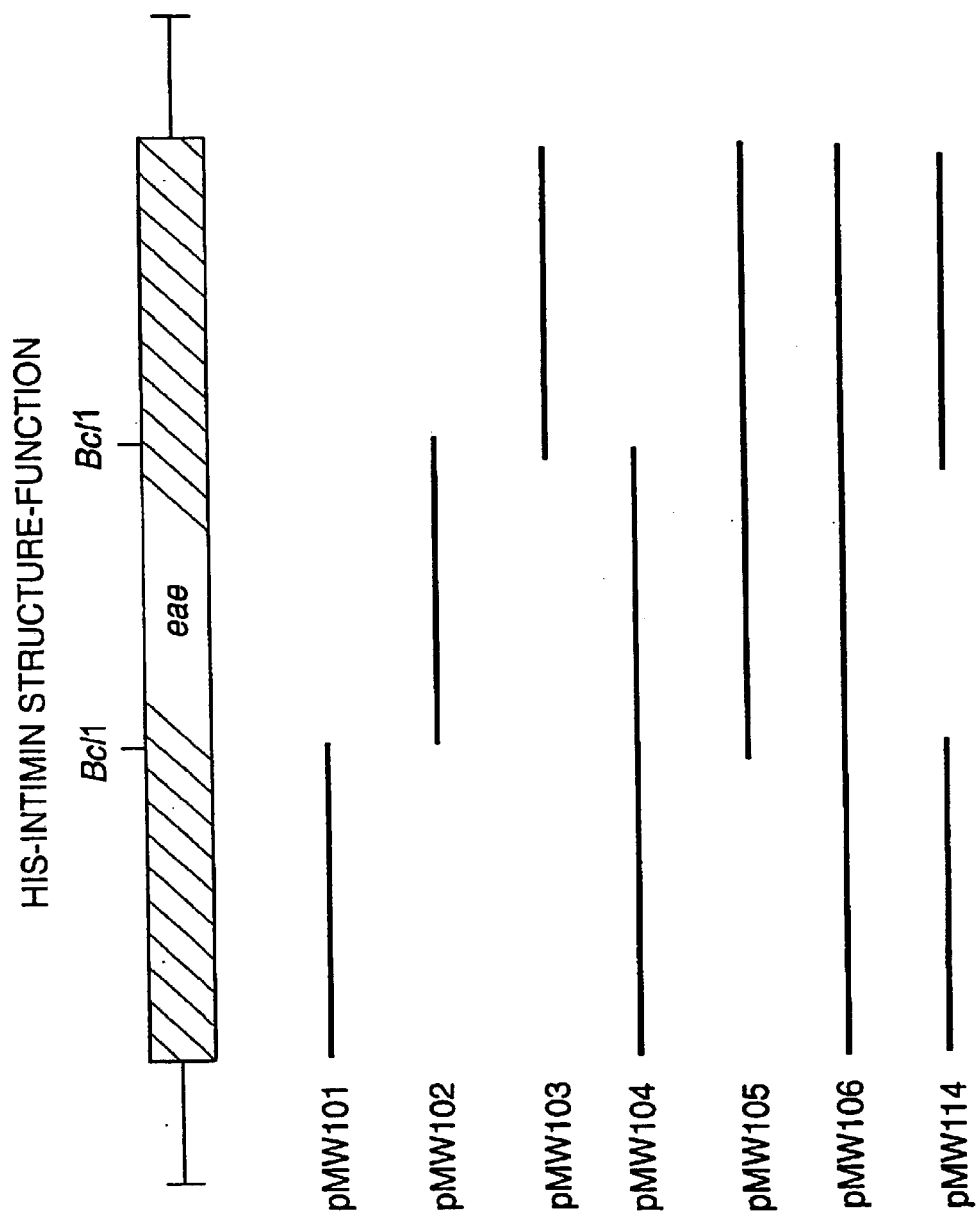
FIG. 11 depicts the different fragments of eae cloned into his-tagged vectors, and the corresponding names of these plasmids.
Figure 12:
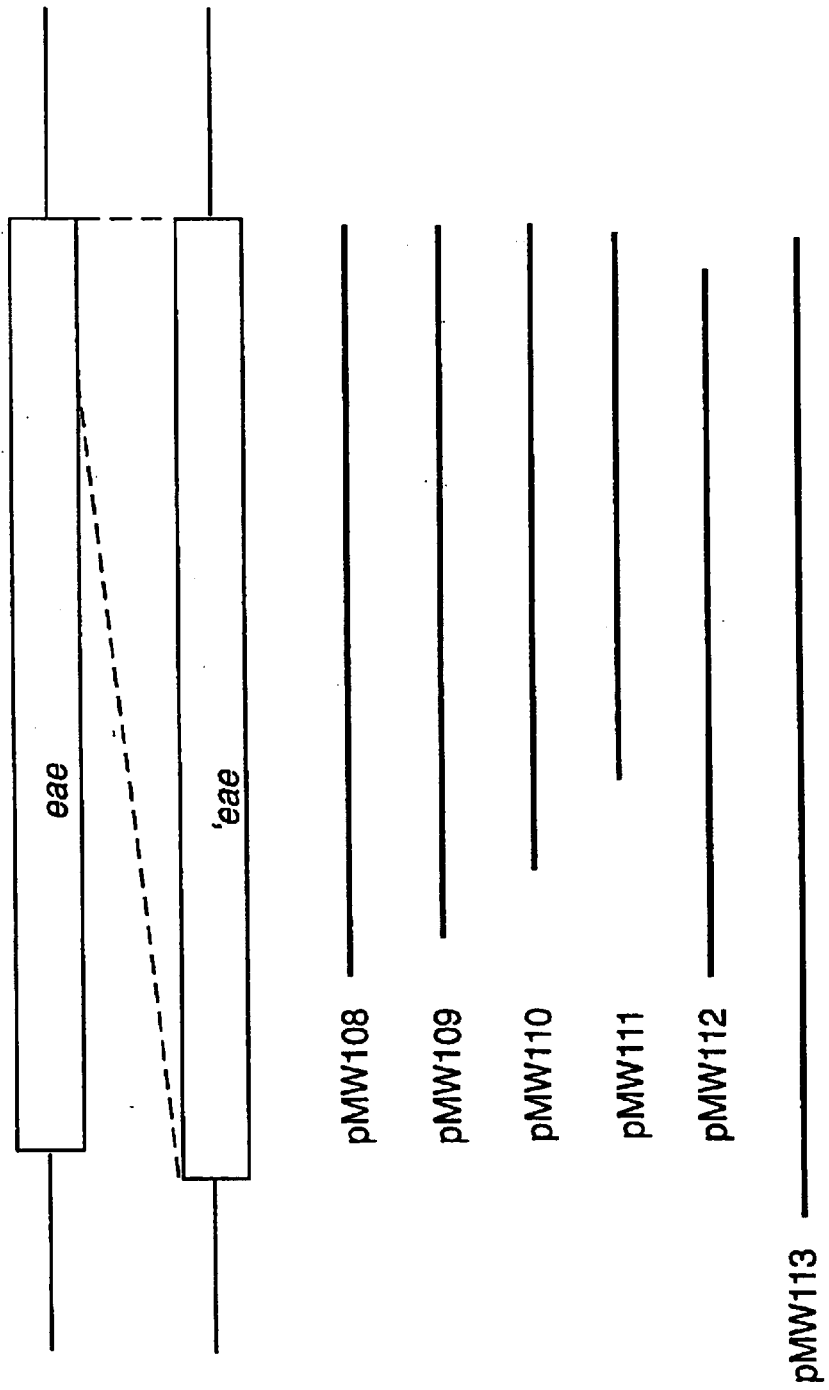
FIG. 12 depicts the different C-terminal fragments of eae cloned into his-tagged vectors and the corresponding names of these plasmids.

Practice of the invention by this method can be accomplished by reference to the aforementioned articles incorporated herein by reference, in particular Montgomery, D. L. et al. DNA Cell Biol. 12:777 (1993). The eae locus is described in FIG. 5 according to restriction sites and according to its sequence in FIG. 3, for strain CL8, and its sequence in strain 933, shown in FIG. 4.

EXAMPLE VIII

A. Conjugation of Antigens from Various Pathogens to His-intimin to Elicit an Immune Response Against both eae and the Conjugated Antigen.

Antigens (Ag) and haptens from various pathogens are conjugated to a histidine-tagged intimin molecule. This fusion protein is used as an inoculum with intimin acting as the carrier to target binding to intestinal epithelial cells. This conjugate protein can be designed in any of the following configurations: N-His-intimin-Ag-C, N-Ag-intimin-His-C, N-His-Ag-intimin-C, N-intimin-Ag-His-C, N-intimin-His-Ag-C, or N-Ag-His-intimin-C.

The size of intimin varies with the size of the antigen that is to be fused, and the number of antigens to which the intimin is fused as would be recognized by those in the art. The variables to be considered in the design of such a fusion protein are: (1) foreign antigen; (2) size of intimin used, which can be of whatever size that retains binding function as described above; (3) fusion order N→C; and (4) method of conjugation, such as genetic, as in cloning and expressing a fusion protein, and chemical, although additional methods are readily apparent to those ordinarily skilled in the art. (D. V. Goeddel, "Systems for Heterologous Gene Expression," Meth. Enzymol., Vol. 185, Academic Press, New York, 1990.; K. Itakura, "Expression in *E. coli* of a chemically synthesized gene for the hormone somatostatin," Science, 198: 1056–1063 (1977); and D. V. Goeddel et al., "Expression of chemically synthesized genes for human insulin," Proc. Natl. Acad. Sci. USA, 281: 544–548 (1979)).

Delivery of this coupled antigen occurs using the same mechanisms as that of a histidine-tagged intimin alone, as set forth above in Example VII.

Haptens and antigens may derive from but are not limited to bacteria, rickettsiae, fungi, viruses, parasites, drugs, or chemicals. They may include, for example, small molecules such as peptides, oligosaccharides, and toxins. Certain antimicrobial drugs and chemotherapeutic drugs having the capacity of being absorbed on the mucosal surface may also be coupled to intimin. The antigens and polysaccharides that may be coupled to intimin and administered to stimulate a protective immune response may include those shown below in Table 1.

TABLE 1

Antigens and/or polysaccharides from:

*Bordetella pertussis*
*Borellia burgdorferi*
Campylobacter sp., including *C. jejuni*
*Candida albicans*, other *Candida*
*Chlamydi trachomatis* and *pneumoniae* (TWAR)
*Citrobacter rodentium*
Clostridium sp., including *C. botulinum, C. difficile, C. perfringens, C. tetani*, (including tetanus toxoid vaccine)
Coronaviruses
*Corynebacterium diphtheriae*, including diptheria toxoid vaccine
*Cryptococcus neoformans*
*Entamoeba histolytica*
*Escherichia coli* sp. including
ETEC (enterotoxigenic *E. coli*),
EAgg EC (enteroaggregative *E. coli*),
EPEC (enteropathogenic *E. coli*),
EHEC (enterohemmorhagic *E. coli*), EHEC SLT subunits or toxoid
EIEC (enteroinvasive *E. coli*),
UPEC (uropathogenic *E. coli*), including *E. coli* endotoxin,
J5 antigen (LPS, Lipid A, Gentabiose),
O polysaccharides (serotype specific)
EHEC
*Haemophilus influenza*, including *H. influenza* type b (polyribose phosphate)
*Hafnia alvei*
*Helicobacter pylori*
Hepatitis A, B, A, and others
Human immunodeficiency virus I and II (GP120, GP41, GP160, p24, and others)
*Histoplasma capsulatum*
Klebsiella species, including polysaccharides (serotype specific)
Legionella species, including *L. micdadei, L. pneumophila*
*Listeria monocytogenes*
Mycobacterium species, including *M. avium, M. kansasii, M. tuberculosis*
Mycoplasma
Neisseria species, including *N. gonorrhoeae, N. meningitidis* (including serotype specific or protein antigens)
*Nocardia asteroides*
Plasmodium species
*Pneumocystis carinii*
Polio virus
*Pseudomonas aeruginosa*, including serotype specific polysaccharides
Rabies virus
Rhinovirus
Rickettsia
Rotavirus
Salmonella sp., including *S. cholerasuis, S. enteriditis, S. typhi, S. typhimurium*
Shigella species, including *S. flexneri, S. sonnei, S. boydii, S. dysenteriae*
Staphylococcus sp., including *S. aureus*, polysaccharides from types 5 and 8 (serotype specific and common protective antigens), *S. epidermidis*, serotype polysaccharide I, II, and III (and common protective antigens)
Streptococcus species, all serotypes including *S. pneumoniae* (all serotypes), *S. pyogenes*, including group A, group B (serotypes Ia, Ib, II, and III)
*Treponema pallidum*
Varicella zoster
*Vibrio cholerae*
Yersinia species, including *Y. pestis, Y. pseudotuberculosis, Y. enterocoliticad*

The sizes of his-intimin and portions of intimin, and intimin-like proteins and portions thereof, that may be conjugated to antigens appearing in Table 1 include RIHisEae (900/935 aa, EcoRI-HindIII fragment of pEB313) and RVHindHis (604/935 aa, EcoRV-HindIII fragment of pEB313), as set forth above in Example I. Those of ordinary skill in the art will recognize that additional fragments of varying lengths having adherence activity may be selected within the spirit and scope of the invention. The efficacy of the fragments considered for selection may be assessed according to the procedures described in Example IV.

B. Construction of a Plasmid Expressing N-His-IcsA-intimin-C.

*Shigella flexneri* causes bacillary dysentery in humans by invading epithelial cells of the colonic mucosa (Labrec et al. J. Becteriol. 88:1503–1518, (1964)). A 120 kDa outer membrane protein, called IcsA, is necessary for intra- and intercellular spread of this organism (Bernardini et al. Proc. Natl. Acad. Sci. USA.86:3867–3871, (1989); Lett et al. J. Bacteriol. 171:353–359, (1989)). An iscA mutant (SC560) was reasonably well tolerated by orally infected macaque monkeys and elicited protection against homologous challenge (Sansonetti et al. Vaccine 9:416–422, 1991).

The following protocol may be used (FIG. 18):

Transform pEB313 into a dam$^-$host, such as DM1 (Gibco BRL, P.O. Box 68, Grand Island, N.Y. 14072, 1-800-828-6686). Digest pEB313/ClaI/HindIII, isolate 1796 bp fragment (this fragment encodes the last 547 amino acids of intimin). Ligate into pBluescriptSK+/ClaI/HindIII (pBluescriptSK+available from Stratagene, 11011 N. Torrey Pines Rd., La Jolla, Calif. 92037, 1-800-424-5444). Call this plasmid pEae1. Digest pHS3192 with AvaI, fill in the end with Klenow fragment, digest with ClaI, isolate 2490 bp fragment [this fragment encodes 2923 bp or 974 aa's from base pair #706–3629; the ORF of icsA spans from bp#574–3880, this is 3306 bp and encodes 1102 aa's; reference for sequence of icsA is Lett et al., J. Bacteriol. 171:353 (1989)](pHS3192 available from P. Sansonetti (ref Bernardini, M. L. et al. Proc. Natl. Acad. Sci. USA. 86:3876 (1989)). Ligate the 2490 bp fragment into pEael digested with ClaI and HincII, producing a plasmid called pEae2. Using these restriction enzymes, the reading frames of icsA and eae remain in frame. Digest pEae2 with XhoI and HindIII, isolate the 4286 bp fragment; ligate into pQE 32 (QIAGEN) digested with SmaI and HindIII. This ligation will maintain the proper reading frame of both genes with the promoter. The resulting plasmid is called picsA-Eae.

Alternatively, one could fuse two genes in frame by cloning with PCR, followed by ligation into the appropriate pQE vector. This technique is well known to those of ordinary skill in the art.

C. Preparation of a Conjugate Vaccine using His-intimin as the Protein Carrier.

While any polysaccharide could be used, in this vaccine the capsular Vi polysaccharide of *Salmonella typhi* is used. Purify His-intimin as in Example II; this would be conjugated to Vi (purified from *S. typhi* according to established procedures (Szu et al. J. Exp. Med. 166:1510 (1987)). The conjugation will proceed using standard protein-polysaccharide conjugation technology well known to those in the art. Methods of conjugation are well known to those of ordinary skill in the art, and include the heteroligation techniques of Brunswick, M. et al., J. Immunol. 140:3364, 1988. See also Chemistry of Protein conjugates and Crosslinking, CRC Press, Boston (1991).

Techniques to conjugate moieties to primary or secondary carriers are well known to those skilled in the art, and include, in part, coupling through available functional groups (such as amino, carboxyl, thio and aldehyde groups). See S. S. Wong, Chemistry of Protein Conjugate and Crosslinking CRC Press (1991); and Brenkeley et al. Brief Survey of Methods for Preparing Protein Conjugates With Dyes, Haptens and Cross-linking Agents, Bioconjugate Chemistry 3 #1 (Jan. 1992).

A vaccine such as that described in this example would provide a prevention of diarrheal pathogens to include both those organisms that express intimin (or intimin-like proteins), as well as a diarrheal pathogen that expresses Vi.

Any combination of intimin plus other antigens from other diarrheal pathogens can be combined. In addition, if polysaccharides were used from organisms that produce other diseases, such as pneumococcal polysaccharides, the intimin-polysaccharide vaccine would be useful for prevention of multiple diseases. Delivery of a vaccine against respiratory pathogens will preferentially be done directly to the respiratory tract; ingested pathogens through ingestion.

EXAMPLE IX

Generation and Testing of Adherence-blocking Anti-intimin Antibodies: Polyclonal and Monoclonal High titer polyclonal anti-intimin antisera are elicited upon intraperitoneal injection of RIHisEae into mice, rabbits, and goats. Testing of antibody titer and an antibody effectiveness assay are shown. The generation of monoclonal antibodies is also described.

A. Generation of Polyclonal Antibodies

Various techniques can be used to prepare antibodies against full-length intimin or various portions thereof in various animals. Several of these techniques are described below. As would be recognized by one skilled in the are, polyclonal antibodies can be generated from intimin and portions of intimin that are not his-tagged and from intimin-like proteins and portions thereof.

1. Generation of Mouse Anti-RIHisEae Polyclonal Antibodies

The technique of Harlow, E. and D. Lane (eds) *Antibodies—a Laboratory Man.* Cold Spring Harbor, N.Y. (1988) may be followed. The general procedure is outlined herein. Take pre-bleeds of each mouse to be immunized: Bleed from the tail vein into an eppendorf tube. Incubate at 37° C. for 30 min, stir gently with a sterile toothpick (to loosen the clot), store overnight at 4° C. In the morning, spin 10 min/10,000 rpm in the microfuge, and collect the serum (i.e., supernatant; red blood cells are the pellet). Store the serum at −20° C. The sera obtained will be used as a negative control after the mice are immunized.

Inject a BALB/c mouse intraperitoneally with 25 $\mu$g of RIHisEae (using Titremax adjuvant, according to the instructions of the manufacturer (CytRyx Corp., 154 Technology Pkwy., Norcross, Ga. 30092, 800-345-2987). Wait 2 weeks, boost with an identical shot, wait 7 days and bleed from the tail vein into an eppendorf tube. Incubate at 37° C. for 30 min, stir gently with a sterile toothpick (to loosen the clot), store overnight at 4° C. In the morning, spin 10 min/10,000 rpm in the microfuge, and collect the serum. Store the sera at −20° C.

2. Generation of Mouse Anti-third Third Portion of Intimin Polyclonal Sera

Mice are prebled by the tail vein as described above in Example IX, part A. The third third portion of intimin is enriched and dialyzed as described above in Example II. Mice are injected with the third third portion of intimin mixed with TitreMax adjuvant, as described in Example IX, part A. After 3 boosts, mice are bled via the retro-orbital sinus, and sera prepared in described Example IX, part A. Sera is tested by Western blot analysis, as described for the goat polyclonal sera in section 4 below. Sera is assayed for the capacity to block EHEC adherence to HEp-2 cells as described above in Example IX, part C.

3. Generation of Rabbit Polyclonal Anti-Intimin Antibodies

Rabbit polyclonal sera is generated against the (1) first third, (2) second third, and (3) third third portions of intimin. Each specific sera is separately assayed in HEp-2 adherence assays for the capacity to block adherence of EHEC to HEp-2 cells.

Preparation of First Third Portion of Intimin for Rabbit Immunization

Clone pMW101 is transformed into strain DH5αF'lacI$^{Q}$. Induction of protein expression and purification of the His-tagged intimin fragment over the Ni-NTA affinity resin is performed as described in the Qiagen manual that accompanies their QIAexpressionist Ni-NTA resin purification kit (Qiagen Inc., Chatsworth, Calif.). Eluted fractions are monitored for protein content by $A_{280}$ and by Bradford analysis, using a dye reagent from Bio-Rad (Hercules, Calif.). Peak fractions eluted from the Ni-NTA column (with 250 mM imidazole) are electrophoresed on 15% polyacrylamide gels with SDS for analysis and purification. To visualize the proteins on the gels for analysis, both silver (Bio-Rad) and Coomassie Blue G-250 (Sigma) staining are used.

To purify the protein for immunization of animals to obtain antisera, the peak column fractions are run on preparative SDS polyacrylamide gels, and proteins are visualized with Copper stain (Bio-Rad). The band of protein corresponding to the intimin fragment is excised from the gel with a clean razor blade, and the gel slice is destained according to the instructions provided with the Copper stain reagent. Protein is then eluted from the gel slice using an Electro-Eluter Model 422 (Bio-Rad) according to the manufacturer's instructions. The protein is then concentrated using a Centricon-10 concentrator from Amicon (Beverly, Mass.). The majority of the SDS in the eluted protein sample is removed by one of two methods. The first method involves addition of phosphate-buffered saline (PBS) to the protein sample, which causes precipitation of SDS. The majority of the protein does not precipitate, and the precipitate is not analyzed to determine what ions may also have precipitated. The SDS is pelleted by centrifugation; and the supernatant, which contains most of the protein and possibly some residual SDS, is removed and concentrated using a Centricon-10 concentrator from Amicon (Beverly, Mass.).

The second method for removal of SDS involves preparing a column of Extracti-Gel$^{R}$D Detergent Removing Gel, purchased from Pierce (Rockford, Ill.). The Extracti-Gel$^{R}$D Detergent Removing Gel is used according to the instructions of the manufacturer. The purified protein is concentrated as described above. Protein concentrations are determined by Bradford analysis using dye reagent purchased from Bio-Rad and also by running different volumes of purified protein on a gel adjacent to aliquots of varying amounts of the original column fractions to compare the amounts of proteins visually. Fractions of this purified protein are analyzed by SDS-PAGE using both silver and Coomassie staining.

Preparation of Second Third Portion of Intimin for Rabbit Immunization

Purification of the His-tagged middle third fragment of the intimin protein expressed from clone pMW102 is performed with the same methods used for the N-terminal third, with the following instructions. SDS-AGE analysis is done using 12.5% acrylamide gels. For gel-purification of the protein and electrolution, most of the preparative gels are stained with Copper stain as above; and one gel is stained with Coomassie brilliant blue dissolved in water as described in Harlow, E. and D. Lane (eds.) *Antibodies—a Laboratory Manual.* Cold Spring Harbor, N.Y. (1988). Much of the SDS in the electroeluted protein fractions is precipitated out by addition of PBS buffer. For concentration of the protein, Amicon Centricon-30 concentrators are used (Amicon).

Preparation of Third Third Portion of Intimin for Rabbit Immunization

The third third intimin protein is enriched and dialyzed as described above in Example II. One mg of protein is run by SDS-PAGE on four BioRad MiniProtean II gels. Protein is negatively stained with copper stain (BioRad, cat # 161-0470, Richmond, Calif.) according to the instructions of the manufacturer as follows: the gel is rinsed in $dH_2O$ for 45 seconds, stained in 1× copper stain for 5 minutes, and rinsed in $dH_2O$ for 3 minutes. The gel is visualized against a black background, and the ~37 kDa protein band is cut from the gel with a razor. Purified gel slices are then de-stained in buffer (25 mM Tris base, 192 mM glycine, 3×/10 min), wrapped in plastic wrap and stored at −20° C. prior to immunization.

Immunization of Rabbits

New Zealand white female rabbits (5 to 6 lbs) are immunized separately with the antigens prepared as described above according to a schedule that could be readily determined by one skilled in the art. An example of such a schedule is as follows:

| DAY | PROCEDURE |
|---|---|
| 0 | Prebleed/initial Inoculation, 100 µg Ag mixed with complete Freund's adjuvant |
| 14 | Boost, 50 µg mixed with incomplete Freund's adjuvant |
| 21 | Boost, 50 µg mixed with incomplete Freund's adjuvant |
| 35 | Test Bleed |
| 45 | Boost, 50 µg mixed with incomplete Freund's adjuvant |
| 56 | Test Bleed |

The route of injection can be subcutaneous and/or intramuscular at multiple sites. Sera derived from test bleeds is tested for specific recognition of the antigen by Western Blot analysis, as described for the goat polyclonal sera in section 4 below. When high titer recognition of the antigen is achieved, as recognizable by one skilled in the art, the rabbit is exsanguinated to recover the antibodies. The large volume sample of blood is verified for specific recognition of the antigen by Western Blot analysis.

Affinity Purification of Rabbit Anti-intimin Polyclonal Sera by Western Blot

Rabbit anti-intimin polyclonal sera is affinity purified to remove cross-reacting antibodies not specific for intimin or intimin-like proteins from the sera. (Harlowe, E. and D. Lane (eds) *Antibodies—a Laboratory Manual*. Cold Spring Harbor, N.Y. (1988), p. 498 or S. H. Lillie and S. S. Brown. Yeast. 3:63 (1987)). RIHisEae (0.250 mg) is electrophoresed by SDS-PAGE (size: BioRad MiniProtean II minigel, BioRad, Richmond, Calif.), transferred to nitrocellulose, and stained with Ponceau S (Sigma, St. Louis, Mo.). A strip of nitrocellulose containing the full length His-intimin band (about 100 kDa) is excised with a razor, and the nitrocellulose strip containing the protein is incubated overnight at 4° C. in 2% milk/TBS-0.2% Tween, shaking gently. The nitrocellulose strip is washed briefly in TBS-Tween, and placed in a container on top of a piece of Parafilm (American National Can, Greenwich, Conn.). Rabbit sera is pipetted onto the mini-Western blot (as much volume as will fit, about 400–500 µl), and wet paper towels are placed over the container, not touching the nitrocellulose strip, followed by plastic wrap. The blot is shaken gently for 5 hours, after which the sera (now called "depleted sera") is removed and saved for analysis. The strip is washed 3 times in PBS for 10 minutes, and glycine buffer (150 mM NaCl, pH 2.3-with HCl) is added (as much volume as will fit onto the strip) for 30 minutes. Affinity purified antibodies are pipetted off, and ¹⁄₁₀volume Tris-HCl, pH 8.0 is added. Antibodies so recovered are then neutralized with 1 N NaOH and tested by Western blot analysis as described below.

Affinity Purification of Rabbit Anti-intimin Polyclonal Sera by Antigen Affinity Column Rabbit anti-intimin polyclonal sera is affinity purified to remove cross-reacting antibodies not specific for intimin from the sera. Antisera raised against intimin or various portions thereof is purified using an antigen affinity column using techniques known to those skilled in the art, such as those described in Harlow, E. and D. Lane (eds.) *Antibodies—a Laboratory Manual*. Cold Spring Harbor, N.Y. (1988).

The antigens (intimin or portions of intimin) are enriched as described above in Example II. Antigens may be further purified by electrophoresis on an acrylamide gel followed by electroelution from a gel slice containing the protein as described below in part 4. Other methods may be substituted for gel-purification and electroelution to further purify the protein after elution from the Ni-NTA resin. These methods may include, but are not limited to, ion-exchange column chromatography and gel filtration chromatography. After purification, the intimin protein may need to be dialyzed into an appropriate buffer for coupling to activated beads to form the affinity resin for antisera purification.

Activated beads appropriate for coupling to the antigen are selected based on several properties: coupling reagent, binding group or matrix, ligand attachment, and stability of the final matrix (as listed in Harlow, E. and D. Lane (eds.) *Antibodies—a Laboratory Manual*. Cold Spring Harbor, N.Y. (1988)). For example, the purified initimin (or portion of intimin) protein antigen is coupled to Affigel beads (Bio-Rad, Richmond, Calif.) according to the instructions of the manufacturer. A column of the activated beads coupled to the antigen is prepared and washed according to instructions of the manufacturer of the beads. The column is then washed according to the method described in Harlow, E. and D. Lane (eds.) *Antibodies—a Laboratory Manual*. Cold Spring Harbor, N.Y. (1988).

Ammonium sulfate precipitation is used to partially purify the sera in preparation for the affinity column. Ammonium sulfate precipitation, resuspension of the protein pellet in PBS, dialysis of the solution versus PBS, and centrifugation to clarify the solution are performed as described in Harlow, E. and D. Lane (eds.) *Antibodies—a Laboratory Manual*. Cold Spring Harbor, N.Y. (1988).

Antisera that has been partially purified by ammonium sulfate precipitation and dialysis versus PBS is passed over the antigen affinity column as described in Harlow, E. and D. Lane (eds.) *Antibodies—a Laboratory Manual*. Cold Spring Harbor, N.Y. (1988). The antisera may be passed over the column multiple times, as this may lead to more complete binding of antibodies to the column. The column is then washed and the affinity-purified antibodies are eluted and dialyzed against PBS as described in Harlow, E. and D. Lane (eds.) *Antibodies—a Laboratory Manual*. Cold Spring Harbor, N.Y. (1988).

Adherence Assays

Affinitiy purified polyclonal sera is assayed in HEp-2 cell adherence assays for the capacity to block bacterial binding to HEp-2 cells using the method described below in Example IX, part C.

4. Generation of Goat Anti-RIHisEae Polyclonal Antibodies

Pre-bleeds are taken of potential goats to be immunized. Blood is collected from the jugular vein with indirect vacuum. Sera is separated from the whole blood, as described above in Example IX, section A, and tested by ELISA using RIHisEae as the adsorbent (as described in Example IX, section B, below for the ELISA and Example II above for the enrichment of RIHisEae), or by Western blot analysis as described below. The goat chosen for immunization has pre-immune sera with both (a) the lowest recognition of intimin by Western blot analysis and (b) the lowest titer against intimin by ELISA, and does not have the habit of jumping out of the pasture.

Western Blot Analysis of Goat Anti-RIHisEae Polyclonal Sera a. Generation of Whole Cell Lysates Desired strains (for example: 86-24, 86-24eaeΔ10, DH5α, M15 pREP4 pEB313) are grown overnight in LB containing the appropriate antibiotics at 37° C., with shaking. Cells (4.5 ml) are pelleted in an eppendorf tube, and 500 µl sonication buffer (50 mM Na-phosphate pH 7.8, 300 mM NaCl) are added. Cells are sonicated in 15 second pulses on ice, aliquoted and frozen at −20° C.

Western Blot Analysis

Whole cell lysates generated as described above (2–5 µl) or purified RIHisEae (2 µl) are run by SDS-PAGE, transferred to nitrocellulose, and used for Western blot analysis of goat sera. The sera (primary antibody) is typically diluted 1:500 or 1:1000 for this purpose. The secondary antibody used is swine anti-goat IgG conjugated to horseradish peroxidase (Boehringer Mannheim, Indianapolis, Ind.), diluted 1:2000. Pre-bleeds of goat sera usually contain several cross-reactive bands that are removed later by affinity purification.

Preparation of Purified RIHisEae (Antigen) for Immunization into Goat

One mg of RIHisEae, generated as described in Example II above, is run by preparative SDS-PAGE. A small analytical lane is stained with Colloidal Coomasie strain (Sigma, St. Louis, Mo.) and used for comparison to the rest of the preparative gel. The high molecular weight full-length intimin band (not stained, running at about 100 kDa) is excised from the preparative gel with a razor, and stored at 4° C. prior to immunization.

Immunization of Goats with Antigen

Female goats (approximately one and a half years old, purebred Saanan or Saanan X LaMANCHA) are immunized separately with the antigens prepared as described above according to a schedule that could be readily determined by one skilled in the art. For example, the goat is given a primary immunization of 500 µg of prepared RIHisEae mixed with Complete Freunds adjuvant. At two week intervals the goat is boosted with 250 µg Ag mixed with incomplete Freunds adjuvant. Test bleeds are begun after the goat has been immunized for a month, and continue until a high anti-intimin titer is reached, as defined by Western blot analysis, described above. When the sera recognizes intimin by Western blot, large blood samples are taken (500 mls, resulting in about 250 mls sera) per session, with two week intervals between large bleeds. Resulting large-volume sera samples are verified for recognition of intimin by Western blot analysis, as described above.

Affinity Purification of Goat Anti-intimin Polyclonal Sera by Western Blot

Goat anti-intimin polyclonal sera is affinity purified to remove cross-reacting antibodies not specific for intimin from the sera. (Harlowe, E. and D. Lane (eds) *Antibodies—a Laboratory Manual*. Cold Spring Harbor, N.Y. (1988), p. 498 or S. H. Lillie and S. S. Brown. Yeast. 3:63 (1987)). RIHisEae (0.250 mg) is electrophoresed by SDS-PAGE (size: BioRad MiniProtean II minigel, BioRad, Richmond, Calif.), transferred to nitrocellulose, and stained with Ponceau S (Sigma, St. Louis, Mo.). A strip of nitrocellulose containing the full length His-intimin band (about 100 kDa) is excised with a razor, and the nitrocellulose strip containing the protein is incubated overnight at 4° C. in 2% milk/TBS-0.2% Tween, shaking gently. The nitrocellulose strip is washed briefly in TBS-Tween, and placed in a container on top of a piece of Parafilm (American National Can, Greenwich, Conn.). Goat sera is pipetted onto the mini-Western blot (as much volume as will fit, about 400–500 µl), and wet paper towels are placed over the container, not touching the nitrocellulose strip, followed by plastic wrap. The blot is shaken gently for 5 hours, after which the sera (now called "depleted sera") is removed and saved for analysis. The strip is washed 3 times in PBS for 10 minutes, and glycine buffer (150 mM NaCl, pH 2.3-with HCl) is added (as much volume as will fit onto the strip) for 30 minutes. Affinity purified antibodies are pipetted off, and 1/10 volume Tris-HCl, pH 8.0 is added. Antibodies are then neutralized with 1N NaOH and tested by Western blot analysis as described above.

Affinity Purification of Goat Anti-intimin Polyclonal Sera by Antigen Affinity Column Goat anti-intimin polyclonal sera is affinity purified to remove cross-reacting antibodies not specific for intimin from the sera. Antisera raised against intimin or various portions thereof is purified using an antigen affinity column using techniques known to those skilled in the art, such as those described in Harlow, E. and D. Lane (eds.) *Antibodies—a Laboratory Manual*. Cold Spring Harbor, N.Y. (1988).

The antigens (intimin or portions of intimin) are enriched as described above in Example II. Antigens may be further purified by electrophoresis on an acrylamide gel followed by electroelution from a gel slice containing the protein as described below in part 4. Other methods may be substituted for gel-purification and electroelution to further purify the protein after elution from the Ni-NTA resin. These methods may include, but are not limited to, ion-exchange column chromatography and gel filtration chromatography. After purification, the intimin protein may need to be dialyzed into an appropriate buffer for coupling to activated beads to form the affinity resin for antisera purification.

Activated beads appropriate for coupling to the antigen are selected based on several properties: coupling reagent, binding group or matrix, ligand attachment, and stability of the final matrix (as listed in Harlow, E. and D. Lane (eds.) *Antibodies—a Laboratory Manual*. Cold Spring Harbor, N.Y. (1988)). For example, the purified initimin (or portion of intimin) protein antigen is coupled to Affigel beads (Bio-Rad, Richmond, Calif.) according to the instructions of the manufacturer. A column of the activated beads coupled to the antigen is prepared and washed according to instructions of the manufacturer of the beads. The column is then washed according to the method described in Harlow, E. and D. Lane (eds.) *Antibodies—a Laboratory Manual*. Cold Spring Harbor, N.Y. (1988).

Ammonium sulfate precipitation is used to partially purify the sera in preparation for the affinity column. Ammonium sulfate precipitation, resuspension of the protein pellet in PBS, and dialysis of the solution versus PBS and centrifugation to clarify the solution is performed as described in Harlow, E. and D. Lane (eds.) *Antibodies—a Laboratory Manual*. Cold Spring Harbor, N.Y. (1988).

The antisera that has been partially purified by ammonium sulfate precipitation and dialysis versus PBS is passed over the antigen affinity column as described in Harlow, E. and D.

Lane (eds.) *Antibodies—a Laboratory Manual*. Cold Spring Harbor, N.Y. (1988). The antisera may be passed over the column multiple times, as this may lead to more complete binding of antibodies to the column. The column is then washed and the affinity-purified antibodies are eluted and dialyzed against PBS as described in Harlow, E. and D. Lane (eds.) *Antibodies—a Laboratory Manual*. Cold Spring Harbor, N.Y. (1988).

Adherence Assays

Affinitiy purified polyclonal sera is assayed in HEp-2 cell adherence assays for the capacity to block bacterial binding to HEp-2 cells using the method described below in Example IX, part C.

B. ELISA to Test Titer of Antibodies

The technique of Harlow, E. and D. Lane (eds) *Antibodies—a Laboratory Manual*. Cold Spring Harbor, N.Y. (1988) may be followed. The general procedure is outlined below:

(1) bind RIHisEae to plastic microtiter plates at 50 ng/well in PBS. Incubate 2 h/RT (room temp) or overnight at 4° C.
(2) wash plate 2× with PBS.
(3) block wells with 100 µl blocking solution [3% bovine serum albumin (Sigma Chemical, St. Louis, Mo.), 0.02% sodium azide (Sigma) in PBS—store stock at 4° C.] for 1–2 h at RT.
(4) wash plate 2× with PBS.
(5) primary Ab=50 µl test sera diluted in blocking solution for example, start with 1:50 and do eleven 1:2 dilutions, or start with 1:50 and do eleven 1:10 dilutions), incubate 2 h/RT.
(6) wash 4× with PBS.
(7) secondary Ab=goat horseradish-conjugated anti-mouse (or other animal being tested) Ig, affinity purified (Boehringer Mannheim Corp., 9115 Hague Rd., P.O. Box 50414, Indianapolis, Ind. 46250, 800-262-1640). Add secondary Ab diluted 1:500 in blocking solution without azide. Incubate 1 h/RT.
(8) wash 4× with PBS.
(9) add 100 µl TMB Peroxidase substrate to each well (prepared according to the instructions of the manufacturer, BioRad Labs, 3300 Regatta Blvd., Richmond, Calif. 94804). Allow blue color to develop (no more than 10 min). Stop the reaction with 100 µl $H_2SO_4$. Read the plate at 450 nm.

A titer is defined as an absorbance value $\geq 0.2$ units above that obtained for mouse pre-immune sera.

Anti-intimin antibodies may be administered to provide passive immune protection to a patient in need thereof. Moreover, anti-intimin antibodies obtained from animals may be used clinically in humans. In such cases, it is preferable to humanize the antibody. Such techniques are well known to those of ordinary skill in the art. See, for example, G. Winter et al., "Man-made antibodies," Nature, 349: 293–299 (1991); P. T. Jones et al., "Replacing the complementarity-determining regions in a human antibody with those from a mouse," Nature, 321: 522–525 (1986); P. Carter et al., "Humanization of an anti-p185$^{HER2}$ antibody for human cancer therapy," Proc. Natl. Acad. Sci. USA, 89: 4285–4289 (1992). Such antibodies may be given to the sibling of an infected patient to reduce the risk of infection of the sibling.

C. Western Blot Analysis of Anti-RIHisEae Polyclonal Sera

Polyclonal sera is assayed by Western blot analysis to verify recognition of intimin.

1. Generation of Whole Cell Lysates

Desired strains (for example: 86-24, 86-24eaeΔ10, DH5α, M15 pREP4 pEB313) are grown overnight in LB containing the appropriate antibiotics at 37° C., with shaking. Cells (4.5 ml) are pelleted in an eppendorf tube, and 500 µl sonication buffer (50 mM Na-phosphate pH 7.8, 300 mM NaCl) are added. Cells are sonicated in 15 second pulses on ice, aliquoted and frozen at −20° C.

2. Western Blot Analysis

Whole cell lysates generated as described above (2–5 µl) or purified RIHisEae (2 µl) are run by SDS-PAGE, transferred to nitrocellulose, and used for Western blot analysis of sera. The sera (primary antibody) is typically diluted 1:500 or 1:1000 for this purpose. The secondary antibody is specific for the animal that is the source of the primary antibody and is conjugated to horseradish peroxidase. Prebleeds of sera may contain several cross-reactive bands that are removed later by affinity purification.

D. Affinity Purification of Anti-intimin Polyclonal Sera by Western Blot

Anti-intimin polyclonal sera is affinity purified to remove cross-reacting antibodies not specific for intimin from the sera. (Harlowe, E. and D. Lane (eds) *Antibodies—a Laboratory Manual*. Cold Spring Harbor, N.Y. (1988), p. 498 or S. H. Lillie and S. S. Brown. Yeast. 3:63 (1987)). RIHisEae (0.250 mg) is electrophoresed by SDS-PAGE (size: BioRad MiniProtean II minigel, BioRad, Richmond, Calif.), transferred to nitrocellulose, and stained with Ponceau S (Sigma, St. Louis, Mo.). A strip of nitrocellulose containing the full length His-intimin band (about 100 kDa) is excised with a razor, and the nitrocellulose strip containing the protein is incubated overnight at 4° C. in 2% milk/TBS-0.2% Tween, shaking gently. The nitrocellulose strip is washed briefly in TBS-Tween, and placed in a container on top of a piece of Parafilm (American National Can, Greenwich, Conn.). Sera is pipetted onto the mini-Western blot (as much volume as will fit, about 400–500 µl), and wet paper towels are placed over the container, not touching the nitrocellulose strip, followed by plastic wrap. The blot is shaken gently for 5 hours, after which the sera (now called "depleted sera") is removed and saved for analysis. The strip is washed 3 times in PBS for 10 minutes, and glycine buffer (150 mM NaCl, pH 2.3-with HCl) is added (as much volume as will fit onto the strip) for 30 minutes. Affinity purified antibodies are pipetted off, and $\frac{1}{10}$ volume Tris-HCl, pH 8.0 is added. Antibodies are then neutralized with 1N NaOH and tested by Western blot analysis as described above.

E. Affinity Purification of Anti-intimin Polyclonal Sera by Antigen Affinity Column Rabbit anti-intimin polyclonal sera is affinity purified to remove cross-reacting antibodies not specific for intimin from the sera. Antisera raised against intimin or various portions thereof is purified using an antigen affinity column using techniques known to those skilled in the art, such as those described in Harlow, E. and D. Lane (eds.) *Antibodies—a Laboratory Manual*. Cold Spring Harbor, N.Y. (1988).

The antigens (intimin or portions of intimin) are enriched as described above in Example II. Antigens may be further purified by electrophoresis on an acrylamide gel followed by electroelution from a gel slice containing the protein as described below in part 4. Other methods may be substituted for gel-purification and electroelution to further purify the protein after elution from the Ni-NTA resin. These methods may include, but are not limited to, ion-exchange column chromatography and gel filtration chromatography. After purification, the intimin protein may need to be dialyzed into an appropriate buffer for coupling to activated beads to form the affinity resin for antisera purification.

Activated beads appropriate for coupling to the antigen are selected based on several properties: coupling reagent, binding group or matrix, ligand attachment, and stability of the final matrix (as listed in Harlow, E. and D. Lane (eds.) *Antibodies—a Laboratory Manual*. Cold Spring Harbor, N.Y. (1988)). For example, the purified initimin (or portion of intimin) protein antigen is coupled to Affigel beads (Bio-Rad, Richmond, Calif.) according to the instructions of the manufacturer. A column of the activated beads coupled to the antigen is prepared and washed according to instructions of the manufacturer of the beads. The column is then washed according to the method described in Harlow, E. and D. Lane (eds.) *Antibodies—a Laboratory Manual*. Cold Spring Harbor, N.Y. (1988).

Ammonium sulfate precipitation is used to partially purify the sera in preparation for the affinity column. Ammonium sulfate precipitation, resuspension of the protein pellet in PBS, and dialysis of the solution versus PBS and centrifugation to clarify the solution is performed as described in Harlow, E. and D. Lane (eds.) *Antibodies—a Laboratory Manual*. Cold Spring Harbor, N.Y. (1988).

The antisera that has been partially purified by ammonium sulfate precipitation and dialysis versus PBS is passed over the antigen affinity column as described in Harlow, E. and D. Lane (eds.) *Antibodies—a Laboratory Manual*. Cold Spring Harbor, N.Y. (1988). The antisera may be passed over the column multiple times, as this may lead to more complete binding of antibodies to the column. The column is then washed and the affinity-purified antibodies are eluted and dialyzed against PBS as described in Harlow, E. and D. Lane (eds.) *Antibodies—a Laboratory Manual*. Cold Spring Harbor, N.Y. (1988).

F. Assay for Blocking of Bacterial Binding by Antibodies to Intimin

To assess the effect of anti-intimin antibodies on EHEC adherence, mouse, rabbit, or goat anti-intimin antisera (or normal sera as controls) are added to EHEC bacteria suspended in adherence media, and the bacteria-antisera mixtures are incubated at 37° C. for thirty minutes prior to infection of HEp-2 cells. Antisera are maintained in the adherence media throughout the assay. Adherence and related sequelae are microscopically observed using GIEMSA and FITC-phalloidin (FAS) staining as described above.

To assess the effect of anti-intimin antibodies on adherence of other bacteria having intimin-like proteins, mouse, rabbit, or goat anti-intimin antisera (or normal sera as controls) are added to EHEC bacteria suspended in adherence media, and the bacteria-antisera mixtures are incubated at 37° C. for thirty minutes prior to infection of HEp-2 cells.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

G. Raising Monoclonal Antibodies Specific for Intimin

Monoclonal antibodies directed against intimin are used to passively protect a patient against colonization by EHEC (or bacteria expressing intimin-like proteins). Monoclonal antibodies are generated from mouse cells, and the specificity of these antibodies are changed for use in humans. G. Winter et al., "Man-made antibodies," Nature, 349: 293–299 (1991); P. T. Jones et al., "Replacing the complementarity-determining regions in a human antibody with those from a mouse," Nature, 321: 522–525 (1986); P. Carter et al., "Humanization of an anti-p185$^{HER2}$ antibody for human cancer therapy," Proc. Natl. Acad. Sci. USA, 89: 4285–4289 (1992). Monoclonal Abs represent a more "pure" antibody for administration to a patient.

1. Generation of Anti-Eae Monoclonal Antibodies

Two examples of methods for generating anti-intimin monoclonal antibodies are described below.

a. Method 1

Generation of Anti-Eae mAbs

The procedure outlined in Harlow, E. and D. Lane, Antibodies, *A Laboratory Manual*, Cold Spring Harbor, N.Y. (1988) is followed with modifications. Nine week old female BALB/c (Harlan Spraque-Dawley, Indianapolis, Ind.) are used for the production of monoclonal antibodies. Prior to immunization, a serum sample is obtained from each mouse via the retro-orbital sinus. The whole blood is placed into a microfuge tube and allowed to cool at 4° C. for between 4 and 16 hours. Serum is prepared by centrifugation of the whole blood at 1000–1200×g for 15 minutes at 10–15° C. The serum is transferred to new microfuge tubes using a micropipettor and sterile pipets tips. The serum is stored at −20° C. until use.

The antigen is obtained from SDS-PAGE gels of RIHisEae, obtained as described above in Example II. The high molecular weight intimin band is excised with a razor, as described above in Example IX, section A, part 4. One mg of RIHisEae is run onto four MiniProtean II gels (BioRad, Richmond, Calif.) for this purpose. Protein excised from the gels are made into a slurry in approximately 8 mls of phosphate buffered saline (PBS) using a mortar and pestle. On experimental day 0, a 0.8 ml portion of the slurry is mixed with 1.2 mls of complete Freund's adjuvant (CFA) and injected in 0.2 ml aliquots subcutaneously into each of four mice. A 0.5 ml portion of the slurry is mixed with 0.5 mls of RIBI T-700 adjuvant (RIBI Immunochem, Hamilton, Mo.) and 0.2 mls is injected into each of four additional mice.

Mice receive booster injections on experimental days 21 and 42. The antigen is prepared as described above, with the exception that incomplete Freund's adjuvant (IFA) is used instead of CFA. Serum samples are obtained as described above on experimental days 14, 35 and 49.

Serum samples are tested by immunoassay (as described below) to identify mice producing serum with the strongest response to Eae, as would be recognized to those skilled in the art. The reactivity of the serum samples is verified by Western blot analysis as described above in Example IX, section A, part 4. Three days prior to fusion (on experimental day 59), the mouse chosen for fusion is immunized with a 50% mixture of supernatant from the intimin slurry in PBS. A total of 0.1 mls of this slurry is injected intravenously via the tail vein.

Spleen cells from the chosen mouse are fused with SP2/0 myeloma cells (Cat # CRL1581 American Type Culture Collection, Rockville, Md. 20850, 301-881-2600). A ratio of 10 spleen cells: 1 myeloma is used for the fusion. Fusion is accomplished by the use of polyethylene glycol (Cat # 783 641 Boehringer-Mannheim Corp., 9115 Hague Road, PO Box 50414, Indianapolis, Ind. 46250, 800-262-1640). Fused cells are distributed into 96-well tissue culture dishes for growth. Hybridomas are selected by growth of the cultures for 10 days in medium containing hypoxanthine, aminopterin and thymidine. Hybridomas secreting anti-intimin specific antibodies are identified from the 96-well tissue culture dishes by immunoassay as described below. Cultures positive for antibodies reactive with Eae are expanded by transfer to 24-well dishes, retested for reactivity with Eae by immunoassay and cloned twice by limiting dilution.

Immunoassay (ELISA) of Mouse Polyclonal Anti-intimin Serum and Hybridoma Supernatants (Anti-intimin Monoclonal Antibodies)

A three ml portion of the intimin slurry used for immunization is centrifuged at approximately 1000×g for 15 minutes at room temperature. A sample of the resulting, clarified supernatant is used to coat immunoassay plates. Briefly, the intimin-containing supernatant is diluted 1:300 in PBS and used as a coating antigen. Nunc Maxisorp Stripwells are coated with 100 μl/well of the diluted supernatant for 2–24 hours at room temperature.

Unbound material is washed from the wells with four washes of PBS containing 0.5% Tween-20 (PBS-T). For assays of serum samples, multiple dilutions of each sample are prepared in PBS-T and added to replicate wells. For assays of culture supernatants from 96-well dish cultures, each supernatant is diluted 1:2 in PBS-T and added to a single well. Supernatants from 24-well dish cultures are also diluted 1:2 in PBS-T and tested in duplicate. Assays of serum samples include a buffer control and a known polyclonal anti-intimin control. Assays of supernatants include a buffer control, medium control and a known polyclonal anti-intimin control.

Serum and supernatants are allowed to incubate in a draft-free environment at room temperature for 30–60 minutes on the intimin-coated wells and unbound antibodies and extraneous material (such as serum proteins) are washed from the wells with four washes of PBS-T. Each well then receives 100 μl of rabbita anti-mouse IgG (gamma specific)-HRP (Zymed, South San Francisco, Calif.), diluted 1:4000 in PBS-T.

The plates are again allowed to incubate in a draft-free environment at room temperature for 30–60 minutes. Each well then receives 100 μl of one-component TMB substrate solution (Kirkegaard and Perry Labs, Gaithersburg, Md. 20878, 301-948-7755). The reaction is allowed to proceed for 15 minutes in the dark and then stopped by the addition of 80 μl/well of TMB stop reagent (Kirkegaard and Perry Labs, Gaithersburg, Md. 20878, 301-948-7755).

b. Method 2

The procedure outlined in Harlow, E. and D. Lane, *Antibodies, A Laboratory Manual*. Cold Spring Harbor, N.Y. (1988) is followed: Five 4- to 5-week old female BALB/cJ mice are prebled, and immunized intraperitoneally with 25 μg RIHisEae suspended in 100 μl of TiterMax. Mice are boosted twice in two week intervals, intraperitoneally with 25 μg RIHisEae suspended in 100 μl of TiterMax. Seven days after each boost, blood (~300–500 μl) is collected from the tail vein. Sera are assayed for the presence of anti-RIHisEae antibody by ELISA (as described above).

Mice producing high titers of anti-RIHisEae antibodies are boosted both intravenously and intraperitoneally with 25 μg of RIHisEae in 100 μl of PBS, sacrificed three days later, and sera collected. Spleen cells are isolated and fused to Sp2/0-Ag mouse myeloma cells (ATCC # CRL1581) at a ratio of 10 spleen cells to 1 myeloma cell. Fused cells are distributed into microdilution plates, and culture supernatants are assayed by ELISA after 3–4 weeks of culture for RIHisEae antibodies. Cultures positive for production of anti-RIHisEae antibodies are expanded and cloned twice by limiting dilution.

2. Determination of Whether Anti-RIHlsEae mAbs Recognize Conformational or Linear Epitopes Reactivities of the mAbs are compared by: 1) ELISA in which native RIHisEae is used as the adsorbent; and 2) immunoblot of RIHisEae denatured and separated by SDS-PAGE. Several pools of mAbs are obtained: 1) those that recognize only conformational epitopes and react positively by ELISA but not by immunoblot analysis; 2) those that recognize linear epitopes and react in both assays; and 3) those that recognize linear epitopes and react positively by immunoblot analysis, but not by ELISA. In addition, colony immunoblots of unlysed cells are done to determine if the mAbs recognize Eae expressed on the surface of the wild type strain 86-24.

3. Testing of Anti-eae mAbs for Capacity to Block Adherence of Strain 86-24 to HEp-2 cells Strain 86-24 is subjected to a qualitative adherence assay on HEp-2 cells and tested in parallel with bacteria that have been pre-incubated with various dilutions of anti-RIHisEae mAbs.

Selected adherence-blocking and conformational mAbs are subjected to isotype determination (Immunopure mAb Typing Kit, Pierce, Rockford, Ill.). Unique antibodies are then purified by affinity chromatography on a Protein G Sepharose column (Pharmacia, Piscataway, N.J.). The resulting affinity-purified mAbs are re-tested for capacity to block adherence of strain 86-24 to Hep-2 cells to ensure that the antibody remains functional after purification.

H. Use of Polyclonal and Monoclonal Anti-intimin Antibodies in Diagnostic Kits.

Diagnostic kits can be used to detect intimin-expressing bacteria, preferably EHEC. A general description of the preparation and use of such kits is provided in copending U.S. application Ser. No. 08/412,231, filed Mar. 10, 1995, the disclosure of which is incorporated herein by reference.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method for providing passive immune protection to a patient in need thereof comprising:
   administering enriched or purified intimin protein to an animal to generate anti-intimin antibodies; and
   administering an amount of the generated anti-intimin antibodies from the animal to the patient effective to provide passive immune protection to the patient,
   wherein the anti-intimin antibodies block binding of enterohemorrhagic *E. coli* to a mammalian cell.

2. The method of claim 1, wherein the animal is chosed from at least one of a domesticated animal, wildlife, and a laboratory animal.

3. The method of claim 2, wherein the animal is a cow, pig, rabbit, or mouse.

4. The method of claim 3, wherein the cow, pig, rabbit, or mouse is milk-producing.

5. The method of claim 4, wherein the patient is an offspring of the milk-producing cow, pig, rabbit, or mouse.

6. The method of claim 3, wherein the patient is a newborn.

7. The method of claim 1, further comprising administering the amount of the generated anti-intimin antibodies through at least one of milk and colostrum.

8. The method of claim 1, wherein the administration of the enriched or purified intimin protein is via injection.

9. The method of claim 8, wherein the injection is intraperitoneal, intravenous, subcutaneous, or intramuscular.

10. The method of claim 1, wherein the administration of the enriched or purified intimin protein is via ingestion, gavage, or intranasal inoculation.

11. The method of claim 1, wherein the administration of the enriched or purified intimin protein further comprises at least one adjuvant.

12. The method of claim 1, wherein the enriched or purified intimin protein is recombinant intimin.

13. The method of claim 12, wherein the recombinant intimin comprises a histidine-tag, and wherein the histidine-tag is optionally removed prior to administration.

14. A method of providing a safer food source, comprising:
   administering enriched or purified intimin protein to a first food mammal to generate anti-intimin antibodies;

administering an amount of the generated anti-intimin antibodies from the first food mammal to a second food mammal, wherein the amount of the generated anti-intimin antibodies is effective to provide passive immune protection to the second food mammal, and wherein the anti-intimin antibodies block binding of enterohemorrhagic *E. colo* to a mammalian cell; and preparing at least one of the first and the second food mammals as a food source for human consumption.

15. The method of claim 14, wherein the first food mammal is a milk-producing mammal, and further comprising administering the amount of the generated anti-intimin antibodies directly from the milk-producing mammal to its offspring.

16. The method of claim 15, further comprising preparing at least one of the offspring and at least one of the first and the second food mammals as a food source for human consumption.

17. The method of claim 14, wherein at least one of the first and second food mammals is at least one of a cow, pig, and rabbit.

18. The method of claim 17, wherein the administration of the enriched or purified intimin protein is via injection.

19. The method of claim 18, wherein the injection is intraperitoneal, intravenous, subcutaneous, or intramuscular.

20. The method of claim 14, wherein the administration of the enriched or purified intimin protein is via ingestion, gavage, or intranasal inoculation.

21. The method of claim 14, wherein the administration of the enriched or purified intimin protein further comprises at least one adjuvant.

22. The method of claim 14, wherein the enriched or purified intimin protein is recombinant intimin.

23. The method of claim 22, wherein the recombinant intimin comprises a histidine-tag, and wherein the histidine-tag is optionally removed prior to administration.

24. A method for providing a safer food source, by providing a food mammal with protection from enterhemorrhagic *E. coli* infection comprising:

administering enriched or purified intimin protein to an animal to generate anti-intimin antibodies; and administering an amount of the generated anti-intimin antibodies from the animal to the food mammal effective to provide passive immune protection to the food mammal, wherein the anti-intimin antibodies block binding of enterohemorrhagic *E. coli* to a mammalian cell, and wherein the safer food source is derived from the food mammal, and the food mammal is chosen from at least one of a domesticated mammal and wildlife.

25. The method of claim 24, wherein said food mammal is at least one of a cow, pig, and rabbit.

26. The method of claim 24, further comprising preparing said at least one food mammal as a food source for human consumption.

27. The method of claim 24, wherein the food mammal is a milk-producing mammal.

28. The method of claim 24, wherein the food mammal is a cow or a calf.

29. The method of claim 28, further comprising preparing the cow or calf as a food source for human consumption.

30. The method of claim 24, wherein the administration of the enriched or purified intimin protein is via injection.

31. The method of claim 30, wherein the injection is at least one of intraperitoneal, intravenous, subcutaneous, and intramuscular.

32. The method of claim 24, wherein the administration of the enriched or purified intimin protein is via ingestion, gavage, or intranasal inoculation.

33. The method of claim 24, wherein the administration of the enriched or purified intimin protein further comprises at least one adjuvant.

34. The method of claim 24, wherein the enriched or purified intimin protein is recombinant intimin.

35. The method of claim 34, wherein the recombinant intimin comprises a histidine-tag, and wherein the histidine-tag is optionally removed prior to administration.

36. A method for providing a laboratory mammal with passive immune protection from enterohemorrhagic *E. coli* infection comprising:

administering enriched or purified intimin protein to an animal to generate anti-intimin antibodies; and administering an amount of the generated anti-intimin antibodies from the animal to the laboratory mammal, wherein the amount of the generated anti-intimin antibodies is effective to provide passive immune protection to said laboratory mammal, and wherein the anti-intimin antibodies block binding of enterohemorrhagic *E. coli* to a mammalian cell.

37. The method of claim 36, wherein the enriched or purified intimin protein is recombinant intimin.

38. The method of claim 37, wherein the recombinant intimin comprises a histidine-tag, and wherein the histidine-tag is optionally removed prior to administration.

\* \* \* \* \*

UNITED STATES PATENT AND TRADEMARK OFFICE
CERTIFICATE OF CORRECTION

PATENT NO. : 6,942,861 B2
DATED : October 19, 2005
INVENTOR(S) : Marian L. McKee et al.

It is certified that error appears in the above-identified patent and that said Letters Patent is hereby corrected as shown below:

Column 55,
Line 57, "chosed" should read -- chosen --.

Column 57,
Line 7, "E. colo" should read -- E. coli --.

Signed and Sealed this

Twenty-ninth Day of November, 2005

JON W. DUDAS
*Director of the United States Patent and Trademark Office*

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 21 base pairs
      (B) TYPE: nucleic acid -continued

```
            (C) STRANDEDNESS: single
            (D) TOPOLOGY: linear (ii) MOLECULE TYPE: DNA (genomic)

(xi) SEQUENCE DESCRIPTION: SEQ ID NO:1:

CGTTGTTAAG TCAATGGAAA C                                          21

(2) INFORMATION FOR SEQ ID NO:2:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:2:

TCTAGAGAGA AAACGTGAAT GTTGTCTCT                                  29

(2) INFORMATION FOR SEQ ID NO:3:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

GTACGGATCC ATGATGGTTT TCCAGCCAAT CAGTGAG                         37

(2) INFORMATION FOR SEQ ID NO:4:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

GTACGGTACC TTATATTGAC AGCGCACAGA GCGGG                           35

(2) INFORMATION FOR SEQ ID NO:5:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

GTACGGATCC ATATGTGGAA TGTTCATGGC TGGGG                           35

(2) INFORMATION FOR SEQ ID NO:6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO:6:

GTACGGATCC GAATTCATTT GCAAATGGTG                                                30

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTACGGTACC TGATCAATGA AGACGTTATA G                                              31

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GTACGGATCC TGATCAGGAT TTTTCTGGTG                                                30

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GTACGGTACC TGATCAAAAA ATATAACCGC                                                30

(2) INFORMATION FOR SEQ ID NO:10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GTACGGATCC TGATCAAACC AAGGCCAGCA TTAC                                           34

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GTACGGTACC TTATTCTACA CAAACCGCAT AG                                             32

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GTACGGATCC ACTGAAAGCA AGCGGTGGTG ATG                             33

(2) INFORMATION FOR SEQ ID NO:13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GTACGGATCC TTCATGGTAT TCAGAAAATA C                               31

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GTACGGATCC GACTGTCGAT GCATCAGGGA AAG                             33

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GTACGGATCC GAATGGTAAA GGCAGTGTCG                                30

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GTACGGTACC TCCAGAACGC TGCTCACTAG                                30

(2) INFORMATION FOR SEQ ID NO:17:

-continued

```
    (i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GTACGGTACC TTATTCTACA GAAACCGCAT AG                                    32

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

ATAACATGAG TACTCATGGT TG                                               22

(2) INFORMATION FOR SEQ ID NO:19:

(i) SEQUENCE CHARACTERISTICS:
        (A) LENGTH: 934 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:
```

Met Ile Thr His Gly Cys Tyr Thr Arg Thr Arg His Lys His Lys Leu
1               5                  10                  15

Lys Lys Thr Leu Ile Met Leu Ser Ala Gly Leu Gly Leu Phe Phe Tyr
            20                  25                  30

Val Asn Gln Asn Ser Phe Ala Asn Gly Glu Asn Tyr Phe Lys Leu Gly
        35                  40                  45

Ser Asp Ser Lys Leu Leu Thr His Asp Ser Tyr Gln Asn Arg Leu Phe
50                  55                  60

Tyr Thr Leu Lys Thr Gly Glu Thr Val Ala Asp Leu Ser Lys Ser Gln
65                  70                  75                  80

Asp Ile Asn Leu Ser Thr Ile Trp Ser Leu Asn Lys His Leu Tyr Ser
                85                  90                  95

Ser Glu Ser Glu Met Met Lys Ala Ala Pro Gly Gln Gln Ile Ile Leu
            100                 105                 110

Pro Leu Lys Lys Leu Pro Phe Glu Tyr Ser Ala Leu Pro Leu Leu Gly
        115                 120                 125

Ser Ala Pro Leu Val Ala Ala Gly Gly Val Ala Gly His Thr Asn Lys
130                 135                 140

Leu Thr Lys Met Ser Pro Asp Val Thr Lys Ser Asn Met Thr Asp Asp
145                 150                 155                 160

Lys Ala Leu Asn Tyr Ala Ala Gln Gln Ala Ala Ser Leu Gly Ser Gln
                165                 170                 175

Leu Gln Ser Arg Ser Leu Asn Gly Asp Tyr Ala Lys Asp Thr Ala Leu
            180                 185                 190

Gly Ile Ala Gly Asn Gln Ala Ser Ser Gln Leu Gln Ala Trp Leu Gln
        195                 200                 205

-continued

```
His Tyr Gly Thr Ala Glu Val Asn Leu Gln Ser Gly Asp Asn Phe Asp
210                 215                 220
Gly Ser Ser Leu Asp Phe Leu Leu Pro Phe Tyr Asp Ser Glu Lys Met
225                 230                 235                 240
Leu Ala Phe Gly Gln Val Gly Ala Arg Tyr Ile Asp Ser Arg Phe Thr
            245                 250                 255
Ala Asn Leu Gly Ala Gly Gln Arg Phe Phe Leu Pro Ala Asn Met Leu
            260                 265                 270
Gly Tyr Asn Val Phe Ile Asp Gln Asp Phe Ser Gly Asp Asn Thr Arg
            275                 280                 285
Leu Gly Ile Gly Gly Glu Tyr Trp Arg Asp Tyr Phe Lys Ser Ser Val
290                 295                 300
Asn Gly Tyr Phe Arg Met Arg Arg Trp His Glu Ser Tyr His Lys Lys
305                 310                 315                 320
Asp Tyr Asp Glu Arg Pro Ala Asn Gly Phe Asp Ile Arg Phe Asn Gly
                325                 330                 335
Tyr Leu Pro Ser Tyr Pro Ala Leu Gly Ala Lys Leu Ile Tyr Glu Gln
                340                 345                 350
Tyr Tyr Gly Asp Asn Val Ala Leu Phe Asn Ser Asp Lys Leu Gln Ser
            355                 360                 365
Asn Pro Gly Ala Ala Thr Val Gly Val Asn Tyr Thr Pro Ile Pro Leu
370                 375                 380
Val Thr Met Gly Ile Asp Tyr Arg His Gly Thr Gly Asn Glu Asn Asp
385                 390                 395                 400
Leu Leu Tyr Ser Met Gln Phe Arg Tyr Gln Phe Asp Lys Ser Trp Ser
                405                 410                 415
Gln Gln Ile Glu Pro Gln Tyr Val Asn Glu Leu Arg Thr Leu Ser Gly
            420                 425                 430
Ser Arg Tyr Asp Leu Val Gln Arg Asn Asn Ile Ile Leu Glu Tyr
            435                 440                 445
Lys Lys Gln Asp Ile Leu Ser Leu Asn Ile Pro His Asp Ile Asn Gly
450                 455                 460
Thr Glu His Ser Thr Gln Lys Ile Gln Leu Ile Val Lys Ser Lys Tyr
465                 470                 475                 480
Gly Leu Asp Arg Ile Val Trp Asp Asp Ser Ala Leu Arg Ser Gln Gly
                485                 490                 495
Gly Gln Ile Gln His Ser Gly Ser Gln Ser Ala Gln Asp Tyr Gln Ala
            500                 505                 510
Ile Leu Pro Ala Tyr Val Gln Gly Gly Ser Asn Ile Tyr Lys Val Thr
            515                 520                 525
Ala Arg Ala Tyr Asp Arg Asn Gly Asn Ser Ser Asn Val Gln Leu
530                 535                 540
Thr Ile Thr Val Leu Ser Asn Gly Gln Val Val Asp Gln Val Gly Val
545                 550                 555                 560
Thr Asp Phe Thr Ala Asp Lys Thr Ser Ala Lys Ala Asp Asn Ala Asp
                565                 570                 575
Thr Ile Thr Tyr Thr Ala Thr Val Lys Lys Asn Gly Val Ala Gln Ala
            580                 585                 590
Asn Val Pro Val Ser Phe Asn Ile Val Ser Gly Thr Ala Thr Leu Gly
            595                 600                 605
Ala Asn Ser Ala Lys Thr Asp Ala Asn Gly Lys Ala Thr Val Thr Leu
610                 615                 620
Lys Ser Ser Thr Pro Gly Gln Val Val Val Ser Ala Lys Thr Ala Glu
```

```
                625                 630                 635                 640
    Met Ser Ser Ala Leu Asn Ala Ser Ala Val Ile Phe Phe Asp Gln Thr
                    645                 650                 655
    Lys Ala Ser Ile Thr Glu Ile Lys Ala Asp Lys Thr Thr Ala Val Ala
                    660                 665                 670
    Asn Gly Lys Asp Ala Ile Lys Tyr Thr Val Lys Val Met Lys Asn Gly
                    675                 680                 685
    Gln Pro Val Asn Asn Gln Ser Val Thr Phe Ser Thr Asn Phe Gly Met
                    690                 695                 700
    Phe Asn Gly Lys Ser Gln Thr Gln Ala Thr Thr Gly Asn Asp Gly Arg
    705                 710                 715                 720
    Ala Thr Ile Thr Leu Thr Ser Ser Ala Gly Lys Ala Thr Val Ser
                    725                 730                 735
    Ala Thr Val Ser Asp Gly Ala Glu Val Lys Ala Thr Glu Val Thr Phe
                    740                 745                 750
    Phe Asp Glu Leu Lys Ile Asp Asn Lys Val Asp Ile Ile Gly Asn Asn
                    755                 760                 765
    Val Arg Gly Glu Leu Pro Asn Ile Trp Leu Gln Tyr Gly Gln Phe Lys
    770                 775                 780
    Leu Lys Ala Ser Gly Gly Asp Gly Thr Tyr Ser Trp Tyr Ser Glu Asn
    785                 790                 795                 800
    Thr Ser Ile Ala Thr Val Asp Ala Ser Gly Lys Val Thr Leu Asn Gly
                    805                 810                 815
    Lys Gly Ser Val Val Ile Lys Ala Thr Ser Gly Asp Lys Gln Thr Val
                    820                 825                 830
    Ser Tyr Thr Ile Lys Ala Pro Ser Tyr Met Ile Lys Val Asp Lys Gln
                    835                 840                 845
    Ala Tyr Tyr Ala Asp Ala Met Ser Ile Cys Lys Asn Leu Leu Pro Ser
                    850                 855                 860
    Thr Gln Thr Val Leu Ser Asp Ile Tyr Asp Ser Trp Gly Ala Ala Asn
    865                 870                 875                 880
    Lys Tyr Ser His Tyr Ser Ser Met Asn Ser Ile Thr Ala Trp Ile Lys
                    885                 890                 895
    Gln Thr Ser Ser Glu Gln Arg Ser Gly Val Ser Ser Thr Tyr Asn Leu
                    900                 905                 910
    Ile Thr Gln Asn Pro Leu Pro Gly Val Asn Val Asn Thr Pro Asn Val
                    915                 920                 925
    Tyr Ala Val Cys Val Glu
                    930

(2) INFORMATION FOR SEQ ID NO:20:

(i) SEQUENCE CHARACTERISTICS:
        (A) LENGTH: 3131 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TCGAGAATGA AATAGAAGTC GTTGTTAAGT CAATGGAAAA CCTGTATTTG GTATTACATA      60

ATCAGGGAAT AACATTAGAA ACGAACATA TGAAAATAGA GGAAATCAGT TCAAGCGACA      120

ATAAACATTA TTACGCCGGA AGATAAAATC CGATCTATTA ATATAATTTA TTTCTCATTC     180

TAACTCATTG TGGTGGAGCC ATAACATGAT TACTCATGGT TGTTATACCC GGACCCGGCA     240
```

```
CAAGCATAAG CTAAAAAAAA CATTGATTAT GCTTAGTGCT GGTTTAGGAT TGTTTTTTTA    300

TGTTAATCAG AATTCATTTG CAAATGGTGA AAATTATTTT AAATTGGGTT CGGATTCAAA    360

ACTGTTAACT CATGATAGCT ATCAGAATCG CCTTTTTTAT ACGTTGAAAA CTGGTGAAAC    420

TGTTGCCGAT CTTTCTAAAT CGCAAGATAT TAATTTATCG ACGATTTGGT CGTTGAATAA    480

GCATTTATAC AGTTCTGAAA GCGAAATGAT GAAGGCCGCG CCTGGTCAGC AGATCATTTT    540

GCCACTCAAA AAACTTCCCT TGAATACAG TGCACTACCA CTTTTAGGTT CGGCACCTCT     600

TGTTGCTGCA GGTGGTGTTG CTGGTCACAC GAATAAACTG ACTAAAATGT CCCCGGACGT    660

GACCAAAAGC AACATGACCG ATGACAAGGC ATTAAATTAT GCGGCACAAC AGGCGGCGAG    720

TCTCGGTAGC CAGCTTCAGT CGCGATCTCT GAACGGCGAT TACGCGAAAG ATACCGCTCT    780

TGGTATCGCT GGTAACCAGG CTTCGTCACA GTTGCAGGCC TGGTTACAAC ATTATGGAAC    840

GGCAGAGGTT AATCTGCAGA GTGGTAATAA CTTTGACGGT AGTTCACTGG ACTTCTTATT    900

ACCGTTCTAT GATTCCGAAA AAATGCTGGC ATTTGGTCAG GTCGGAGCGC GTTACATTGA    960

CTCCCGCTTT ACGGCAAATT TAGGTGCGGG TCAGCGTTTT TTCCTTCCTG CAAACATGTT   1020

GGGCTATAAC GTCTTCATTG ATCAGGATTT TTCTGGTGAT AATACCCGTT TAGGTATTGG   1080

TGGCGAATAC TGGCGAGACT ATTTCAAAAG TAGCGTTAAC GGCTATTTCC GCATGAGCGG   1140

CTGGCATGAG TCATACAATA AGAAAGACTA TGATGAGCGC CCAGCAAATG GCTTCGATAT   1200

CCGTTTTAAT GGCTATCTAC CGTCATATCC GGCATTAGGC GCCAAGCTGA TATATGAGCA   1260

GTATTATGGT GATAATGTTG CTTTGTTTAA TTCTGATAAG CTGCAGTCGA ATCCTGGTGC   1320

GGCGACCGTT GGTGTAAACT ATACTCCGAT TCCTCTGGTG ACGATGGGGA TCGATTACCG   1380

TCATGGTACG GGTAATGAAA ATGATCTCCT TTACTCAATG CAGTTCCGTT ATCAGTTTGA   1440

TAAATCGTGG TCTCAGCAAA TTGAACCACA GTATGTTAAC GAGTTAAGAA CATTATCAGG   1500

CAGCCGTTAC GATCTGGTTC AGCGTAATAA CAATATTATT CTGGAGTACA AGAAGCAGGA   1560

TATTCTTTCT CTGAATATTC CGCATGATAT TAATGGTACT GAACACAGTA CGCAGAAGAT   1620

TCAGTTGATC GTTAAGAGCA AATACGGTCT GGATCGTATC GTCTGGGATG ATAGTGCATT   1680

ACGCAGTCAG GGCGGTCAGA TTCAGCATAG CGGAAGCCAA AGCGCACAAG ACTACCAGGC   1740

TATTTTGCCT GCTTATGTGC AAGGTGGCAG CAATATTTAT AAAGTGACGG CTCGCGCCTA   1800

TGACCGTAAT GGCAATAGCT CTAACAATGT ACAGCTTACT ATTACCGTTC TGTCGAATGG   1860

TCAAGTTGTC GACCAGGTTG GGGTAACGGA CTTTACGGCG ATAAGACTT CGGCTAAAGC    1920

GGATAACGCC GATACCATTA CTTATACCGC GACGGTGAAA AAGAATGGGG TAGCTCAGGC   1980

TAATGTCCCT GTTTCATTTA ATATTGTTTC AGGAACTGCA ACTCTTGGGG CAAATAGTGC   2040

CAAAACGGAT GCTAACGGTA AGGCAACCGT AACGTTGAAG TCGAGTACGC AGGACAGGT    2100

CGTCGTGTCT GCTAAAACCG CGGAGATGAC TTCAGCACTT AATGCCAGTG CGGTTATATT   2160

TTTTGATCAA ACCAAGGCCA GCATTACTGA GATTAAGGCT GATAAGACAA CTGCAGTAGC   2220

AAATGGTAAG GATGCTATTA AATATACTGT AAAAGTTATG AAAAACGGTC AGCCAGTTAA   2280

TAATCAATCC GTTACATTCT CAACAAACTT TGGGATGTTC AACGGTAAGT CTCAAACGCA   2340

AGCAACCACG GGAAATGATG GTCGTGCGAC GATAACACTA ACTTCCAGTT CCGCCGGTAA   2400

AGCGACTGTT AGTGCGACAG TCAGTGATGG GGCTGAGGTT AAAGCGACTG AGGTCACTTT   2460

TTTTGATGAA CTGAAAATTG ACAACAAGGT TGATATTATT GGTAACAATG TCAAGAGGTC   2520

GATGTTGCCT AATATTTGGC TGCAATATGG TCAGTTTAAA CTGAAAGCAA GCGGTGGTGA   2580
```

```
TGGTACATAT TCATGGTATT CAGAAAATAC CAGTATCGCG ACTGTCGATG CATCAGGGAA    2640

AGTCACTTTG AATGGTAAAG GCAGTGTCGT AATTAAAGCC ACATCTGGTG ATAAGCAAAC    2700

AGTAAGTTAC ACTATAAAAG CACCGTCGTA TATGATAAAA GTGGATAAGC AAGCCTATTA    2760

TGCTGATGCT ATGTCCATTT GCAAAAATTT ATTACCATCC ACACAGACGG TATTGTCAGA    2820

TATTTATGAC TCATGGGGGG CTGCAAATAA ATATAGCCAT TATAGTTCTA TGAACTCAAT    2880

AACTGCTTGG ATTAAACAGA CATCTAGTGA GCAGCGTTCT GGAGTATCAA GCACTTATAA    2940

CCTAATAACA CAAACCCTC TTCCTGGGGT TAATGTTAAT ACTCCAAATG TCTATGCGGT    3000

TTGTGTAGAA TAATTCCATA ACCACCCCGG CTAAATATG TATTGTTTTA GTCGGGGCAT    3060

AATTATTTCT TCTTAAGAAA TAACCCTCTT ATAATCAAAT CTACTACTGG TCTTTTTATC    3120

TGCTTAATAG G                                                        3131
```

(2) INFORMATION FOR SEQ ID NO:21:

(i) SEQUENCE CHARACTERISTICS:
        (A) LENGTH: 3106 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
GGAAAGATAA ATCCGATCTA TTAATATAAT TTATTTCTCA TTCTAACTCA TTGTGGTGGA      60

GCCATAACAT GAGTACTCAT GGTTGTTATA CCCGGACCCG GCACAAGCAT AAGCTAAAAA     120

AAACATTGAT TATGCTTAGT GCTGGTTTAG GATTGTTTTT TTATGTTAAT CAGAATTCAT     180

TTGCAAATGG TGAAAATTAT TTTAAATTGG GTTCGGATTC AAAACTGTTA ACTCATGATA     240

GCTATCAGAA TCGCCTTTTT TATACGTTGA AAACTGGTGA AACTGTTGCC GATCTTTCTA     300

AATCGCAAGA TATTAATTTA TCGACGATTT GGTCGTTGAA TAAGCATTTA TACAGTTCTG     360

AAAGCGAAAT GATGAAGGCC GCGCCTGGTC AGCAGATCAT TTTGCCACTC AAAAAACTTC     420

CCTTTGAATA CAGTGCACTA CCACTTTTAG GTTCGGCACC TCTTGTTGCT GCAGGTGGTG     480

TTGCTGGTCA CACGAATAAA CTGACTAAAA TGTCCCCGGA CGTGACCAAA AGCAACATGA     540

CCGATGACAA GGCATTAAAT TATGCGGCAC AACAGGCGGC GAGTCTCGGT AGCCAGCTTC     600

AGTCGCGATC TCTGAACGGC GATTACGCGA AGATACCGC TCTTGGTATC GCTGGTAACC     660

AGGCTTCGTC ACAGTTGCAG GCCTGGTTAC AACATTATGG AACGGCAGAG GTTAATCTGC     720

AGAGTGGTGA TAACTTTGAC GGTAGTTCAC TGGACTTCTT ATTACCGTTC TATGATTCCG     780

AAAAAATGCT GGCATTTGGT CAGGTCGGAG CGCGTTACAT TGACTCCCGC TTTACGGCAA     840

ATTTAGGTGC GGGTCAGCGT TTTTTCCTTC CTGCAAACAT GTTGGGCTAT AACGTCTTCA     900

TTGATCAGGA TTTTTCTGGT GATAATACCC GTTTAGGTAT TGGTGGCGAA TACTGGCGAG     960

ACTATTTCAA AAGTAGCGTT AACGGCTATT TCCGCATGAG GCGCTGGCAT GAGTCATACC    1020

ATAAGAAAGA CTATGATGAG CGCCCAGCAA ATGGCTTCGA TATCCGTTTT AATGGCTATC    1080

TACCGTCATA TCCGGCATTA GGCGCCAAGC TGATATATGA GCAGTATTAT GGTGATAATG    1140

TTGCTTTGTT TAATTCTGAT AAGCTGCAGT CGAATCCTGG TGCGGCGACC GTTGGTGTAA    1200

ACTATACTCC GATTCCTCTG GTGACGATGG GGATCGATTA CCGTCATGGT ACGGGTAATG    1260

AAAATGATCT CCTTTACTCA ATGCAGTTCC GTTATCAGTT TGATAAATCG TGGTCTCAGC    1320

AAATTGAACC ACAGTATGTT AACGAGTTAA GAACATTATC AGGCAGCCGT TACGATCTGG    1380
```

-continued

```
TTCAGCGTAA TAACAATATT ATTCTGGAGT ACAAGAAGCA GGATATTCTT TCTCTGAATA    1440

TTCCGCATGA TATTAATGGT ACTGAACACA GTACGCAGAA GATTCAGTTG ATCGTTAAGA    1500

GCAAATACGG TCTGGATCGT ATCGTCTGGG ATGATAGTGC ATTACGCAGT CAGGGCGGTC    1560

AGATTCAGCA TAGCGGAAGC CAAAGCGCAC AAGACTACCA GGCTATTTTG CCTGCTTATG    1620

TGCAAGGTGG CAGCAATATT TATAAAGTGA CGGCTCGCGC CTATGACCGT AATGGCAATA    1680

GCTCTAACAA TGTACAGCTT ACTATTACCG TTCTGTCGAA TGGTCAAGTT GTCGACCAGG    1740

TTGGGGTAAC GGACTTTACG GCGGATAAGA CTTCGGCTAA AGCGGATAAC GCCGATACCA    1800

TTACTTATAC CGCGACGGTG AAAAAGAATG GGGTAGCTCA GGCTAATGTC CCTGTTTCAT    1860

TTAATATTGT TTCAGGAACT GCAACTCTTG GGGCAAATAG TGCCAAAACG GATGCTAACG    1920

GTAAGGCAAC CGTAACGTTG AAGTCGAGTA CGCCAGGACA GGTCGTCGTG TCTGCTAAAA    1980

CCGCGGAGAT GAGTTCAGCA CTTAATGCCA GTGCGGTTAT ATTTTTTGAT CAAACCAAGG    2040

CCAGCATTAC TGAGATTAAG GCTGATAAGA CAACTGCAGT AGCAAATGGT AAGGATGCTA    2100

TTAAATATAC TGTAAAAGTT ATGAAAAACG GTCAGCCAGT TAATAATCAA TCCGTTACAT    2160

TCTCAACAAA CTTTGGGATG TTCAACGGTA AGTCTCAAAC GCAAGCAACC ACGGGAAATG    2220

ATGGTCGTGC GACGATAACA CTAACTTCCA GTTCCGCCGG TAAAGCGACT GTTAGTGCGA    2280

CAGTCAGTGA TGGGGCTGAG GTTAAAGCGA CTGAGGTCAC TTTTTTTGAT GAACTGAAAA    2340

TTGACAACAA GGTTGATATT ATTGGTAACA ATGTCAGAGG CGAGTTGCCT AATATTTGGC    2400

TGCAATATGG TCAGTTTAAA CTGAAAGCAA GCGGTGGTGA TGGTACATAT TCATGGTATT    2460

CAGAAAATAC CAGTATCGCG ACTGTCGATG CATCAGGGAA AGTCACTTTG AATGGTAAAG    2520

GCAGTGTCGT AATTAAAGCC ACATCTGGTG ATAAGCAAAC AGTAAGTTAC ACTATAAAAG    2580

CACCGTCGTA TATGATAAAA GTGGATAAGC AAGCCTATTA TGCTGATGCT ATGTCCATTT    2640

GCAAAAATTT ATTACCATCC ACACAGACGG TATTGTCAGA TATTTATGAC TCATGGGGGG    2700

CTGCAAATAA ATATAGCCAT TATAGTTCTA TGAACTCAAT AACTGCTTGG ATTAAACAGA    2760

CATCTAGTGA GCAGCGTTCT GGAGTATCAA GCACTTATAA CCTAATAACA CAAAACCCTC    2820

TTCCTGGGGT TAATGTTAAT ACTCCAAATG TCTATGCGGT TTGTGTAGAA TAATTCCATA    2880

ACCACCCCGG CTAAAATATG TATTGTTTTA GTCGGGCAT AATTATTTCT TCTTAAGAAA     2940

TAACCTCTTA TAATCAAATC TACTACTGGT CTTTTTATCT GCTTAATAGG TCTCTTTCAA    3000

AGAGACACAT TCACGTTTTC TAGAGTAGGT TGATCCAACC ACGCTGTATA CCAAAGCTGA    3060

ATCACATCAA GCAACAACTA TGCTCACAAC ATCCACACAA TAAAAA                   3106
```

(2) INFORMATION FOR SEQ ID NO:22:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
ATGAGAGGAT CGCAYCAYCA YCAYCAYCAY GGATCCGCAT GCGACTCGGT ACCCCGGGTC    60

GACCTGCAGC CAAGCTTAAT TAGCTGAG                                       88
```

(2) INFORMATION FOR SEQ ID NO:23:

(i) SEQUENCE CHARACTERISTICS:

```
        (A) LENGTH: 91 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

ATGAGAGGAT CTCAYCAYCA YCAYCAYCAY ACGGATCCGC ATGCGAGCTC GGTACCCCGG         60

GTCGACCTGC AGCCAAGCTT AATTAGCTGA G                                       91

(2) INFORMATION FOR SEQ ID NO:24:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

ATGAGAGGAT CTCAYCAYCA YCAYCAYCAY GGGATCCGCA TGCGAGCTCG GTACCCCGGG         60

TCGACCTGCA GCCAAGCTTA ATTAGCTGAG                                         90

(2) INFORMATION FOR SEQ ID NO:25:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

CTCGAGAAAT CATAAAAAAT TTATTTGCTT TGTGAGCGGA TAACAATTAT AATAGATTCA         60

ATTGTGAGCG GATAACAATT TCACACAGAA TTCATTAAAG AGGAGAAATT AACTATGAGA        120

GGATCGCATC ACCATCACCA TCACGGATCC GCATGCGAGC TCGGTACCCC GGGTCGACCT        180

GCAGCCAAGC TTAATTAGCT GAGCTTGGAC TCCTGTTGAT AGATCCAGTA ATGACCTCAG        240

AACTCCATCT                                                              250
```